(12) United States Patent
Marks et al.

(10) Patent No.: US 9,862,732 B2
(45) Date of Patent: Jan. 9, 2018

(54) REGIOSELECTIVE 1,2-DEAROMATIZATION OF FUNCTIONALIZED AZINES BY ORGANOLANTHANIDE CATALYSTS

(71) Applicant: Northwestern University, Evanston, IL (US)

(72) Inventors: Tobin J. Marks, Evanston, IL (US); Massimiliano Delferro, Chicago, IL (US); Alexander S. Dudnik, Evanston, IL (US); Victoria L. Weidner, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/961,472

(22) Filed: Dec. 7, 2015

(65) Prior Publication Data

US 2016/0159825 A1    Jun. 9, 2016

Related U.S. Application Data

(60) Provisional application No. 62/088,301, filed on Dec. 5, 2014.

(51) Int. Cl.
| | |
|---|---|
| *C07F 7/22* | (2006.01) |
| *C07F 5/02* | (2006.01) |
| *B01J 31/22* | (2006.01) |
| *C07F 17/00* | (2006.01) |

(52) U.S. Cl.
CPC .............. *C07F 5/025* (2013.01); *B01J 31/22* (2013.01); *C07F 7/2212* (2013.01); *C07F 17/00* (2013.01); *B01J 2531/37* (2013.01)

(58) Field of Classification Search
None
See application file for complete search history.

(56) References Cited

PUBLICATIONS

Dudnik et al, Nature Chemistry (Dec. 2014), 6(12), pp. 1100-1107, published online Oct. 2014.*
Griller, D. et al., "Bond Dissociation Energies for Common Organic Compounds", Theochem. J. Mol. Struc. 40, 125-131 (1988).
Bruno, J. W. et al., "Organo-f-Element Thermochemistry. Thorium vs. Uranium and Ancillary Ligand Effects on Metal-Ligand Bond Disruption Enthalpies in Bis(pentamethylcyclopentadienyl)actinide Bis( hydrocarbyls) and Bis (pentamethylcyclopentadienyl)alkoxyactinide Hydrides and Hydrocarbyls", J. Am. Chem. Soc. 108, 7275-7280 (1986).
Bruno, J. W. et al., "Organo-f-Element Thermochemistry. Metal-Ligand Bond Disruption Enthalpies in (Pentamethylcyclopentadienyl)thorium Hydrocarbyls, Metallacycles, Hydrides, and Dialkylamides", J. Am. Chem. Soc. 105, 6824-6832 (1983).
Mcmillen, D. F. et al., "Hydrocarbon Bond-Dissociation Energies", Annu. Rev. Phys. Chem. 33, 493-352 (1982).
Bullock, R. M., "Abundant Metals Give Precious Hydrogenation Performance", Science 342, 1054-1055 (2013).
Eijsbouts, S. et al., "Economic and technical impacts of replacing Co and Ni promotion in hydrotreating catalysts", Appl. Catal. A 458, 169-182 (2013).
Wender, P. et al., "Look through a molecular lens", Nature 469, 23-25 (2011).
Pape, A. R. et al., "Transition-Metal-Mediated Dearomatization Reactions", Chem. Rev. 100, 2917-2940 (2000).
Roche, S. P. et al., Dearomatization Strategies in the Synthesis of Complex Natural Products, Angew. Chem. Int. Ed. 50, 4068-4093 (2011).
Stout, D. M. et al., "Recent Advances in the Chemistry of Dihydropyridines", Chem. Rev. 82, 223-243 (1982).
Edraki, N. et al., Dihydropyridines: evaluation of their current and future pharmacological applications, Drug Discovery Today 14, 1058-1066 (2009).
Lavilla, R., "Recent developments in the chemistry of dihydropyridines", J. Chem. Soc. Perkin Trans. 1 1141-1156 (2002).
Wender, P. A. et al., "Isolation of Diazacycloheptatetraenes from Thermal Nitrene-Nitrene Rearrangements", J. Am. Chem. Soc. 102, 6157-6159 (1980).
Mizoguchi, H. et al., "Biogenetically inspired synthesis and skeletal diversification of indole alkaloids", Nature Chem. 6, 57-64 (2014).
Duttwyler, S. et al., "Regio- and Stereoselective 1,2-Dihydropyridine Alkylation/Addition Sequence for the Synthesis of Piperidines with Quaternary Centers", Angew. Chem. Int. Ed. 53, 3877-3880 (2014).
Satoh, N. et al., "A Practical Synthesis of ( − )--Oseltamivir", Angew. Chem. Int. Ed. 46, 5734-5736 (2007).
Bull, J. A. et al., "Synthesis of Pyridine and Dihydropyridine Derivatives by Regio- and Stereoselective Addition to N-Activated Pyridines", Chem. Rev. 112, 2642-2713 (2012).
Arrowsmith, M. et al., "Magnesium-Catalyzed Hydroboration of Pyridines", Organometallics 30, 5556-5559 (2011).
Oshima, K. et al., "Regioselective Synthesis of 1,2-Dihydropyridines by Rhodium-Catalyzed Hydroboration of Pyridines", J. Am. Chem. Soc. 134, 3699-3702 (2012).
Osakada, K. et at., 1,4-Hydrosilylation of Pyridine by Ruthenium Catalyst: A New Reaction and Mechanism, Angew. Chem. Int. Ed. 50, 3845-3846 (2011).
Hao, L. et al., "Homogeneous Catalytic Hydrosilylation of Pyridines", Angew. Chem. Int. Ed. 37, 3126-3129 (1998).
Gutsulyak, D. V. et al., "Facile Catalytic Hydrosilylation of Pyridines", Angew. Chem. Int. Ed. 50, 1384-1387 (2011).
Lee, S.-H. et al., "Chemo- and Regioselective Catalytic Reduction of N-Heterocydes by Silane", Organometallics 32, 4457-4464 (2013).
Weiss, C. J. et al., "Organo-f-element catalysts for efficient and highly selective hydroalkoxylation and hydrothiolation", Dalton Trans. 39, 6576-6588 (2010).
Harrison, K. N. et al., "Organolanthanide-Catalyzed Hydroboration of Olefins", J. Am. Chem. Soc. 114, 9220-9221 (1992).
Hong, S. et al., "Organolanthanide-Catalyzed Hydroamination", Acc. Chem. Res. 37, 673-686 (2004).
Fu, P.-F. et al., Regioselection and Enantioselection in Organolanthanide-Catalyzed Olefin Hydrosilylation. A Kinetic and Mechanistic Study, J. Am. Chem. Soc. 117, 7157-7168 (1995).

(Continued)

*Primary Examiner* — Zinna Northington Davis
(74) *Attorney, Agent, or Firm* — Reinhart Boerner Van Deuren s.c.

(57) ABSTRACT

A 1,2-regioselective organolanthanide-catalyzed azine dearomatization process using pinacolborane is disclosed.

14 Claims, 59 Drawing Sheets

(56) References Cited

PUBLICATIONS

Obora, Y. et al., Organolanthanide-Catalyzed imine Hydrogenation. Scope, Selectivity, Mechanistic Observations, and Unusual Byproducts, J. Am. Chem. Soc. 119, 3745-3755 (1997).

Jeske, G. et al., Highly Reactive Organolanthanides. Systematic Routes to and Olefin Chemistry of Early and Late Bis(pentamethylcyclopentadienyl) 4f Hydrocarbyl and Hydride Complexes, J. Am. Chem. Soc. 107, 8091-8103 (1985).

Gountchev, T. I. et al., Yttrium Complexes of the Chelating, C2-Symmetric, Bis(silylamido)biphenyl Ligand [DADMB]2- (={[6,6'-Me2-(C6H3)2](2,2'-NSiMe2 tBu)2}2-), Organometallics 18, 2896-2905 (1999).

Reznichenko, A. L, et al., "Early Transition Metal (Group 3-5, Lanthanides and Actinides) and Main Group Metal (Group 1, 2, and 13) Catalyzed Hydroamination", Top. Organomet. Chem. 43, 51-114 (2013).

Oshima, K. et al. "Dearomatizing conversion of pyrazines to 1,4-clihydropyrazine derivatives via transition-metal-free diboration, silaboration, and hydroboration", Chem. Commun. 48, 8571-8573 (2012).

Mannig, D. et al., "Metal Tetrahydridoborates and Tetrahydridoboratometallates XIII. New and Convenient Syntheses of Dicyclopentadienylzirconium Tetrahydridoborate", J. Organomet Chem. 275, 169-171 (1984).

Sevov, C. S. et al., "Iridium-Catalyzed Intermolecular Hydroamination of Unactivated Aliphatic Alkenes with Amides and Sulfonamides", J. Am. Chem. Soc. 134, 11960-11963 (2012).

Muhoro, C. N. et al., "Titanocene Borane σ-Complexes", J. Am. Chem. Soc. 121, 5033-5046 (1999).

Amin, S. B. et al., "Versatile Pathways for In Situ Polyolefin Functionalization with Heteroatoms: Catalytic Chain Transfer", Angew. Chem. Int. Ed. 47, 2006-2025 (2008).

Kozuch, S., "A refinement of everyday thinking: the energetic span model for kinetic assessment of catalytic cycles", WIREs Comput. Mol. Sci. 2, 795-815 (2012).

Kozuch, S. et al., "How to Conceptualize Catalytic Cycles? The Energetic Span Model", Acc. Chem. Res. 44, 101-110 (2011).

Wobser, S. D. et al., "Carbostannolysis Mediated by Bis(pentamethylcyclopentadienyl)lanthanide Catalysts. Utility in Accessing Organotin Synthons", Organometallics 32, 1317-1327 (2013).

Perrin, L et al., "Two [1,2,4-(Me3C)3C5H2]2CeH Molecules are Involved in Hydrogenation of Pyridine to Piperidine as Shown by Experiments and Computations", Inorg Chem, 53, 6261-6373 (2014).

McSkimming, A. et al., "The coordination chemistry of organohydride donors: new prospects for efficient multi-electron reduction", Chem. Soc. Rev. 42, 5439-5488 (2013).

Diaconescu, P. L., "Reactions of Aromatic N-Heterocycles with d0fn-Metal Alkyl Complexes Supported by Chelating Diamide Ligands", Acc. Chem. Res. 43, 1352-1363 (2010).

Jantunen, K. C. et al., "Dearomatization and Functionalization of Terpyridine by Lutetium(III) Alkyl Complexes", J. Am. Chem. Soc. 128, 6322-6323 (2006).

Edelmann, F. T., "Lanthanides and actinides: Annual survey of their organometallic chemistry covering the year 2012", Coord. Chem. Rev. 261, 73-155 (2014).

Minasian, S. G. et al., "Evaluating f-Element Bonding from Structure and Thermodynamics", Chem. Eur. J. 17, 12234-12245 (2011).

Glassey, W. V. et al., "A comparative study of Hamilton and overlap population methods for the analysis of chemical bonding", J. Chem. Phys. 113, 1698-1704 (2000).

Dolomanov, O. V. et al., "OLEX2: a complete structure solution, refinement and analysis program", J. Appl. Crystallogr. 42, 339-341 (2009).

Sheldrick, G. M., "A short history of SHELX", Acta Crystallogr. A 64, 112-122 (2008).

Yang, S. H. et al., "Density Functional Study on the Regioselectivity of Styrene Polymerization with an ansa-Metallocene Catalyst", Organometallics 25, 1144-1150 (2006).

Yang, S. H. et al., "A Density Functional Study on the Stereoselectivity of Styrene Polymerization with ansa-Metallocene Catalyst", Macromolecules 37, 5741-5751 (2004).

Rassolov, V. A. et al., "6-31G* basis set for atoms K through Zn", J. Chem. Phys. 109, 1223-1229 (1998).

Kozuch, S. et al., "How to Conceptualize Catalytic Cycles? The Energetic Span Model", Arc. Chem. Res. 44, 101-110 (2010).

Blanksby, S. J., "Bond Dissociation Energies of Organic Molecules", Acc. Chem Res 36, 255-263 (2003).

Nolan, S. P. et al., "Organo-f-Element Thermochemistry. Absolute Metal-Ligand Bond Disruption Enthalpies in Bis(pentamethylcyclopentaclienyl)samarium Hydrocarbyl, Hydride, Dialkylamide, Alkoxide, Halide, Thiolate, and Phosphide Complexes. Implications for Organolanthanide Bonding and Reactivity", J. Am. Chem. Soc. 111, 7844-7853 (1989).

* cited by examiner

FIG. 39A

Pyridine
| | | | |
|---|---|---|---|
| C | 0.000000000 | 0.000000000 | -1.379777000 |
| C | 0.000000000 | 1.194722000 | -0.670483000 |
| C | 0.000000000 | 1.137964000 | 0.719552000 |
| N | 0.000000000 | 0.000000000 | 1.415640000 |
| C | 0.000000000 | -1.137964000 | 0.719552000 |
| C | 0.000000000 | -1.194722000 | -0.670483000 |
| H | 0.000000000 | 0.000000000 | -2.467419000 |
| H | 0.000000000 | 2.154544000 | -1.180532000 |
| H | 0.000000000 | 2.059032000 | 1.304420000 |
| H | 0.000000000 | -2.059032000 | 1.304420000 |
| H | 0.000000000 | -2.154544000 | -1.180532000 |

HBpin
| | | | |
|---|---|---|---|
| O | 1.062414000 | 1.182413000 | -0.419543000 |
| C | 0.777871000 | -0.186473000 | -0.054681000 |
| B | 0.000001000 | 1.927385000 | -0.000001000 |
| C | -0.777871000 | -0.186473000 | 0.054681000 |
| O | -1.062416000 | 1.182416000 | 0.419534000 |
| H | -0.000001000 | 3.113173000 | -0.000014000 |
| C | 1.473588000 | -0.433207000 | 1.275783000 |
| H | 2.536552000 | -0.194343000 | 1.164338000 |
| H | 1.065196000 | 0.207304000 | 2.065878000 |
| H | 1.386828000 | -1.478933000 | 1.592510000 |
| C | 1.347049000 | -1.104827000 | -1.115767000 |
| H | 1.089520000 | -2.150124000 | -0.902173000 |
| H | 0.982368000 | -0.850272000 | -2.114914000 |
| H | 2.439130000 | -1.020944000 | -1.124508000 |
| C | -1.347047000 | -1.104819000 | 1.115774000 |
| H | -0.982364000 | -0.850257000 | 2.114918000 |
| H | -2.439128000 | -1.020938000 | 1.124518000 |
| H | -1.089517000 | -2.150117000 | 0.902187000 |
| C | -1.473590000 | -0.433217000 | -1.275781000 |
| H | -2.536550000 | -0.194336000 | -1.164344000 |
| H | -1.065184000 | 0.207274000 | -2.065885000 |
| H | -1.386844000 | -1.478950000 | -1.592490000 |

Product 3a
| | | | |
|---|---|---|---|
| O | 0.610740000 | -1.128063000 | 0.152528000 |
| C | 1.985406000 | -0.758775000 | -0.072278000 |
| B | -0.131207000 | -0.000937000 | -0.108292000 |
| C | 1.958031000 | 0.783415000 | 0.163579000 |
| O | 0.628184000 | 1.134600000 | -0.264609000 |
| H | -2.433285000 | -1.631438000 | -1.241043000 |
| C | 2.316633000 | -1.132570000 | -1.510123000 |
| H | 2.094932000 | -2.195013000 | -1.656316000 |
| H | 1.711099000 | -0.558390000 | -2.220806000 |
| H | 3.375445000 | -0.966691000 | -1.740740000 |
| C | 2.866745000 | -1.535198000 | 0.883268000 |

| | | | |
|---|---|---|---|
| H | 3.909149000 | -1.200408000 | 0.806755000 |
| H | 2.536912000 | -1.424217000 | 1.919912000 |
| H | 2.834605000 | -2.600906000 | 0.631468000 |
| C | 2.961007000 | 1.570815000 | -0.652646000 |
| H | 2.802504000 | 1.441073000 | -1.726890000 |
| H | 2.864171000 | 2.637824000 | -0.424147000 |
| H | 3.985639000 | 1.263694000 | -0.407205000 |
| C | 2.068694000 | 1.160231000 | 1.633993000 |
| H | 1.813210000 | 2.219458000 | 1.744089000 |
| H | 1.372182000 | 0.578599000 | 2.248679000 |
| H | 3.084234000 | 1.008575000 | 2.017763000 |
| N | -1.548865000 | -0.012767000 | -0.214108000 |
| C | -4.267602000 | 0.084442000 | 0.357571000 |
| C | -3.640633000 | -1.095760000 | 0.454116000 |
| C | -2.301540000 | -1.273517000 | -0.201160000 |
| C | -2.268273000 | 1.153321000 | -0.451025000 |
| C | -3.598282000 | 1.220454000 | -0.251550000 |
| H | -5.257915000 | 0.223585000 | 0.787229000 |
| H | -4.092437000 | -1.946918000 | 0.957634000 |
| H | -1.694848000 | -2.026840000 | 0.311957000 |
| H | -1.671461000 | 2.010492000 | -0.754336000 |
| H | -4.128558000 | 2.148130000 | -0.439600000 |

[Cp*$_2$LaH]$_2$ precatalyst 1

| | | | |
|---|---|---|---|
| C | -4.477475000 | -1.400255000 | -0.677033000 |
| C | -3.414302000 | -1.788768000 | -1.541519000 |
| C | -3.075672000 | -2.783762000 | 0.507435000 |
| C | -2.547435000 | -2.644156000 | -0.806580000 |
| C | -4.258984000 | -2.011126000 | 0.589386000 |
| La | -2.187382000 | -0.053171000 | 0.324938000 |
| H | -2.386795000 | -0.140534000 | 2.515091000 |
| C | -5.190162000 | -1.935212000 | 1.756790000 |
| H | -5.598314000 | -0.924721000 | 1.895394000 |
| H | -6.049279000 | -2.612165000 | 1.633864000 |
| H | -4.684326000 | -2.204983000 | 2.690198000 |
| C | -2.534869000 | -3.659761000 | 1.593119000 |
| H | -2.479343000 | -3.136503000 | 2.557288000 |
| H | -3.163639000 | -4.549015000 | 1.742810000 |
| H | -1.526543000 | -4.020145000 | 1.356279000 |
| C | -5.724079000 | -0.656264000 | -1.040200000 |
| H | -5.658156000 | -0.198123000 | -2.033087000 |
| H | -6.593116000 | -1.329895000 | -1.051381000 |
| C | -3.239920000 | -1.409606000 | -2.980307000 |
| H | -3.269738000 | -2.285431000 | -3.643306000 |
| H | -4.031285000 | -0.727324000 | -3.313379000 |
| H | -2.279085000 | -0.903544000 | -3.178622000 |
| C | -1.361144000 | -3.365291000 | -1.368546000 |
| H | -0.548566000 | -3.470090000 | -0.635533000 |
| H | -1.621526000 | -4.380122000 | -1.704065000 |
| H | -0.945105000 | -2.840287000 | -2.239418000 |
| H | -5.961724000 | 0.143552000 | -0.323966000 |
| C | -1.129352000 | 2.672967000 | 0.160379000 |
| C | -1.735485000 | 2.415880000 | -1.100566000 |
| C | -3.138622000 | 2.347574000 | -0.904732000 |
| C | -3.397317000 | 2.549415000 | 0.481602000 |
| C | -2.159439000 | 2.761294000 | 1.136787000 |

FIG. 39B

| | | | |
|---|---:|---:|---:|
| C | 0.317595000 | 2.991050000 | 0.395921000 |
| H | 0.749759000 | 2.441763000 | 1.256283000 |
| H | 0.913391000 | 2.811684000 | -0.517998000 |
| H | 0.481834000 | 4.051799000 | 0.633896000 |
| C | -1.064450000 | 2.337411000 | -2.433068000 |
| H | -0.007372000 | 2.056328000 | -2.350990000 |
| H | -1.537420000 | 1.588806000 | -3.085987000 |
| H | -1.101817000 | 3.294873000 | -2.975174000 |
| C | -4.141884000 | 2.289808000 | -2.012609000 |
| H | -4.218858000 | 3.260051000 | -2.524835000 |
| H | -3.878712000 | 1.549771000 | -2.781521000 |
| H | -5.143466000 | 2.040424000 | -1.647442000 |
| C | -4.732544000 | 2.619459000 | 1.153580000 |
| H | -4.980722000 | 3.647493000 | 1.455826000 |
| H | -5.540322000 | 2.276660000 | 0.495680000 |
| H | -4.765858000 | 2.006956000 | 2.066213000 |
| C | -2.011787000 | 3.184625000 | 2.563983000 |
| H | -2.514738000 | 2.498615000 | 3.255894000 |
| H | -0.959217000 | 3.233611000 | 2.865763000 |
| H | -2.438614000 | 4.186215000 | 2.723056000 |
| C | 4.103812000 | 0.653033000 | -1.946686000 |
| C | 4.137640000 | -0.746607000 | -1.704229000 |
| C | 2.155809000 | -0.249522000 | -2.777461000 |
| C | 2.913524000 | -1.296189000 | -2.183672000 |
| C | 2.885591000 | 0.958940000 | -2.621834000 |
| La | 2.175646000 | 0.309992000 | 0.041421000 |
| H | 0.094441000 | -0.520880000 | -0.233505000 |
| C | 2.549681000 | 2.317631000 | -3.157480000 |
| H | 2.390705000 | 3.078528000 | -2.375306000 |
| H | 3.362722000 | 2.699815000 | -3.789584000 |
| H | 1.644263000 | 2.300572000 | -3.773065000 |
| C | 0.880752000 | -0.463539000 | -3.530948000 |
| H | 0.514431000 | 0.461733000 | -3.988349000 |
| H | 1.025019000 | -1.193194000 | -4.339683000 |
| H | 0.076244000 | -0.849119000 | -2.888515000 |
| C | 5.141068000 | 1.666601000 | -1.576218000 |
| H | 6.011147000 | 1.202651000 | -1.098525000 |
| H | 5.504679000 | 2.222026000 | -2.451500000 |
| C | 5.335033000 | -1.541049000 | -1.291167000 |
| H | 5.856741000 | -1.926693000 | -2.178255000 |
| H | 6.060575000 | -0.942437000 | -0.730189000 |
| H | 5.078034000 | -2.412040000 | -0.677118000 |
| C | 2.548955000 | -2.746216000 | -2.228436000 |
| H | 1.497069000 | -2.912456000 | -1.959310000 |
| H | 2.690904000 | -3.168895000 | -3.233827000 |
| H | 3.162574000 | -3.341333000 | -1.541349000 |
| H | 4.760497000 | 2.431818000 | -0.873815000 |
| C | 1.677118000 | -1.176899000 | 2.425695000 |
| C | 2.968531000 | -1.570355000 | 1.975288000 |
| C | 3.844030000 | -0.454767000 | 2.123101000 |
| C | 3.080725000 | 0.626026000 | 2.647532000 |
| C | 1.747861000 | 0.176167000 | 2.854187000 |
| C | 0.502029000 | -2.091188000 | 2.561449000 |
| H | -0.440073000 | -1.540822000 | 2.704017000 |
| H | 0.380253000 | -2.738891000 | 1.682440000 |
| H | 0.612325000 | -2.756266000 | 3.431168000 |
| C | 3.324487000 | -2.968772000 | 1.578497000 |

FIG. 39C

| | | | |
|---|---:|---:|---:|
| H | 2.685783000 | -3.352054000 | 0.768431000 |
| H | 4.364258000 | -3.047776000 | 1.242451000 |
| H | 3.204409000 | -3.661107000 | 2.423176000 |
| C | 5.331542000 | -0.420815000 | 1.959030000 |
| H | 5.825790000 | -0.323118000 | 2.936073000 |
| H | 5.714796000 | -1.335195000 | 1.496119000 |
| H | 5.679726000 | 0.427314000 | 1.350393000 |
| C | 3.619489000 | 2.003474000 | 2.879975000 |
| H | 4.536817000 | 1.986907000 | 3.483027000 |
| H | 3.891243000 | 2.524889000 | 1.940667000 |
| H | 2.896568000 | 2.642816000 | 3.397852000 |
| C | 0.648664000 | 0.922216000 | 3.542131000 |
| H | 0.799978000 | 2.008678000 | 3.510910000 |
| H | -0.347721000 | 0.706835000 | 3.126757000 |
| H | 0.599393000 | 0.642449000 | 4.603636000 |

**[Cp*$_2$LaH]$_2$•Py (V)**

| | | | |
|---|---:|---:|---:|
| C | 5.174996000 | -0.712938000 | 0.664821000 |
| C | 4.236542000 | -1.268586000 | 1.578020000 |
| C | 4.019838000 | -2.370698000 | -0.432413000 |
| C | 3.524129000 | -2.296827000 | 0.898658000 |
| C | 5.028584000 | -1.386158000 | -0.578908000 |
| La | 2.611826000 | 0.148733000 | -0.281569000 |
| H | 2.772575000 | -0.038463000 | -2.462990000 |
| C | 5.890029000 | -1.166816000 | -1.781527000 |
| H | 6.102482000 | -0.101741000 | -1.949051000 |
| H | 6.863291000 | -1.671264000 | -1.680023000 |
| H | 5.413591000 | -1.542912000 | -2.693356000 |
| C | 3.626933000 | -3.363667000 | -1.479914000 |
| H | 3.491249000 | -2.889244000 | -2.460601000 |
| H | 4.390129000 | -4.146081000 | -1.600062000 |
| H | 2.686904000 | -3.871462000 | -1.230370000 |
| C | 6.273987000 | 0.255151000 | 0.969227000 |
| H | 6.136533000 | 0.744601000 | 1.939831000 |
| H | 7.247446000 | -0.255905000 | 0.999150000 |
| C | 4.072872000 | -0.922225000 | 3.025870000 |
| H | 4.351524000 | -1.760773000 | 3.680414000 |
| H | 4.702846000 | -0.070559000 | 3.309630000 |
| H | 3.036641000 | -0.655837000 | 3.291039000 |
| C | 2.556436000 | -3.237222000 | 1.545057000 |
| H | 1.904026000 | -3.728054000 | 0.810684000 |
| H | 3.075309000 | -4.039603000 | 2.091373000 |
| H | 1.905281000 | -2.735063000 | 2.273968000 |
| H | 6.362422000 | 1.047435000 | 0.212119000 |
| C | 1.246927000 | 2.676120000 | -0.322803000 |
| C | 1.871450000 | 2.618266000 | 0.952232000 |
| C | 3.272105000 | 2.738702000 | 0.758487000 |
| C | 3.510090000 | 2.858438000 | -0.640373000 |
| C | 2.257534000 | 2.832049000 | -1.306673000 |
| C | -0.225738000 | 2.642292000 | -0.568311000 |
| H | -0.490065000 | 2.072930000 | -1.474352000 |
| H | -0.736829000 | 2.189187000 | 0.299605000 |
| H | -0.674470000 | 3.640405000 | -0.692419000 |
| C | 1.199041000 | 2.546155000 | 2.285015000 |
| H | 0.181511000 | 2.136661000 | 2.208091000 |
| H | 1.747267000 | 1.904634000 | 2.991284000 |
| H | 1.114858000 | 3.534446000 | 2.762560000 |

FIG. 39D

| | | | |
|---|---:|---:|---:|
| C | 4.261724000 | 2.894531000 | 1.869744000 |
| H | 4.137030000 | 3.863261000 | 2.375693000 |
| H | 4.154734000 | 2.120821000 | 2.644645000 |
| H | 5.294508000 | 2.848970000 | 1.509041000 |
| C | 4.824413000 | 3.060864000 | -1.327077000 |
| H | 4.855563000 | 4.021135000 | -1.861538000 |
| H | 5.659661000 | 3.062027000 | -0.617265000 |
| H | 5.026988000 | 2.279696000 | -2.075871000 |
| C | 2.058411000 | 3.083418000 | -2.767453000 |
| H | 2.732140000 | 2.478445000 | -3.385001000 |
| H | 1.035713000 | 2.845874000 | -3.084445000 |
| H | 2.235064000 | 4.141288000 | -3.015030000 |
| C | -3.753526000 | -0.673155000 | 2.175105000 |
| C | -3.363960000 | -1.986034000 | 1.790699000 |
| C | -1.542465000 | -0.948882000 | 2.741858000 |
| C | -1.991306000 | -2.151490000 | 2.132160000 |
| C | -2.629559000 | -0.034416000 | 2.768993000 |
| La | -1.942209000 | -0.332199000 | -0.033939000 |
| H | 0.323289000 | -0.425131000 | 0.236871000 |
| C | -2.641737000 | 1.286305000 | 3.473062000 |
| H | -3.429527000 | 1.950334000 | 3.095033000 |
| H | -2.826802000 | 1.161668000 | 4.549337000 |
| H | -1.687183000 | 1.822812000 | 3.383518000 |
| C | -0.206409000 | -0.771715000 | 3.392056000 |
| H | -0.006898000 | 0.275638000 | 3.646499000 |
| H | -0.142307000 | -1.348591000 | 4.326803000 |
| H | 0.612422000 | -1.108162000 | 2.743092000 |
| C | -5.156485000 | -0.158651000 | 2.119729000 |
| H | -5.679170000 | -0.485134000 | 1.208141000 |
| H | -5.754157000 | -0.528138000 | 2.965992000 |
| C | -4.317685000 | -3.047737000 | 1.341962000 |
| H | -4.944372000 | -3.385287000 | 2.180160000 |
| H | -5.005107000 | -2.697458000 | 0.559716000 |
| H | -3.800577000 | -3.928897000 | 0.947703000 |
| C | -1.165902000 | -3.393393000 | 1.998108000 |
| H | -0.373358000 | -3.309093000 | 1.237329000 |
| H | -0.655851000 | -3.630881000 | 2.941823000 |
| H | -1.780519000 | -4.261542000 | 1.734826000 |
| H | -5.204874000 | 0.937530000 | 2.150572000 |
| C | -1.034900000 | -1.824089000 | -2.285599000 |
| C | -2.256276000 | -2.435743000 | -1.885373000 |
| C | -3.325444000 | -1.548538000 | -2.218145000 |
| C | -2.753263000 | -0.392590000 | -2.817590000 |
| C | -1.341474000 | -0.565656000 | -2.861050000 |
| C | 0.306538000 | -2.482716000 | -2.221030000 |
| H | 1.123017000 | -1.777554000 | -2.436457000 |
| H | 0.501602000 | -2.934571000 | -1.235685000 |
| H | 0.391455000 | -3.295355000 | -2.958450000 |
| C | -2.365889000 | -3.865494000 | -1.457165000 |
| H | -1.682176000 | -4.117467000 | -0.635553000 |
| H | -3.378706000 | -4.123187000 | -1.129760000 |
| H | -2.112278000 | -4.537657000 | -2.289629000 |
| C | -4.790622000 | -1.849453000 | -2.101412000 |
| H | -5.337034000 | -1.519573000 | -2.994421000 |
| H | -4.964357000 | -2.927084000 | -2.003359000 |
| H | -5.289432000 | -1.381654000 | -1.235221000 |
| C | -3.478974000 | 0.730407000 | -3.494127000 |

FIG. 39E

| | | | |
|---|---:|---:|---:|
| H | -3.247600000 | 0.749829000 | -4.568114000 |
| H | -4.567534000 | 0.629381000 | -3.407334000 |
| H | -3.211173000 | 1.723148000 | -3.102737000 |
| C | -0.398494000 | 0.338704000 | -3.589535000 |
| H | -0.720376000 | 1.388508000 | -3.547890000 |
| H | 0.634607000 | 0.285647000 | -3.216097000 |
| H | -0.357130000 | 0.073357000 | -4.656290000 |
| C | -5.656919000 | 3.773516000 | 0.179792000 |
| C | -4.419113000 | 3.988696000 | 0.774098000 |
| C | -3.430485000 | 3.026780000 | 0.620226000 |
| N | -3.609662000 | 1.892042000 | -0.072501000 |
| C | -4.809024000 | 1.697936000 | -0.640061000 |
| C | -5.855646000 | 2.604067000 | -0.543229000 |
| H | -6.453250000 | 4.506720000 | 0.279315000 |
| H | -4.213338000 | 4.886903000 | 1.348468000 |
| H | -2.450343000 | 3.171828000 | 1.074835000 |
| H | -4.931140000 | 0.772234000 | -1.202642000 |
| H | -6.803992000 | 2.390256000 | -1.026936000 |

**[Cp*$_2$LaH]$_2$•Py$_2$ (VI)**

| | | | |
|---|---:|---:|---:|
| C | -4.697819000 | -0.784166000 | -0.895845000 |
| C | -3.836269000 | -0.058066000 | -1.765154000 |
| C | -3.464991000 | -2.303961000 | -2.100333000 |
| C | -3.074229000 | -0.998045000 | -2.508975000 |
| C | -4.467271000 | -2.172627000 | -1.107509000 |
| La | -2.108092000 | -1.241132000 | 0.207650000 |
| H | -1.622613000 | -3.377844000 | 0.186905000 |
| C | -5.189851000 | -3.306757000 | -0.451866000 |
| H | -5.760619000 | -2.971905000 | 0.423523000 |
| H | -5.903809000 | -3.786069000 | -1.137305000 |
| H | -4.495442000 | -4.088638000 | -0.113442000 |
| C | -3.001595000 | -3.584619000 | -2.717267000 |
| H | -3.044745000 | -4.415250000 | -2.004367000 |
| H | -3.617042000 | -3.857086000 | -3.588707000 |
| H | -1.963942000 | -3.519311000 | -3.070145000 |
| C | -5.795456000 | -0.178974000 | -0.079301000 |
| H | -5.565960000 | 0.857121000 | 0.205110000 |
| H | -6.743452000 | -0.154619000 | -0.637691000 |
| C | -3.825055000 | 1.432857000 | -1.906581000 |
| H | -4.800071000 | 1.817542000 | -2.241157000 |
| H | -3.596727000 | 1.949267000 | -0.960264000 |
| H | -3.081590000 | 1.767395000 | -2.640303000 |
| C | -2.139317000 | -0.706139000 | -3.639889000 |
| H | -1.240373000 | -1.338376000 | -3.608564000 |
| H | -2.614114000 | -0.892240000 | -4.614740000 |
| H | -1.803555000 | 0.338890000 | -3.643748000 |
| H | -5.989150000 | -0.738165000 | 0.846433000 |
| C | -0.835773000 | -0.990223000 | 2.780428000 |
| C | -1.566673000 | 0.217928000 | 2.615669000 |
| C | -2.948854000 | -0.088950000 | 2.702382000 |
| C | -3.066423000 | -1.494629000 | 2.904523000 |
| C | -1.760628000 | -2.049409000 | 2.967462000 |
| C | 0.652936000 | -1.077346000 | 2.839621000 |
| H | 1.027747000 | -2.076921000 | 2.589955000 |
| H | 1.116245000 | -0.361508000 | 2.136217000 |
| H | 1.061329000 | -0.812687000 | 3.828519000 |
| C | -0.956468000 | 1.571696000 | 2.440266000 |

FIG. 39F

| | | | |
|---|---:|---:|---:|
| H  | -0.142942000 | 1.551618000  | 1.694699000 |
| H  | -1.687822000 | 2.316819000  | 2.095436000 |
| H  | -0.519200000 | 1.959810000  | 3.375653000 |
| C  | -4.051119000 | 0.919584000  | 2.774426000 |
| H  | -4.186492000 | 1.281500000  | 3.804299000 |
| H  | -3.838260000 | 1.801199000  | 2.155007000 |
| H  | -5.014409000 | 0.507083000  | 2.454552000 |
| C  | -4.329379000 | -2.266216000 | 3.129360000 |
| H  | -4.456888000 | -2.542284000 | 4.186472000 |
| H  | -5.217094000 | -1.689494000 | 2.839684000 |
| H  | -4.348086000 | -3.204186000 | 2.555316000 |
| C  | -1.449265000 | -3.470149000 | 3.313348000 |
| H  | -2.150642000 | -4.165614000 | 2.839002000 |
| H  | -0.447211000 | -3.766928000 | 2.982368000 |
| H  | -1.500898000 | -3.636319000 | 4.400368000 |
| C  | 3.316936000  | 2.552820000  | -0.985550000 |
| C  | 3.219958000  | 1.860490000  | -2.223752000 |
| C  | 1.086027000  | 2.267862000  | -1.460464000 |
| C  | 1.836546000  | 1.678416000  | -2.513702000 |
| C  | 1.999454000  | 2.815297000  | -0.520427000 |
| La | 2.296549000  | -0.072777000 | -0.338347000 |
| H  | 0.067704000  | -0.467309000 | -0.460478000 |
| C  | 1.636905000  | 3.684639000  | 0.641808000 |
| H  | 2.375610000  | 3.630353000  | 1.452752000 |
| H  | 1.579061000  | 4.741766000  | 0.342909000 |
| H  | 0.659854000  | 3.424253000  | 1.069374000 |
| C  | -0.401691000 | 2.410832000  | -1.441605000 |
| H  | -0.816722000 | 2.405032000  | -0.423382000 |
| H  | -0.729188000 | 3.353401000  | -1.909730000 |
| H  | -0.889025000 | 1.593543000  | -1.987309000 |
| C  | 4.593724000  | 3.061853000  | -0.396079000 |
| H  | 5.407554000  | 2.323618000  | -0.461195000 |
| H  | 4.950702000  | 3.958961000  | -0.923334000 |
| C  | 4.377703000  | 1.610981000  | -3.139032000 |
| H  | 4.800718000  | 2.561038000  | -3.496572000 |
| H  | 5.201949000  | 1.063890000  | -2.658748000 |
| H  | 4.083355000  | 1.036205000  | -4.023492000 |
| C  | 1.240129000  | 1.081376000  | -3.750536000 |
| H  | 0.633258000  | 0.185661000  | -3.546790000 |
| H  | 0.571941000  | 1.794578000  | -4.253120000 |
| H  | 2.010425000  | 0.796435000  | -4.475593000 |
| H  | 4.483907000  | 3.336177000  | 0.661226000 |
| C  | 2.255708000  | -2.667713000 | -1.527826000 |
| C  | 3.396092000  | -1.999085000 | -2.055352000 |
| C  | 4.362386000  | -1.885088000 | -1.008719000 |
| C  | 3.807635000  | -2.481187000 | 0.158060000 |
| C  | 2.511586000  | -2.970080000 | -0.168557000 |
| C  | 1.058573000  | -3.099839000 | -2.313373000 |
| H  | 0.207322000  | -3.337847000 | -1.659545000 |
| H  | 0.727221000  | -2.325450000 | -3.020992000 |
| H  | 1.274843000  | -3.998057000 | -2.911190000 |
| C  | 3.623837000  | -1.751216000 | -3.514017000 |
| H  | 2.779504000  | -1.243207000 | -3.998424000 |
| H  | 4.517911000  | -1.145377000 | -3.696414000 |
| H  | 3.760888000  | -2.703270000 | -4.047073000 |
| C  | 5.751344000  | -1.336081000 | -1.153784000 |
| H  | 6.432215000  | -1.771717000 | -0.411996000 |

FIG. 39G

| | | | |
|---|---|---|---|
| H  |  6.169750000 | -1.570341000 | -2.140420000 |
| H  |  5.823065000 | -0.238816000 | -1.047940000 |
| C  |  4.498473000 | -2.731026000 |  1.464150000 |
| H  |  4.742731000 | -3.795878000 |  1.583291000 |
| H  |  5.441221000 | -2.178109000 |  1.549618000 |
| H  |  3.883665000 | -2.454462000 |  2.332561000 |
| C  |  1.666558000 | -3.847798000 |  0.698639000 |
| H  |  1.962916000 | -3.784300000 |  1.753235000 |
| H  |  0.590759000 | -3.627803000 |  0.624706000 |
| H  |  1.784727000 | -4.901340000 |  0.406218000 |
| C  |  5.192563000 |  1.979942000 |  3.901369000 |
| C  |  3.808560000 |  2.105244000 |  3.906890000 |
| C  |  3.079912000 |  1.483398000 |  2.902489000 |
| N  |  3.649008000 |  0.768725000 |  1.919963000 |
| C  |  4.984954000 |  0.658127000 |  1.924480000 |
| C  |  5.793657000 |  1.240449000 |  2.890336000 |
| H  |  5.793537000 |  2.453132000 |  4.673741000 |
| H  |  3.293210000 |  2.672683000 |  4.675849000 |
| H  |  1.992541000 |  1.568428000 |  2.879922000 |
| H  |  5.425848000 |  0.081632000 |  1.110186000 |
| H  |  6.871139000 |  1.115668000 |  2.842317000 |
| C  | -4.419654000 |  5.303761000 | -1.322110000 |
| C  | -5.281795000 |  4.598782000 | -0.490388000 |
| C  | -4.743200000 |  3.926825000 |  0.601876000 |
| N  | -3.441658000 |  3.923330000 |  0.900322000 |
| C  | -2.628987000 |  4.613034000 |  0.098665000 |
| C  | -3.062797000 |  5.313717000 | -1.022335000 |
| H  | -4.799191000 |  5.835608000 | -2.191535000 |
| H  | -6.350274000 |  4.561322000 | -0.684292000 |
| H  | -5.390452000 |  3.352800000 |  1.268334000 |
| H  | -1.567868000 |  4.598825000 |  0.358905000 |
| H  | -2.349578000 |  5.850819000 | -1.642399000 |

FIG. 39H

Structure VII
| | | | |
|---|---|---|---|
| C  | -2.066388000 |  2.154033000 |  0.221183000 |
| C  | -1.120037000 |  2.228333000 |  1.289448000 |
| C  | -0.059197000 |  2.880931000 | -0.657794000 |
| C  |  0.119977000 |  2.676545000 |  0.744854000 |
| C  | -1.408608000 |  2.560447000 | -0.981180000 |
| La | -0.223885000 |  0.002449000 | -0.336710000 |
| H  |  0.186481000 | -0.010787000 | -2.501057000 |
| C  | -2.066418000 |  2.748437000 | -2.324078000 |
| H  | -2.897782000 |  2.051900000 | -2.475619000 |
| H  | -2.479249000 |  3.762084000 | -2.428684000 |
| H  | -1.362491000 |  2.591964000 | -3.145681000 |
| C  |  0.965806000 |  3.453215000 | -1.601940000 |
| H  |  0.784727000 |  3.137241000 | -2.632899000 |
| H  |  0.956479000 |  4.552440000 | -1.589082000 |
| H  |  1.984199000 |  3.144075000 | -1.340432000 |
| C  | -3.545099000 |  1.899240000 |  0.367790000 |
| H  | -3.771996000 |  1.274595000 |  1.237950000 |
| H  | -4.099811000 |  2.838845000 |  0.500509000 |
| C  | -1.421255000 |  2.042371000 |  2.754527000 |
| H  | -1.730495000 |  2.986614000 |  3.224794000 |
| H  | -2.230211000 |  1.325171000 |  2.922531000 |
| H  | -0.549651000 |  1.685926000 |  3.315831000 |

|   |   |   |   |
|---|---:|---:|---:|
| C | 1.348784000 | 3.039012000 | 1.539229000 |
| H | 2.268302000 | 2.922515000 | 0.956300000 |
| H | 1.316785000 | 4.085426000 | 1.873947000 |
| H | 1.453201000 | 2.427509000 | 2.443178000 |
| H | -3.972250000 | 1.404374000 | -0.510820000 |
| C | -0.020713000 | -2.894925000 | -0.277498000 |
| C | -0.295382000 | -2.525182000 | 1.074706000 |
| C | -1.637762000 | -2.045125000 | 1.137102000 |
| C | -2.189305000 | -2.113662000 | -0.179941000 |
| C | -1.190084000 | -2.643659000 | -1.052096000 |
| C | 1.236771000 | -3.558430000 | -0.776531000 |
| H | 1.432151000 | -3.320489000 | -1.827160000 |
| H | 2.118787000 | -3.256311000 | -0.201741000 |
| H | 1.171376000 | -4.653207000 | -0.703929000 |
| C | 0.614502000 | -2.744397000 | 2.256762000 |
| H | 1.673255000 | -2.692995000 | 1.979334000 |
| H | 0.444566000 | -2.009030000 | 3.052442000 |
| H | 0.458551000 | -3.733393000 | 2.710439000 |
| C | -2.388857000 | -1.708727000 | 2.399431000 |
| H | -2.823744000 | -2.608006000 | 2.858324000 |
| H | -1.744914000 | -1.248698000 | 3.157231000 |
| H | -3.217629000 | -1.018042000 | 2.215124000 |
| C | -3.626435000 | -1.855123000 | -0.555903000 |
| H | -4.221440000 | -2.778504000 | -0.519081000 |
| H | -4.108151000 | -1.140666000 | 0.118325000 |
| H | -3.722731000 | -1.461319000 | -1.573854000 |
| C | -1.396967000 | -3.028829000 | -2.494082000 |
| H | -2.117212000 | -2.373945000 | -2.993082000 |
| H | -0.468362000 | -2.974854000 | -3.067901000 |
| H | -1.780326000 | -4.056142000 | -2.578933000 |
| C | 5.301757000 | -0.137084000 | -0.034655000 |
| C | 4.609946000 | -0.139659000 | 1.176897000 |
| C | 3.218354000 | -0.104794000 | 1.150067000 |
| N | 2.509037000 | -0.070724000 | 0.007953000 |
| C | 3.182680000 | -0.069391000 | -1.159745000 |
| C | 4.574540000 | -0.101071000 | -1.223560000 |
| H | 6.387291000 | -0.162672000 | -0.050467000 |
| H | 5.133265000 | -0.167006000 | 2.126692000 |
| H | 2.645558000 | -0.104013000 | 2.073286000 |
| H | 2.568529000 | -0.042453000 | -2.058214000 |
| H | 5.069460000 | -0.097709000 | -2.188781000 |

FIG. 39I

Structure XI

|   |   |   |   |
|---|---:|---:|---:|
| C | 1.540366000 | -2.421900000 | 1.258425000 |
| C | 1.202368000 | -1.458791000 | 2.254679000 |
| C | -0.744252000 | -2.409314000 | 1.480930000 |
| C | -0.212449000 | -1.456036000 | 2.390670000 |
| C | 0.335164000 | -3.008463000 | 0.786373000 |
| La | 0.345688000 | -0.311573000 | -0.239722000 |
| H | 0.113852000 | -1.666176000 | -1.952945000 |
| C | 0.240341000 | -4.164729000 | -0.156679000 |
| H | 1.055669000 | -4.157142000 | -0.889115000 |
| H | 0.283844000 | -5.125137000 | 0.380383000 |
| H | -0.694672000 | -4.145812000 | -0.729127000 |
| C | -2.177334000 | -2.827836000 | 1.397670000 |
| H | -2.483279000 | -3.069466000 | 0.370284000 |

| | | | |
|---|---|---|---|
| H | -2.371755000 | -3.725069000 | 2.004195000 |
| H | -2.852775000 | -2.045064000 | 1.767400000 |
| C | 2.909563000 | -2.898039000 | 0.885241000 |
| H | 3.693738000 | -2.204916000 | 1.212627000 |
| H | 3.130916000 | -3.871816000 | 1.346307000 |
| C | 2.160403000 | -0.698157000 | 3.120294000 |
| H | 2.139549000 | -1.052817000 | 4.160933000 |
| H | 3.192483000 | -0.804653000 | 2.767030000 |
| H | 1.954666000 | 0.384180000 | 3.155202000 |
| C | -0.988565000 | -0.749190000 | 3.458582000 |
| H | -1.853716000 | -0.184070000 | 3.080460000 |
| H | -1.385881000 | -1.461242000 | 4.196744000 |
| H | -0.356527000 | -0.045702000 | 4.015330000 |
| H | 3.023372000 | -3.033067000 | -0.199341000 |
| C | 1.268507000 | 1.973062000 | -1.778478000 |
| C | 2.062261000 | 2.006452000 | -0.599277000 |
| C | 2.937036000 | 0.885286000 | -0.632468000 |
| C | 2.678486000 | 0.158219000 | -1.827688000 |
| C | 1.645170000 | 0.830677000 | -2.530647000 |
| C | 0.315891000 | 3.018817000 | -2.266208000 |
| H | -0.603929000 | 2.582289000 | -2.685302000 |
| H | 0.020014000 | 3.717186000 | -1.473774000 |
| H | 0.761912000 | 3.621281000 | -3.071366000 |
| C | 2.132235000 | 3.105337000 | 0.413082000 |
| H | 1.275026000 | 3.787379000 | 0.345029000 |
| H | 2.167194000 | 2.729749000 | 1.447911000 |
| H | 3.036772000 | 3.717649000 | 0.280730000 |
| C | 4.049921000 | 0.659645000 | 0.340861000 |
| H | 4.927328000 | 1.278750000 | 0.100357000 |
| H | 3.754876000 | 0.916365000 | 1.367506000 |
| H | 4.388892000 | -0.383500000 | 0.351667000 |
| C | 3.412785000 | -1.048298000 | -2.321151000 |
| H | 4.017098000 | -0.816581000 | -3.209838000 |
| H | 4.098790000 | -1.443090000 | -1.562428000 |
| H | 2.723655000 | -1.858174000 | -2.599628000 |
| C | 1.123195000 | 0.488213000 | -3.889153000 |
| H | 1.333684000 | -0.554978000 | -4.146179000 |
| H | 0.033573000 | 0.618834000 | -3.957491000 |
| H | 1.569886000 | 1.127747000 | -4.666444000 |
| C | -1.767795000 | 4.391746000 | 1.884114000 |
| C | -0.929269000 | 3.549586000 | 2.603189000 |
| C | -0.608754000 | 2.312822000 | 2.058078000 |
| N | -1.069757000 | 1.885205000 | 0.876644000 |
| C | -1.882617000 | 2.704633000 | 0.196323000 |
| C | -2.255675000 | 3.960720000 | 0.655608000 |
| H | -2.037608000 | 5.370116000 | 2.274135000 |
| H | -0.522197000 | 3.841014000 | 3.566781000 |
| H | 0.052155000 | 1.627142000 | 2.588860000 |
| H | -2.245930000 | 2.332778000 | -0.761940000 |
| H | -2.911765000 | 4.584949000 | 0.055963000 |
| C | -4.971380000 | -1.330297000 | -1.641880000 |
| C | -4.726722000 | -0.599880000 | -0.484929000 |
| C | -3.428364000 | -0.179054000 | -0.231583000 |
| N | -2.393265000 | -0.440431000 | -1.041389000 |
| C | -2.641166000 | -1.146508000 | -2.157018000 |
| C | -3.910043000 | -1.604556000 | -2.494085000 |
| H | -5.974152000 | -1.682556000 | -1.872523000 |

FIG. 39J

|   |   |   |   |
|---|---|---|---|
| H | -5.521615000 | -0.365632000 | 0.217389000 |
| H | -3.199147000 | 0.387540000 | 0.671675000 |
| H | -1.761406000 | -1.373364000 | -2.760013000 |
| H | -4.051474000 | -2.173662000 | -3.408329000 |

TS3

|   |   |   |   |
|---|---|---|---|
| C | 1.551599000 | -1.369779000 | 2.199783000 |
| C | 2.590671000 | -0.878274000 | 1.366680000 |
| C | 1.479461000 | 0.933346000 | 2.249601000 |
| C | 2.551984000 | 0.545221000 | 1.406330000 |
| C | 0.852678000 | -0.251378000 | 2.732618000 |
| La | 0.240059000 | -0.206357000 | -0.106434000 |
| C | -0.164065000 | -0.329061000 | 3.827741000 |
| H | -0.863658000 | -1.168439000 | 3.695838000 |
| H | 0.313002000 | -0.482673000 | 4.807576000 |
| H | -0.756519000 | 0.591151000 | 3.910949000 |
| C | 1.138718000 | 2.329789000 | 2.668316000 |
| H | 0.059671000 | 2.463536000 | 2.829263000 |
| H | 1.634224000 | 2.603340000 | 3.611080000 |
| H | 1.447593000 | 3.066148000 | 1.915701000 |
| C | 1.350170000 | -2.781348000 | 2.649477000 |
| H | 1.809171000 | -3.504752000 | 1.965651000 |
| H | 1.802167000 | -2.946102000 | 3.639053000 |
| C | 3.641006000 | -1.681377000 | 0.665300000 |
| H | 4.630872000 | -1.533212000 | 1.121157000 |
| H | 3.424422000 | -2.755279000 | 0.707840000 |
| H | 3.738302000 | -1.406798000 | -0.395239000 |
| C | 3.570082000 | 1.436490000 | 0.767689000 |
| H | 3.253933000 | 2.485977000 | 0.770435000 |
| H | 4.531154000 | 1.379609000 | 1.300295000 |
| H | 3.760298000 | 1.164869000 | -0.279302000 |
| H | 0.288539000 | -3.045324000 | 2.744148000 |
| C | -1.250682000 | -1.281848000 | -2.348106000 |
| C | -0.026143000 | -2.000710000 | -2.328691000 |
| C | -0.021238000 | -2.831656000 | -1.172439000 |
| C | -1.248733000 | -2.627149000 | -0.479497000 |
| C | -2.005993000 | -1.674233000 | -1.211546000 |
| C | -1.734856000 | -0.350724000 | -3.416811000 |
| H | -1.998238000 | 0.645165000 | -3.029226000 |
| H | -0.976571000 | -0.200027000 | -4.194201000 |
| H | -2.630325000 | -0.744496000 | -3.918006000 |
| C | 1.016607000 | -2.032682000 | -3.401228000 |
| H | 1.032390000 | -1.111127000 | -3.995774000 |
| H | 2.025111000 | -2.162194000 | -2.989290000 |
| H | 0.844602000 | -2.864038000 | -4.100895000 |
| C | 1.017963000 | -3.870496000 | -0.887282000 |
| H | 0.886407000 | -4.752688000 | -1.530837000 |
| H | 2.036674000 | -3.500530000 | -1.068233000 |
| H | 0.979932000 | -4.221364000 | 0.150461000 |
| C | -1.747401000 | -3.374941000 | 0.718736000 |
| H | -2.615974000 | -4.000847000 | 0.468584000 |
| H | -0.981430000 | -4.041529000 | 1.129960000 |
| H | -2.070940000 | -2.711559000 | 1.537311000 |
| C | -3.432893000 | -1.312643000 | -0.949783000 |
| H | -3.692689000 | -1.387276000 | 0.114486000 |
| H | -3.673693000 | -0.292652000 | -1.277851000 |

FIG. 39K

| | | | |
|---|---:|---:|---:|
| H | -4.115687000 | -1.986392000 | -1.489042000 |
| C | 2.471919000 | 3.680795000 | -1.898422000 |
| C | 2.274919000 | 2.558218000 | -2.645084000 |
| C | 1.175599000 | 1.684243000 | -2.332859000 |
| N | 0.196235000 | 2.094626000 | -1.447634000 |
| C | 0.470730000 | 3.187167000 | -0.696622000 |
| C | 1.564560000 | 4.002280000 | -0.857306000 |
| H | 3.308423000 | 4.342412000 | -2.115819000 |
| H | 2.949750000 | 2.283954000 | -3.451713000 |
| H | 1.860062000 | 0.346659000 | -1.627183000 |
| H | 1.685817000 | 4.891798000 | -0.246134000 |
| H | 0.812347000 | 1.040201000 | -3.136159000 |
| H | -0.285764000 | 3.434065000 | 0.054115000 |
| C | -4.654572000 | 2.057590000 | 1.172053000 |
| C | -4.056829000 | 1.141374000 | 2.029288000 |
| C | -2.771426000 | 0.703648000 | 1.738428000 |
| N | -2.075806000 | 1.123728000 | 0.674373000 |
| C | -2.663832000 | 2.001206000 | -0.151857000 |
| C | -3.945104000 | 2.494768000 | 0.060479000 |
| H | -5.660645000 | 2.421737000 | 1.365661000 |
| H | -4.572897000 | 0.765835000 | 2.907962000 |
| H | -2.274327000 | -0.019756000 | 2.385293000 |
| H | -2.067699000 | 2.294644000 | -1.017423000 |
| H | -4.373595000 | 3.204824000 | -0.640855000 |

Structure XII

| | | | |
|---|---:|---:|---:|
| C | -0.457968000 | -1.524517000 | -2.494011000 |
| C | -1.618825000 | -1.864328000 | -1.747237000 |
| C | -1.725129000 | 0.385225000 | -2.229072000 |
| C | -2.399224000 | -0.681744000 | -1.584559000 |
| C | -0.525896000 | -0.133283000 | -2.790745000 |
| La | -0.159351000 | -0.230309000 | 0.075356000 |
| C | 0.372259000 | 0.620322000 | -3.720013000 |
| H | 1.330260000 | 0.109416000 | -3.880421000 |
| H | -0.090986000 | 0.728533000 | -4.711361000 |
| H | 0.591271000 | 1.637643000 | -3.367669000 |
| C | -2.205768000 | 1.794968000 | -2.363013000 |
| H | -1.366790000 | 2.503484000 | -2.414794000 |
| H | -2.797931000 | 1.937183000 | -3.278840000 |
| H | -2.827558000 | 2.104301000 | -1.513720000 |
| C | 0.575800000 | -2.474324000 | -3.013782000 |
| H | 0.668410000 | -3.367741000 | -2.383242000 |
| H | 0.335612000 | -2.825125000 | -4.027826000 |
| C | -2.070775000 | -3.235624000 | -1.353671000 |
| H | -2.919555000 | -3.563272000 | -1.970784000 |
| H | -1.277061000 | -3.980588000 | -1.473468000 |
| H | -2.411342000 | -3.289849000 | -0.308616000 |
| C | -3.744206000 | -0.617654000 | -0.932438000 |
| H | -3.929225000 | 0.356682000 | -0.460915000 |
| H | -4.550806000 | -0.789743000 | -1.659708000 |
| H | -3.859207000 | -1.383646000 | -0.151913000 |
| H | 1.574572000 | -2.017776000 | -3.071552000 |
| C | 0.990665000 | -0.870992000 | 2.632934000 |
| C | 0.236830000 | -2.017516000 | 2.256444000 |
| C | 0.924112000 | -2.663568000 | 1.188945000 |
| C | 2.085154000 | -1.904809000 | 0.889649000 |

FIG. 39L

| | | | |
|---|---:|---:|---:|
| C | 2.129969000 | -0.803160000 | 1.788826000 |
| C | 0.709382000 | 0.071868000 | 3.762303000 |
| H | 0.674966000 | 1.122465000 | 3.438122000 |
| H | -0.253460000 | -0.141109000 | 4.240173000 |
| H | 1.479028000 | 0.000532000 | 4.543734000 |
| C | -0.997411000 | -2.549410000 | 2.918953000 |
| H | -1.467537000 | -1.804091000 | 3.571016000 |
| H | -1.760799000 | -2.868852000 | 2.192267000 |
| H | -0.777051000 | -3.428533000 | 3.541096000 |
| C | 0.617539000 | -4.026413000 | 0.657581000 |
| H | 1.168432000 | -4.797957000 | 1.215923000 |
| H | -0.446723000 | -4.274163000 | 0.741747000 |
| H | 0.901840000 | -4.140935000 | -0.396974000 |
| C | 3.142975000 | -2.296565000 | -0.093764000 |
| H | 3.847859000 | -3.026560000 | 0.330670000 |
| H | 2.717015000 | -2.759209000 | -0.995513000 |
| H | 3.742984000 | -1.435357000 | -0.416908000 |
| C | 3.258028000 | 0.163674000 | 1.955524000 |
| H | 3.809584000 | 0.331079000 | 1.020778000 |
| H | 2.910541000 | 1.142485000 | 2.312196000 |
| H | 3.986612000 | -0.199391000 | 2.694859000 |
| C | -3.795011000 | 2.836929000 | 1.379225000 |
| C | -3.579557000 | 1.576527000 | 1.805058000 |
| C | -2.163124000 | 1.128580000 | 2.016770000 |
| N | -1.201498000 | 1.764660000 | 1.108389000 |
| C | -1.495675000 | 3.041894000 | 0.762363000 |
| C | -2.695280000 | 3.667501000 | 0.962976000 |
| H | -4.813258000 | 3.212203000 | 1.277797000 |
| H | -4.395427000 | 0.899126000 | 2.050508000 |
| H | -2.108936000 | 0.013929000 | 1.887445000 |
| H | -2.848710000 | 4.690076000 | 0.633618000 |
| H | -1.843287000 | 1.272273000 | 3.073473000 |
| H | -0.707217000 | 3.566219000 | 0.209147000 |
| C | 3.973410000 | 3.214379000 | -0.879632000 |
| C | 2.983537000 | 3.493185000 | 0.053926000 |
| C | 1.917595000 | 2.611480000 | 0.179704000 |
| N | 1.795792000 | 1.509387000 | -0.574925000 |
| C | 2.759129000 | 1.245378000 | -1.468528000 |
| C | 3.864118000 | 2.063659000 | -1.653025000 |
| H | 4.822684000 | 3.882205000 | -1.000509000 |
| H | 3.031244000 | 4.375954000 | 0.684327000 |
| H | 1.128988000 | 2.769665000 | 0.917348000 |
| H | 2.635865000 | 0.335893000 | -2.058022000 |
| H | 4.618100000 | 1.801849000 | -2.389137000 |

FIG. 39M

Structure XII

| | | | |
|---|---:|---:|---:|
| C | 2.174012000 | -2.104904000 | -1.829136000 |
| C | 1.240032000 | -2.988514000 | -1.228303000 |
| C | 0.066393000 | -1.510301000 | -2.546156000 |
| C | -0.060680000 | -2.614562000 | -1.656671000 |
| C | 1.447169000 | -1.192722000 | -2.650962000 |
| La | 0.742548000 | -0.410972000 | 0.053193000 |
| C | 2.037158000 | -0.190849000 | -3.594778000 |
| H | 2.980910000 | 0.233909000 | -3.228404000 |
| H | 2.247478000 | -0.638875000 | -4.576660000 |
| H | 1.360254000 | 0.654078000 | -3.774415000 |

| | | | |
|---|---:|---:|---:|
| C | -1.039417000 | -0.922794000 | -3.367529000 |
| H | -0.819199000 | 0.104126000 | -3.682383000 |
| H | -1.201583000 | -1.507774000 | -4.284916000 |
| H | -1.993635000 | -0.898835000 | -2.826074000 |
| C | 3.664925000 | -2.251878000 | -1.758357000 |
| H | 4.082680000 | -2.097914000 | -0.748905000 |
| H | 3.981198000 | -3.258428000 | -2.065057000 |
| C | 1.567666000 | -4.248879000 | -0.494028000 |
| H | 1.448431000 | -5.123202000 | -1.151624000 |
| H | 2.601419000 | -4.255150000 | -0.131536000 |
| H | 0.913449000 | -4.423100000 | 0.371154000 |
| C | -1.302721000 | -3.405289000 | -1.384984000 |
| H | -2.211353000 | -2.836227000 | -1.611963000 |
| H | -1.326759000 | -4.320632000 | -1.995163000 |
| H | -1.369249000 | -3.728221000 | -0.335776000 |
| H | 4.168217000 | -1.549007000 | -2.433658000 |
| C | 0.245846000 | -0.270735000 | 2.907794000 |
| C | 0.678005000 | -1.603363000 | 2.641280000 |
| C | 2.065714000 | -1.556472000 | 2.332707000 |
| C | 2.476093000 | -0.196986000 | 2.365653000 |
| C | 1.350202000 | 0.597788000 | 2.725523000 |
| C | -1.074925000 | 0.099158000 | 3.506864000 |
| H | -1.171537000 | 1.185284000 | 3.618888000 |
| H | -1.942894000 | -0.243969000 | 2.930887000 |
| H | -1.172483000 | -0.333325000 | 4.513783000 |
| C | -0.157085000 | -2.825451000 | 2.866347000 |
| H | -1.189471000 | -2.694209000 | 2.513416000 |
| H | 0.251671000 | -3.707162000 | 2.357609000 |
| H | -0.223505000 | -3.076990000 | 3.935364000 |
| C | 3.004550000 | -2.714229000 | 2.213426000 |
| H | 3.641340000 | -2.790399000 | 3.107195000 |
| H | 2.475242000 | -3.667446000 | 2.113836000 |
| H | 3.686952000 | -2.628484000 | 1.355107000 |
| C | 3.897401000 | 0.257917000 | 2.262492000 |
| H | 4.443395000 | 0.064476000 | 3.197930000 |
| H | 4.451895000 | -0.265986000 | 1.470157000 |
| H | 3.981380000 | 1.333827000 | 2.062554000 |
| C | 1.358006000 | 2.071307000 | 2.988132000 |
| H | 2.210388000 | 2.562906000 | 2.502184000 |
| H | 0.449271000 | 2.570280000 | 2.622379000 |
| H | 1.435446000 | 2.290420000 | 4.062631000 |
| C | -1.226532000 | 4.298814000 | -0.605523000 |
| C | -0.635180000 | 3.637141000 | -1.618205000 |
| C | -0.741445000 | 2.135530000 | -1.662091000 |
| N | -0.797595000 | 1.517900000 | -0.324589000 |
| C | -1.465215000 | 2.244117000 | 0.610418000 |
| C | -1.796635000 | 3.569787000 | 0.503267000 |
| H | -1.212366000 | 5.388512000 | -0.576260000 |
| H | -0.123509000 | 4.157200000 | -2.426794000 |
| H | 0.119228000 | 1.711043000 | -2.211276000 |
| H | -2.300853000 | 4.077252000 | 1.320565000 |
| H | -1.629364000 | 1.830443000 | -2.256859000 |
| H | -1.698081000 | 1.712328000 | 1.537627000 |
| H | -1.792924000 | -1.286189000 | 0.455085000 |
| B | -2.853610000 | -0.762258000 | 0.262959000 |
| O | -3.517061000 | -0.844991000 | -0.919777000 |
| O | -3.536860000 | -0.130406000 | 1.250905000 |

FIG. 39N

|     |              |              |              |
| --- | ------------ | ------------ | ------------ |
| C   | -4.864731000 |  0.145245000 |  0.740444000 |
| C   | -4.674889000 |  0.023960000 | -0.808699000 |
| C   | -5.829883000 | -0.628562000 | -1.539492000 |
| C   | -4.311693000 |  1.336579000 | -1.484075000 |
| H   | -3.496458000 |  1.860507000 | -0.970135000 |
| H   | -3.986384000 |  1.120608000 | -2.509121000 |
| H   | -5.177553000 |  2.007247000 | -1.535736000 |
| H   | -5.599953000 | -0.681543000 | -2.609089000 |
| H   | -4.530525000 |  2.275168000 |  0.982572000 |
| C   | -5.285841000 |  1.518537000 |  1.220344000 |
| H   | -5.421418000 |  1.500773000 |  2.307360000 |
| H   | -6.240668000 |  1.809563000 |  0.764247000 |
| H   | -6.744961000 | -0.034941000 | -1.418653000 |
| H   | -6.823338000 | -0.752377000 |  1.061038000 |
| C   | -5.773609000 | -0.924191000 |  1.325493000 |
| H   | -5.685983000 | -0.900078000 |  2.416778000 |
| H   | -5.485339000 | -1.925449000 |  0.984976000 |
| H   | -6.021262000 | -1.644386000 | -1.182237000 |
| C   |  4.470205000 |  3.560982000 | -0.751040000 |
| C   |  3.160965000 |  3.819366000 | -0.368048000 |
| C   |  2.272796000 |  2.756698000 | -0.258100000 |
| N   |  2.622823000 |  1.485812000 | -0.513710000 |
| C   |  3.889739000 |  1.248475000 | -0.884524000 |
| C   |  4.842769000 |  2.247535000 | -1.016416000 |
| H   |  5.191807000 |  4.369088000 | -0.844238000 |
| H   |  2.814242000 |  4.827090000 | -0.158369000 |
| H   |  1.234499000 |  2.926400000 |  0.028237000 |
| H   |  4.149641000 |  0.207138000 | -1.075628000 |
| H   |  5.854757000 |  1.994970000 | -1.318744000 |

| | | | |
|---|---:|---:|---:|
| C | 0.321858000 | -0.404947000 | 2.920916000 |
| C | 0.833834000 | -1.692989000 | 2.588296000 |
| C | 2.206480000 | -1.541647000 | 2.247222000 |
| C | 2.523611000 | -0.157742000 | 2.314811000 |
| C | 1.361039000 | 0.542547000 | 2.746662000 |
| C | -1.005768000 | -0.157923000 | 3.567518000 |
| H | -1.154149000 | 0.907730000 | 3.777947000 |
| H | -1.863224000 | -0.492785000 | 2.970921000 |
| H | -1.061857000 | -0.680384000 | 4.533829000 |
| C | 0.073884000 | -2.972668000 | 2.755989000 |
| H | -0.967926000 | -2.875762000 | 2.419632000 |
| H | 0.523464000 | -3.801340000 | 2.193812000 |
| H | 0.034608000 | -3.286542000 | 3.809711000 |
| C | 3.223386000 | -2.626839000 | 2.090767000 |
| H | 3.864921000 | -2.679302000 | 2.982804000 |
| H | 2.762750000 | -3.612378000 | 1.969097000 |
| H | 3.896375000 | -2.469975000 | 1.235875000 |
| C | 3.901115000 | 0.402518000 | 2.152600000 |
| H | 4.517643000 | 0.215892000 | 3.044441000 |
| H | 4.438867000 | -0.050951000 | 1.306414000 |
| H | 3.893801000 | 1.487603000 | 1.989703000 |
| C | 1.290055000 | 1.996238000 | 3.097351000 |
| H | 2.079535000 | 2.573595000 | 2.599906000 |
| H | 0.332940000 | 2.455465000 | 2.814050000 |
| H | 1.416031000 | 2.153271000 | 4.178045000 |
| C | -1.512101000 | 4.044800000 | -0.607732000 |
| C | -1.149557000 | 3.280698000 | -1.652418000 |
| C | -1.124357000 | 1.779480000 | -1.548632000 |
| N | -1.142166000 | 1.255378000 | -0.166333000 |
| C | -1.569130000 | 2.104344000 | 0.811687000 |
| C | -1.797342000 | 3.443429000 | 0.676596000 |
| H | -1.560160000 | 5.128215000 | -0.716321000 |
| H | -0.907601000 | 3.722062000 | -2.618383000 |
| H | -0.219575000 | 1.396208000 | -2.068596000 |
| H | -2.125958000 | 4.035672000 | 1.525003000 |
| H | -1.957174000 | 1.330433000 | -2.125831000 |
| H | -1.716439000 | 1.631444000 | 1.785602000 |
| H | -1.609218000 | -1.349781000 | 0.160028000 |
| B | -2.586558000 | -0.646410000 | 0.072272000 |
| O | -3.318414000 | -0.598789000 | -1.086920000 |
| O | -3.312466000 | -0.321516000 | 1.190488000 |
| C | -4.685828000 | -0.172343000 | 0.782615000 |
| C | -4.578409000 | 0.036721000 | -0.766475000 |
| C | -5.665666000 | -0.647768000 | -1.571656000 |
| C | -4.497323000 | 1.500391000 | -1.172671000 |
| H | -3.744724000 | 2.052202000 | -0.599633000 |
| H | -4.229964000 | 1.558049000 | -2.234298000 |
| H | -5.466980000 | 1.995862000 | -1.042472000 |
| H | -5.508249000 | -0.450244000 | -2.637648000 |
| H | -4.689800000 | 1.902912000 | 1.411015000 |
| C | -5.288625000 | 0.995193000 | 1.537870000 |
| H | -5.325701000 | 0.757545000 | 2.606906000 |
| H | -6.313717000 | 1.192368000 | 1.198344000 |
| H | -6.653681000 | -0.256765000 | -1.296538000 |
| H | -6.462417000 | -1.430533000 | 0.957381000 |
| C | -5.387498000 | -1.466546000 | 1.169364000 |
| H | -5.254034000 | -1.629069000 | 2.244317000 |

FIG. 39P

| | | | |
|---|---:|---:|---:|
| H | -4.953764000 | -2.324846000 | 0.643010000 |
| H | -5.663077000 | -1.731218000 | -1.424325000 |
| C | 3.833512000 | 4.056667000 | -0.692302000 |
| C | 4.356239000 | 2.823370000 | -1.069503000 |
| C | 3.556017000 | 1.698411000 | -0.940841000 |
| N | 2.302758000 | 1.742170000 | -0.465635000 |
| C | 1.803816000 | 2.936049000 | -0.107966000 |
| C | 2.534195000 | 4.114118000 | -0.207887000 |
| H | 4.433157000 | 4.959697000 | -0.777850000 |
| H | 5.366228000 | 2.729975000 | -1.457352000 |
| H | 3.929129000 | 0.714178000 | -1.226891000 |
| H | 0.783398000 | 2.952737000 | 0.275736000 |
| H | 2.075250000 | 5.052411000 | 0.090224000 |

Structure XIV

| | | | |
|---|---:|---:|---:|
| C | -1.820120000 | 2.330675000 | -1.650076000 |
| C | -0.710627000 | 2.991780000 | -1.042838000 |
| C | 0.116836000 | 1.456487000 | -2.538158000 |
| C | 0.480535000 | 2.446522000 | -1.587954000 |
| C | -1.302872000 | 1.382828000 | -2.577053000 |
| La | -0.604770000 | 0.347232000 | 0.041371000 |
| C | -2.070080000 | 0.543454000 | -3.552250000 |
| H | -3.147136000 | 0.743415000 | -3.509140000 |
| H | -1.747501000 | 0.751727000 | -4.581339000 |
| H | -1.937543000 | -0.537517000 | -3.393390000 |
| C | 1.047201000 | 0.832071000 | -3.529341000 |
| H | 0.671341000 | -0.126100000 | -3.912473000 |
| H | 1.173356000 | 1.489032000 | -4.403183000 |
| H | 2.043247000 | 0.663090000 | -3.101601000 |
| C | -3.254374000 | 2.732114000 | -1.474190000 |
| H | -3.694955000 | 2.432590000 | -0.508885000 |
| H | -3.367629000 | 3.822407000 | -1.535725000 |
| C | -0.764177000 | 4.263668000 | -0.256093000 |
| H | -0.476321000 | 5.114303000 | -0.891565000 |
| H | -1.768158000 | 4.471426000 | 0.127241000 |
| H | -0.076070000 | 4.272762000 | 0.599688000 |
| C | 1.859403000 | 2.963262000 | -1.331139000 |
| H | 2.614247000 | 2.177801000 | -1.458850000 |
| H | 2.105440000 | 3.789611000 | -2.014973000 |
| H | 1.956866000 | 3.353766000 | -0.309119000 |
| H | -3.888615000 | 2.310744000 | -2.264319000 |
| C | -0.170090000 | -0.003665000 | 2.890761000 |
| C | -0.341212000 | 1.392029000 | 2.663798000 |
| C | -1.713347000 | 1.618733000 | 2.358735000 |
| C | -2.373938000 | 0.360767000 | 2.348744000 |
| C | -1.421148000 | -0.640328000 | 2.691622000 |
| C | 1.058898000 | -0.626709000 | 3.474341000 |
| H | 0.937058000 | -1.710447000 | 3.592035000 |
| H | 1.964987000 | -0.461661000 | 2.876648000 |
| H | 1.250207000 | -0.220052000 | 4.478495000 |
| C | 0.722458000 | 2.416924000 | 2.906149000 |
| H | 1.694099000 | 2.097054000 | 2.505293000 |
| H | 0.481601000 | 3.384731000 | 2.449609000 |
| H | 0.867426000 | 2.598594000 | 3.981541000 |
| C | -2.426568000 | 2.933178000 | 2.324206000 |
| H | -3.065982000 | 3.042752000 | 3.212481000 |
| H | -1.731083000 | 3.777844000 | 2.326067000 |

FIG. 39Q

| | | | |
|---|---|---|---|
| H | −3.084620000 | 3.051458000 | 1.451569000 |
| C | −3.854100000 | 0.191299000 | 2.215510000 |
| H | −4.375511000 | 0.494559000 | 3.135518000 |
| H | −4.275058000 | 0.804802000 | 1.404780000 |
| H | −4.138253000 | −0.849300000 | 2.015171000 |
| C | −1.711723000 | −2.080441000 | 2.978970000 |
| H | −2.704193000 | −2.375535000 | 2.617204000 |
| H | −0.980789000 | −2.762023000 | 2.520188000 |
| H | −1.695691000 | −2.278859000 | 4.059894000 |
| C | −0.142600000 | −3.805887000 | −1.160280000 |
| C | 0.279669000 | −2.942990000 | −2.103373000 |
| C | 1.485670000 | −2.116758000 | −1.772605000 |
| N | 1.384701000 | −1.604528000 | −0.396909000 |
| C | 1.124773000 | −2.617357000 | 0.510611000 |
| C | 0.438027000 | −3.740780000 | 0.166298000 |
| H | −0.956681000 | −4.504428000 | −1.355815000 |
| H | −0.151696000 | −2.910399000 | −3.102459000 |
| H | 1.629112000 | −1.276049000 | −2.450356000 |
| H | 0.240205000 | −4.507160000 | 0.910706000 |
| H | 2.399441000 | −2.741686000 | −1.853956000 |
| H | 1.462953000 | −2.434766000 | 1.530634000 |
| H | 1.724130000 | 0.536332000 | 0.393882000 |
| B | 2.426711000 | −0.473127000 | 0.020877000 |
| O | 3.271325000 | −0.058618000 | −1.072292000 |
| O | 3.285305000 | −0.908370000 | 1.092912000 |
| C | 4.557005000 | −0.328462000 | 0.844265000 |
| C | 4.619360000 | −0.343449000 | −0.711049000 |
| C | 5.525245000 | 0.708025000 | −1.323618000 |
| C | 4.990676000 | −1.719629000 | −1.255232000 |
| H | 4.389235000 | −2.503598000 | −0.778395000 |
| H | 4.787598000 | −1.739444000 | −2.332867000 |
| H | 6.052183000 | −1.952521000 | −1.102792000 |
| H | 5.508136000 | 0.618593000 | −2.416457000 |
| H | 5.533438000 | −2.218421000 | 1.276914000 |
| C | 5.621921000 | −1.159080000 | 1.534604000 |
| H | 5.512289000 | −1.067793000 | 2.621650000 |
| H | 6.627885000 | −0.810821000 | 1.265274000 |
| H | 6.562969000 | 0.576094000 | −0.989571000 |
| H | 5.562635000 | 1.553377000 | 1.350996000 |
| C | 4.570282000 | 1.089400000 | 1.413183000 |
| H | 4.280589000 | 1.041522000 | 2.470664000 |
| H | 3.851668000 | 1.732386000 | 0.891073000 |
| H | 5.199816000 | 1.720689000 | −1.065421000 |
| C | −5.127959000 | −2.794346000 | −0.738450000 |
| C | −5.152116000 | −1.477985000 | −1.182302000 |
| C | −3.995509000 | −0.718052000 | −1.074399000 |
| N | −2.848445000 | −1.189851000 | −0.567087000 |
| C | −2.840104000 | −2.458948000 | −0.136001000 |
| C | −3.947764000 | −3.293745000 | −0.201704000 |
| H | −6.015730000 | −3.418559000 | −0.804090000 |
| H | −6.051475000 | −1.038095000 | −1.602922000 |
| H | −3.988446000 | 0.320158000 | −1.399162000 |
| H | −1.902765000 | −2.822614000 | 0.285766000 |
| H | −3.875960000 | −4.313449000 | 0.166175000 |

TS1

| | | | |
|---|---|---|---|
| C | −2.623705000 | −0.233117000 | 2.229341000 |

FIG. 39R

| | | | |
|---|---|---|---|
| C  | -1.378012000 | -0.351746000 |  2.907354000 |
| C  | -1.499276000 |  1.756892000 |  1.997153000 |
| C  | -0.681129000 |  0.872468000 |  2.754745000 |
| C  | -2.697218000 |  1.071382000 |  1.662629000 |
| La | -0.692219000 | -0.297074000 |  0.139286000 |
| C  | -3.875689000 |  1.651416000 |  0.942609000 |
| H  | -4.285137000 |  0.969122000 |  0.181934000 |
| H  | -4.703497000 |  1.887017000 |  1.626928000 |
| H  | -3.613512000 |  2.586161000 |  0.429773000 |
| C  | -1.197663000 |  3.204136000 |  1.765159000 |
| H  | -1.613943000 |  3.585682000 |  0.823002000 |
| H  | -1.609500000 |  3.831150000 |  2.569455000 |
| H  | -0.116270000 |  3.395943000 |  1.745037000 |
| C  | -3.745172000 | -1.218220000 |  2.335338000 |
| H  | -3.426270000 | -2.251939000 |  2.139742000 |
| H  | -4.175864000 | -1.210901000 |  3.347682000 |
| C  | -0.969697000 | -1.540015000 |  3.717943000 |
| H  | -1.541402000 | -1.597218000 |  4.656621000 |
| H  | -1.137524000 | -2.484274000 |  3.182437000 |
| H  |  0.094471000 | -1.511029000 |  3.974181000 |
| C  |  0.664472000 |  1.218201000 |  3.309874000 |
| H  |  1.346667000 |  1.612976000 |  2.539977000 |
| H  |  0.598306000 |  1.981784000 |  4.098554000 |
| H  |  1.153853000 |  0.337815000 |  3.740404000 |
| H  | -4.558074000 | -0.990776000 |  1.636607000 |
| C  | -0.645707000 | -1.513667000 | -2.510394000 |
| C  | -0.322229000 | -2.555699000 | -1.599572000 |
| C  | -1.481904000 | -2.841414000 | -0.828817000 |
| C  | -2.527291000 | -1.980660000 | -1.269320000 |
| C  | -2.003067000 | -1.153170000 | -2.300160000 |
| C  |  0.223267000 | -0.999644000 | -3.615780000 |
| H  |  0.151165000 |  0.090571000 | -3.739935000 |
| H  |  1.280691000 | -1.236433000 | -3.447579000 |
| H  | -0.056012000 | -1.444858000 | -4.581904000 |
| C  |  0.959348000 | -3.326418000 | -1.549187000 |
| H  |  1.832469000 | -2.709620000 | -1.798507000 |
| H  |  1.135493000 | -3.739352000 | -0.549501000 |
| H  |  0.946489000 | -4.166863000 | -2.259567000 |
| C  | -1.580600000 | -3.911904000 |  0.213286000 |
| H  | -1.536484000 | -4.917337000 | -0.229306000 |
| H  | -0.762111000 | -3.847619000 |  0.944633000 |
| H  | -2.523881000 | -3.848952000 |  0.770634000 |
| C  | -3.981742000 | -2.075232000 | -0.932123000 |
| H  | -4.539359000 | -2.553561000 | -1.751096000 |
| H  | -4.161223000 | -2.671105000 | -0.031241000 |
| H  | -4.449459000 | -1.092675000 | -0.770924000 |
| C  | -2.819380000 | -0.245860000 | -3.164473000 |
| H  | -3.612054000 |  0.266633000 | -2.598050000 |
| H  | -2.206276000 |  0.521128000 | -3.656237000 |
| H  | -3.328383000 | -0.801651000 | -3.966793000 |
| C  | -0.379798000 |  4.739362000 | -2.085955000 |
| C  |  0.750814000 |  4.228397000 | -1.461381000 |
| C  |  0.729005000 |  2.914558000 | -1.010187000 |
| N  | -0.335634000 |  2.113884000 | -1.154372000 |
| C  | -1.422467000 |  2.616957000 | -1.755476000 |
| C  | -1.491135000 |  3.917749000 | -2.235771000 |
| H  | -0.397156000 |  5.764564000 | -2.447450000 |

FIG. 39S

| | | | |
|---|---:|---:|---:|
| H | 1.640182000 | 4.834795000 | -1.317799000 |
| H | 1.594280000 | 2.482730000 | -0.505447000 |
| H | -2.398991000 | 4.272640000 | -2.714493000 |
| H | 1.820076000 | 0.237806000 | -1.716680000 |
| H | -2.276341000 | 1.944789000 | -1.850206000 |
| H | 0.863299000 | -1.508019000 | 1.115772000 |
| B | 2.763949000 | 0.051330000 | -1.009895000 |
| O | 2.917323000 | 0.737217000 | 0.160258000 |
| O | 3.752991000 | -0.830574000 | -1.285740000 |
| C | 4.532646000 | -0.968238000 | -0.067623000 |
| C | 4.215848000 | 0.359929000 | 0.696676000 |
| C | 4.095284000 | 0.206671000 | 2.197183000 |
| C | 5.161485000 | 1.499108000 | 0.350107000 |
| H | 5.262722000 | 1.622348000 | -0.734557000 |
| H | 4.760294000 | 2.430759000 | 0.764080000 |
| H | 6.158137000 | 1.338078000 | 0.776565000 |
| H | 3.898539000 | 1.182956000 | 2.655491000 |
| H | 6.344489000 | -0.348334000 | -1.104931000 |
| C | 5.987474000 | -1.146898000 | -0.448404000 |
| H | 6.109080000 | -2.098393000 | -0.976679000 |
| H | 6.619054000 | -1.175833000 | 0.448567000 |
| H | 5.031548000 | -0.181279000 | 2.618585000 |
| H | 4.608168000 | -2.439103000 | 1.531220000 |
| C | 4.015289000 | -2.211256000 | 0.637446000 |
| H | 4.096799000 | -3.058484000 | -0.052779000 |
| H | 2.958974000 | -2.102868000 | 0.921970000 |
| H | 3.274865000 | -0.467125000 | 2.463109000 |

FIG. 39T

Structure VIII

| | | | |
|---|---:|---:|---:|
| C | -2.342890000 | -0.332209000 | -2.315936000 |
| C | -1.458916000 | 0.706375000 | -2.727497000 |
| C | -0.220795000 | -1.216903000 | -2.456023000 |
| C | -0.149156000 | 0.153847000 | -2.816229000 |
| C | -1.573705000 | -1.515229000 | -2.138424000 |
| La | -0.705303000 | 0.257436000 | -0.034873000 |
| C | -2.144056000 | -2.858748000 | -1.811866000 |
| H | -2.971493000 | -2.789206000 | -1.090258000 |
| H | -2.552059000 | -3.354999000 | -2.704713000 |
| H | -1.394737000 | -3.536501000 | -1.381395000 |
| C | 0.924085000 | -2.178466000 | -2.521168000 |
| H | 0.707488000 | -3.112932000 | -1.986797000 |
| H | 1.152526000 | -2.452675000 | -3.561117000 |
| H | 1.837367000 | -1.747414000 | -2.088406000 |
| C | -3.837998000 | -0.290995000 | -2.271804000 |
| H | -4.225302000 | 0.729595000 | -2.354644000 |
| H | -4.270866000 | -0.869108000 | -3.101194000 |
| C | -1.828176000 | 2.105073000 | -3.114454000 |
| H | -1.884434000 | 2.226099000 | -4.205550000 |
| H | -2.804066000 | 2.398867000 | -2.708411000 |
| H | -1.094669000 | 2.841321000 | -2.755004000 |
| C | 1.081330000 | 0.850578000 | -3.303296000 |
| H | 1.968524000 | 0.500613000 | -2.760731000 |
| H | 1.249208000 | 0.667815000 | -4.374767000 |
| H | 1.019525000 | 1.937852000 | -3.166773000 |
| H | -4.252224000 | -0.720021000 | -1.346598000 |
| C | -1.521442000 | 0.976674000 | 2.606333000 |
| C | -0.913559000 | 2.151340000 | 2.084052000 |

| | | | |
|---|---|---|---|
| C | -1.747340000 | 2.658280000 | 1.051236000 |
| C | -2.873185000 | 1.798098000 | 0.930394000 |
| C | -2.728448000 | 0.751726000 | 1.889046000 |
| C | -0.998457000 | 0.182456000 | 3.761883000 |
| H | -1.490739000 | -0.793477000 | 3.850545000 |
| H | 0.080758000 | -0.002239000 | 3.682450000 |
| H | -1.160073000 | 0.707907000 | 4.713527000 |
| C | 0.322205000 | 2.810210000 | 2.610422000 |
| H | 1.000929000 | 2.092619000 | 3.084374000 |
| H | 0.899238000 | 3.301816000 | 1.818090000 |
| H | 0.073847000 | 3.575623000 | 3.359925000 |
| C | -1.515051000 | 3.933749000 | 0.303764000 |
| H | -1.785091000 | 4.810662000 | 0.909365000 |
| H | -0.460343000 | 4.059921000 | 0.023030000 |
| H | -2.109701000 | 3.985069000 | -0.616553000 |
| C | -4.121182000 | 2.079074000 | 0.156034000 |
| H | -4.802511000 | 2.719486000 | 0.735159000 |
| H | -3.923221000 | 2.600958000 | -0.788702000 |
| H | -4.672649000 | 1.162851000 | -0.085544000 |
| C | -3.759285000 | -0.302331000 | 2.154274000 |
| H | -4.080147000 | -0.826623000 | 1.239021000 |
| H | -3.392924000 | -1.059389000 | 2.858699000 |
| H | -4.671739000 | 0.123257000 | 2.596000000 |
| C | 0.146294000 | -4.859002000 | 1.633455000 |
| C | 1.151434000 | -4.023368000 | 1.162231000 |
| C | 0.837322000 | -2.705342000 | 0.856583000 |
| N | -0.402843000 | -2.210310000 | 0.995731000 |
| C | -1.365426000 | -3.020692000 | 1.454764000 |
| C | -1.137705000 | -4.348206000 | 1.787009000 |
| H | 0.359970000 | -5.896559000 | 1.878669000 |
| H | 2.168842000 | -4.379768000 | 1.029050000 |
| H | 1.596786000 | -2.017310000 | 0.471889000 |
| H | -1.953195000 | -4.965058000 | 2.152467000 |
| H | 1.314251000 | 0.265794000 | 1.338018000 |
| H | -2.360332000 | -2.583180000 | 1.553384000 |
| H | 1.255046000 | 1.568671000 | -0.215524000 |
| B | 2.067361000 | 0.813497000 | 0.469759000 |
| O | 2.637027000 | -0.173297000 | -0.440931000 |
| O | 3.135135000 | 1.526679000 | 1.079905000 |
| C | 4.298506000 | 1.266245000 | 0.309213000 |
| C | 4.043935000 | -0.179836000 | -0.208806000 |
| C | 4.762596000 | -0.533558000 | -1.497079000 |
| C | 4.350500000 | -1.236472000 | 0.849957000 |
| H | 3.828471000 | -1.013013000 | 1.788543000 |
| H | 4.006796000 | -2.212512000 | 0.480752000 |
| H | 5.424485000 | -1.320125000 | 1.056844000 |
| H | 4.534021000 | -1.569666000 | -1.777869000 |
| H | 5.419819000 | 0.828079000 | 2.116350000 |
| C | 5.519506000 | 1.413809000 | 1.199623000 |
| H | 5.639951000 | 2.464638000 | 1.484692000 |
| H | 6.430895000 | 1.099888000 | 0.671532000 |
| H | 5.850874000 | -0.451990000 | -1.374300000 |
| H | 5.300868000 | 2.209081000 | -1.397486000 |
| C | 4.367313000 | 2.284765000 | -0.826062000 |
| H | 4.312490000 | 3.288407000 | -0.389570000 |
| H | 3.523125000 | 2.171489000 | -1.517019000 |
| H | 4.454931000 | 0.113518000 | -2.324165000 |

FIG. 39U

REGIOSELECTIVE 1,2-DEAROMATIZATION OF FUNCTIONALIZED AZINES BY ORGANOLANTHANIDE CATALYSTS

This application claims priority to and the benefit of application Ser. No. 62/088,301 filed Dec. 5, 2014—the entirety of which is incorporated herein by reference.

This invention was made with government support under CHE0923236, CHE1048773, CHE1213235, and CHE1464488 awarded by the National Science Foundation. The government has certain rights in the invention.

FIELD OF THE INVENTION

The present invention relates to a method for 1,2-regioselective organolanthanide-catalyzed azine dearomatization. The process uses main-group element hydrides, which is compatible with a broad range of azines and functional groups, and employs equimolar reagent stoichiometry.

BACKGROUND OF THE INVENTION

Over the past few decades, catalysts based on precious metals have dominated organic catalytic chemistry and enabled the expeditious synthesis and discovery of numerous valuable organic compounds including natural products, pharmaceuticals, and advanced materials. However, precious metals are not earth-abundant, are expensive, and are susceptible to supply fluctuations. For these reasons, there is a critical need to develop efficient, sustainable catalysts based on earth-abundant elements that can outperform/supplement traditional precious metal catalysts in high-value transformations and which may do so via unconventional reaction pathways (Bullock, R. M., *Catalysis Without Precious Metals* (Wiley, 2010); Bullock, R. M., *Science* 342, 1054-1055 (2013); National Research Council, *The Role of the Chemical Sciences in Finding Alternatives to Critical Resources: A Workshop Summary* (The National Academies Press, 2012); Eijsbouts, S. et al., *Appl. Catal. A* 458, 169-182 (2013); and Wender, P. et al., *Nature* 469, 23-25 (2011)).

The dearomatization of aromatic compounds is one example of an especially challenging processes, and among these, selective dearomatization of six-membered nitrogenous heterocycles is an important transformation that provides straightforward access to diverse structural motifs present in many naturally-occurring and pharmacologically-active molecules (FIG. 1a) (Pape, A. R. et al., *Chem. Rev.* 100, 2917-2940 (2000); Roche, S. P. et al., *Angew. Chem. Int. Ed.* 50, 4068-4093 (2011)). For example, vinblastine, vincristine, and codeine are on the World Health Organization's *List of Essential Medicines* and like many other heavily prescribed drugs (e.g., Plavix, Abilify) incorporate dearomatized azine rings. Various dihydropyridines have a widespread natural occurrence and are used to treat a broad spectrum of medical conditions, such as cardiovascular and Alzheimer's diseases, dementia, diabetic neuropathy, and multidrug-resistant cancers (Stout, D. M. et al., *Chem. Rev.* 82, 223-243 (1982); Edraki, N. et al., *Drug Discovery Today* 14, 1058-1066 (2009)). Note also that 1,2-dihydropyridines are particularly useful synthetic intermediates in the preparation of complex nitrogen-containing natural products and pharmaceutical targets, as exemplified by a practical asymmetric synthesis of the influenza drug (–)-oseltamivir (FIG. 1b) (Lavilla, R., *J. Chem. Soc. Perkin Trans.* 1 1141-1156 (2002); Wender, P. A. et al., *J. Am. Chem. Soc.* 102, 6157-6159 (1980); Mizoguchi, H. et al., *Nature Chem.* 6, 57-64 (2014); Duttwyler, S. et al., *Angew. Chem. Int. Ed.* 53, 3877-3880 (2014); and Satoh, N. et al., *Angew. Chem. Int. Ed.* 46, 5734-5736 (2007)). Because of their importance, many synthetic strategies have been developed for the preparation of 1,2-dihydropyridines, however, most employ stoichiometric activating reagents, are not highly selective, often require harsh reaction conditions, and suffer from competing over-reductions (Bull, J. A. et al., *Chem. Rev.* 112, 2642-2713 (2012)).

Only recently have catalysts based on magnesium or rhodium demonstrated activity for pyridine 1,2-hydroboration to afford the corresponding N-boryl-1,2-dihydropyridine derivatives (FIG. 1c) (Arrowsmith, M. et al., *Organometallics* 30, 5556-5559 (2011); Oshima, K. et al., *J. Am. Chem. Soc.* 134, 3699-3702 (2012); and Osakada, K. et al., *Angew. Chem. Int. Ed.* 50, 3845-3846 (2011)). Despite such progress, these approaches have significant limitations, including functional group compatibility, regioselectivity, and the high cost of rhodium (Hao, L. et al., *Angew. Chem. Int. Ed.* 37, 3126-3129 (1998); Gutsulyak, D. V. et al., *Angew. Chem. Int. Ed.* 50, 1384-1387 (2011); Lee, S.-H. et al., *Organometallics* 32, 4457-4464 (2013)). Therefore, selective catalytic 1,2-dearomatization of diverse azines using earth-abundant catalysts under mild reaction conditions and with broad functional group compatibility remains a challenge.

Unlike platinum group metals, lanthanide catalysts are attractive due to the earth-abundance of these sustainable metals (comparable to that of Ni, Co, Cu), low toxicity, low cost (La is >2000× cheaper than Rh in per-mole prices), relatively stable supply, scarcely explored heterocycle reactivity, and mild conditions employed in the present catalytic reactions (Weiss, C. J. et al., *Dalton Trans.* 39, 6576-6588 (2010)). The efficient organolanthanide-catalyzed anti-Markovnikov hydroboration (and hydrosilylation) of olefins has previously been reported (FIG. 1d) (Harrison, K. N. et al., *J. Am. Chem. Soc.* 114, 9220-9221 (1992); Hong, S. et al., *Acc. Chem. Res.* 37, 673-686 (2004); and Fu, P.-F. et al., *J. Am. Chem. Soc.* 117, 7157-7168 (1995)). Mechanistically, the reaction proceeds via addition of a labile $Cp*_2Ln-H$ bond across the C=C functionality, followed by rapid Ln-C . . . H—B σ-bond transposition. The challenge of hydroborating multiple carbon-heteroatom bonds should be addressed, specifically the notably unreactive C=N functionalities of azines (Obora, Y. et al., *J. Am. Chem. Soc.* 119, 3745-3755 (1997)).

To cure the deficiencies of the prior art, a general catalytic approach to the efficient, regioselective 1,2-dearomatization of diverse pyridines and other azines using pinacolborane (HBpin), along with a detailed kinetic and computational mechanistic analysis is provided herein. This reaction is catalyzed by 1% $[Cp*_2LaH]_2$ (1) under mild, atom-efficient reaction conditions (FIG. 1e) (Jeske, G. et al., *J. Am. Chem. Soc.* 107, 8091-8103 (1985)). Regarding lanthanide abundance, recent reports forecast near-term stabilization of both price and supply. Indeed, initiatives by many governments, WTO rulings against monopolistic practices and trade violations, as well as reopening of closed and the development of new mining facilities have triggered a rapid worldwide decline in lanthanide prices to the pre-2011-crisis levels, thus providing assurance of a continuous, sustainable future supply of low-cost lanthanide metals (Humphries, M., *Rare Earth Elements: The Global Supply Chain* (Congressional Research Service, 2013)).

SUMMARY OF THE INVENTION

In light of the foregoing, it is an object of the present invention to provide a method for the organolanthanide-catalyzed 1,2-dearomatization of an azine ring with main-group element hydrides, such as, for example, pinacolborane (HBpin), under anhydrous/anaerobic conditions. The method comprises treating the azine with one or more (or at least one) main-group element hydrides in the presence of a catalyst. The method displays good functional group compatibility and enables the regiospecific preparation of a wide range of, for example, 1,2-dihydropyridines. The dearomatized products are prominent motifs in many naturally occurring and pharmacologically active compounds and serve as useful intermediates in the synthesis of valuable nitrogen-containing molecules. Particularly noteworthy is the ability of the present catalytic system to address shortcomings of the prior art, i.e. the existing azine ring dearomatization methods, especially the reliance on precious transition metal catalysts.

It is also an object of the present invention to provide compounds prepared by a method for the organolanthanide-catalyzed 1,2-hydroboration of an azine ring with a main-group element hydride such as, for example, HBpin under anhydrous/anaerobic conditions comprising treating the azine with the main-group element hydride in the presence of a catalyst to afford the compound.

Other objectives, features, benefits and advantages of the present invention will be apparent from this summary and its descriptions of certain embodiments of compounds and methods, and will be readily apparent to those skilled in the art having knowledge of the synthetic techniques described therewith. Such objectives, features, benefits and advantages will be apparent from the above as taken into conjunction with the accompanying examples, data, figures and all reasonable inferences to be drawn therefrom.

HBpin in $C_6D_{12}$, wherein Product=1-(4,4,5,5-tetramethyl-1,3,2-dioxaborolan-2-yl)-1,2-dihydropyridine (3a) and *=unidentified impurity.

Figure 27:
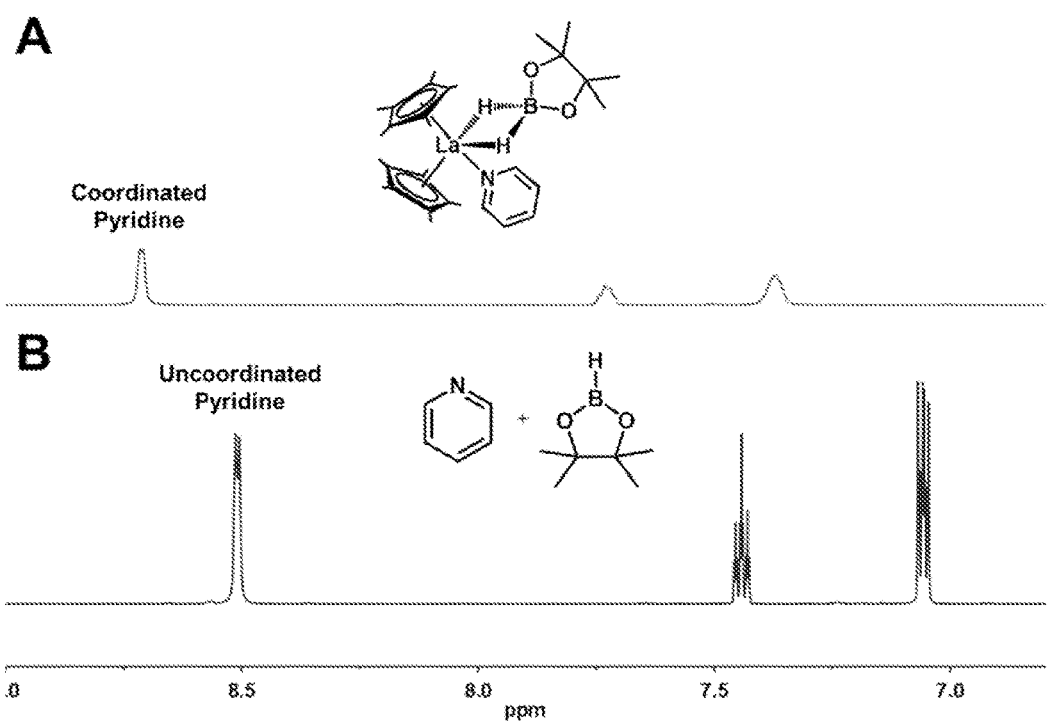

FIG. 27 is an expansion (δ 9.00–6.80 ppm) of $^1H$ NMR stack spectra plot of a) pyridine, and b) $[Cp*_2LaH]_2$+pyridine+HBpin in $C_6D_{12}$.

Figure 28:
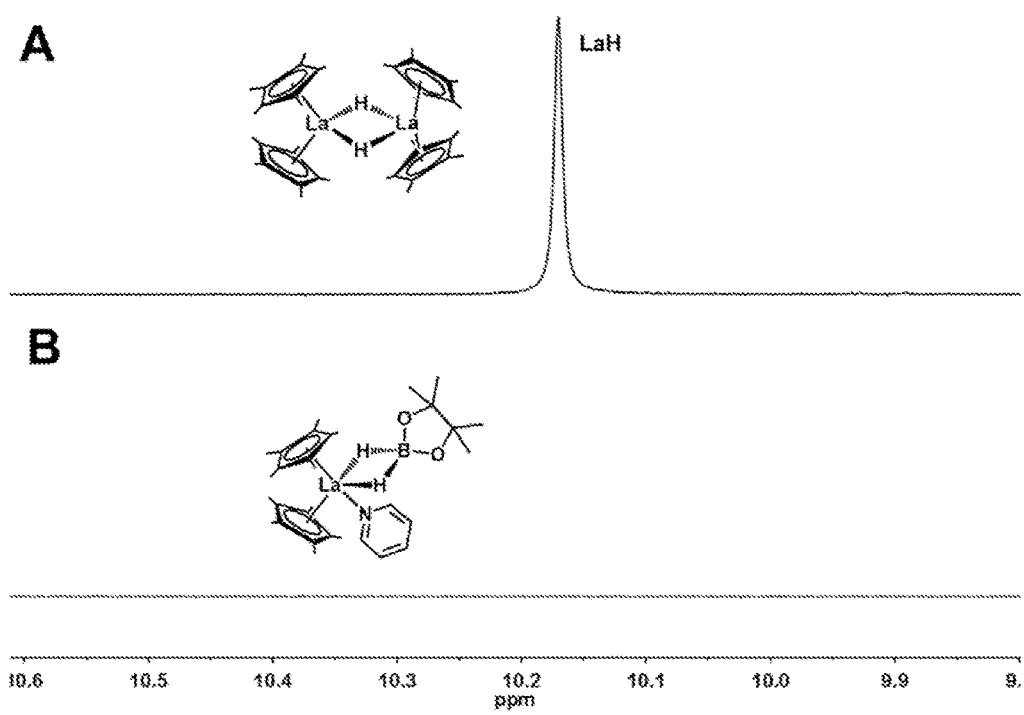

FIG. 28 is an expansion (δ 10.60-9.80 ppm) of $^1H$ NMR stack spectra plot of a) $[Cp*_2LaH]_2$ and b) $[Cp*_2LaH]_2$+pyridine+HBpin in $C_6D_{12}$.

Figure 29:
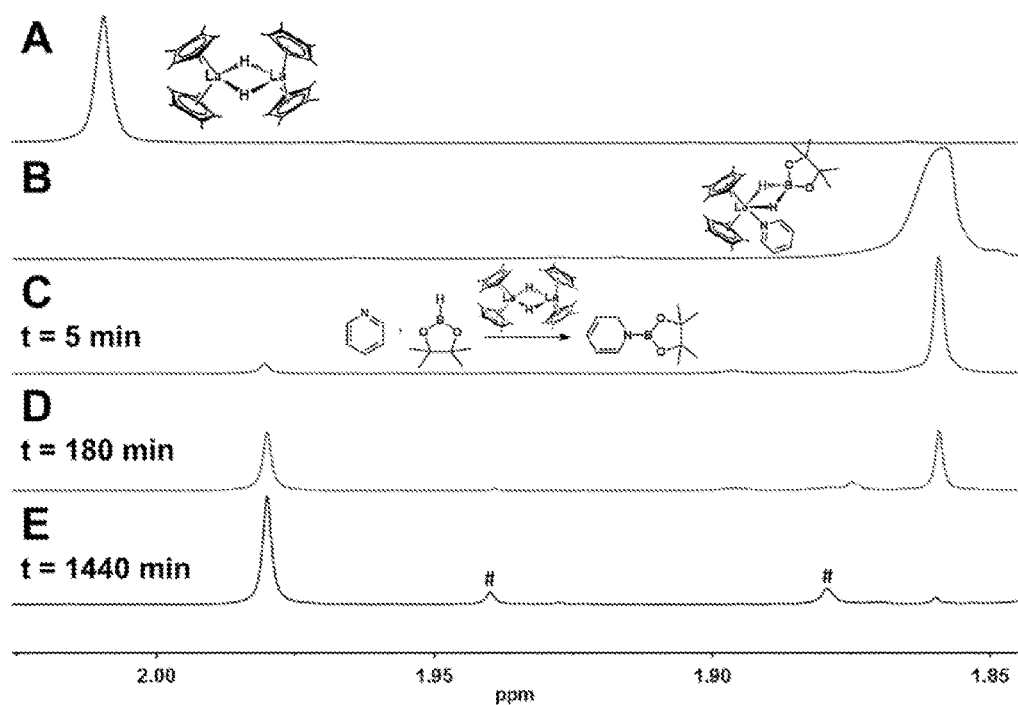

FIG. 29 is an expansion (δ 2.05-1.83 ppm) of $^1H$ NMR stack spectra plot of a) $[Cp*_2LaH]_2$; b) stoichiometric reaction between $[Cp*_2LaH]_2$, pyridine, and HBpin; c) catalytic reaction between pyridine and HBpin in the presence of 1 mol % $[Cp*_2LaH]_2$ after 5 minutes; d) after 180 minutes; and e) after 1440 min in $C_6D_{12}$, wherein #=unidentified byproducts.

Figure 30:
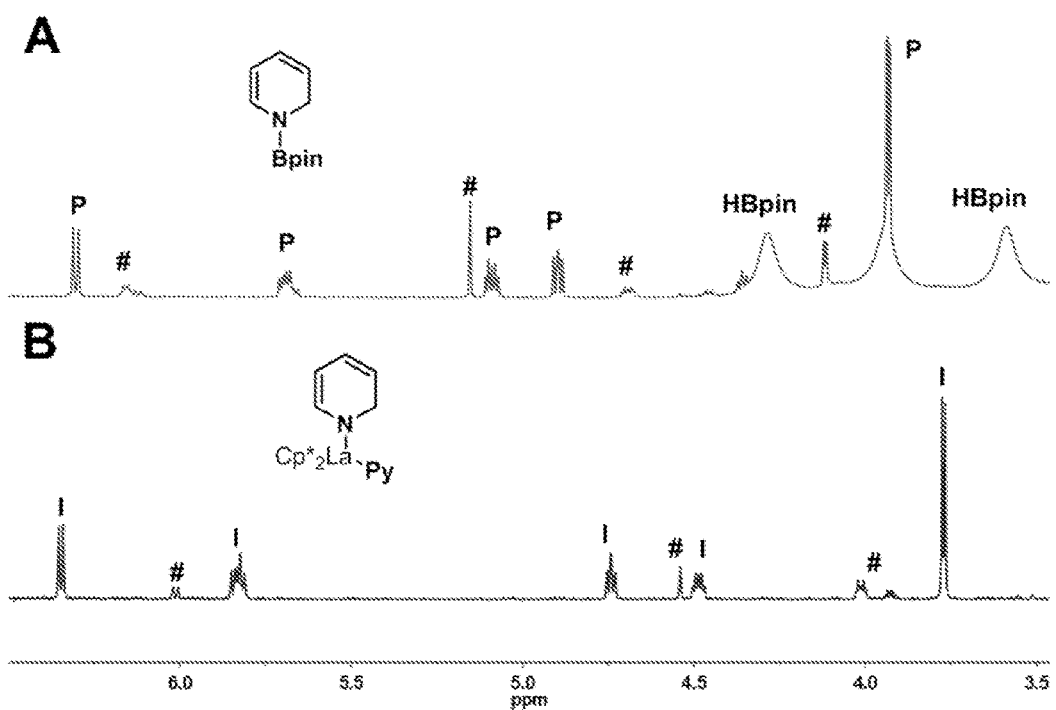

FIG. 30 is an expansion (δ 6.50-3.45 ppm) of $^1H$ NMR stack spectra plot of catalytic reaction of a) $[Cp*_2LaH]_2$+Pyridine and b) $(Cp*_2LaH]_2$+Pyridine) +HBpin after 5 minutes in $C_6D_{12}$, wherein P=1-(4,4,5,5-tetramethyl-1,3,2-dioxaborolan-2-yl)-1,2-dihydropyridine (3a), I=1,2-organolanthanum-dihydropyridine complex, and #=unidentified byproducts.

Figure 31:
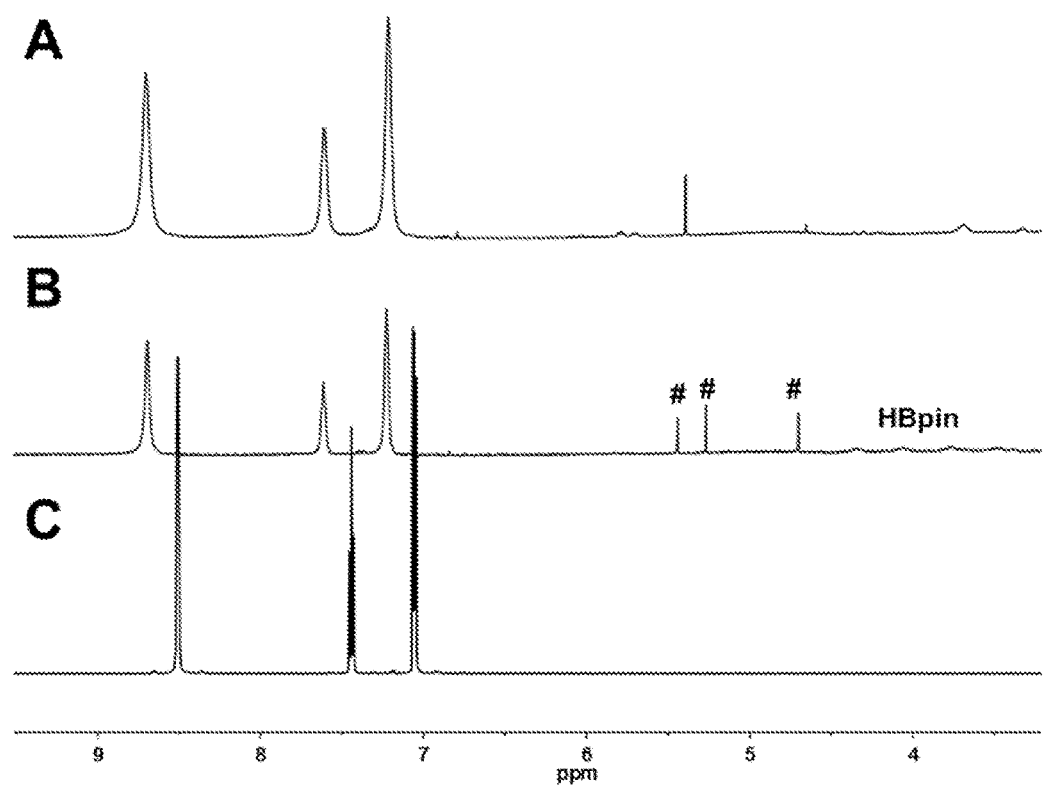

FIG. 31 is an expansion (δ 9.50-3.25 ppm) of $^1H$ NMR stack spectra plot of stoichiometric reaction of a) $[Cp*_2LaH]_2$+pyridine; b) $([Cp*_2LaH]_2$+pyridine)+HBpin; and c) pyridine in $C_6D_{12}$, wherein #=unidentified byproduct.

Figure 32:
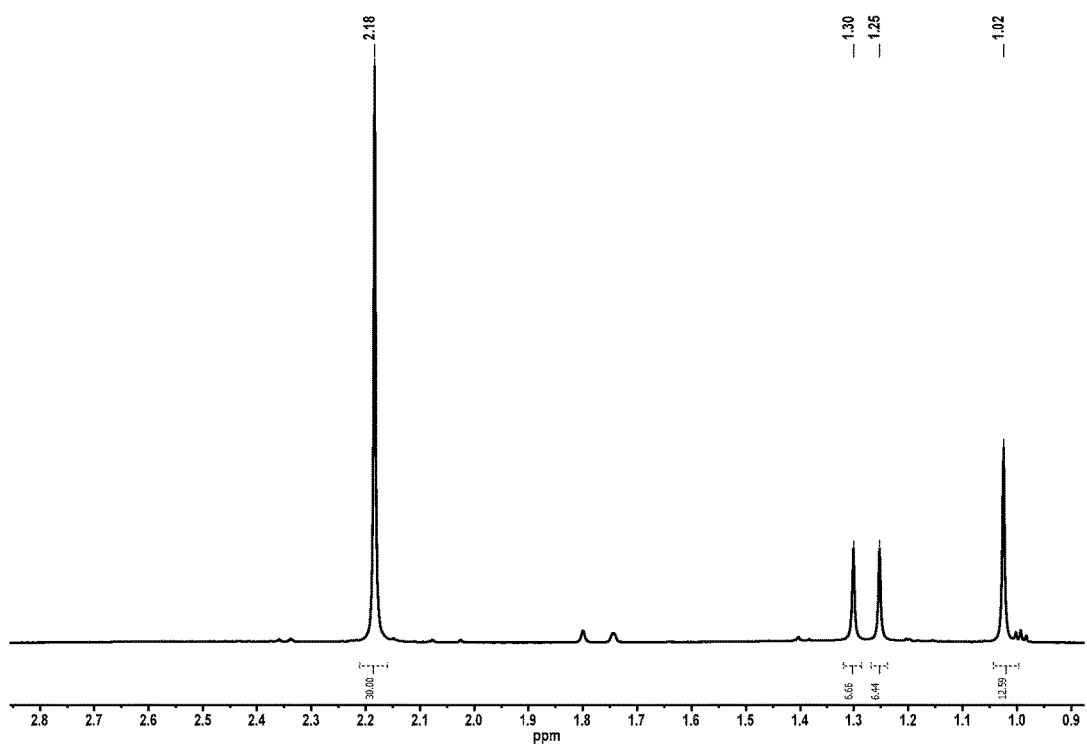

FIG. 32 is a $^1H$ NMR spectrum of 4 in $C_6D_6$.

Figure 33:
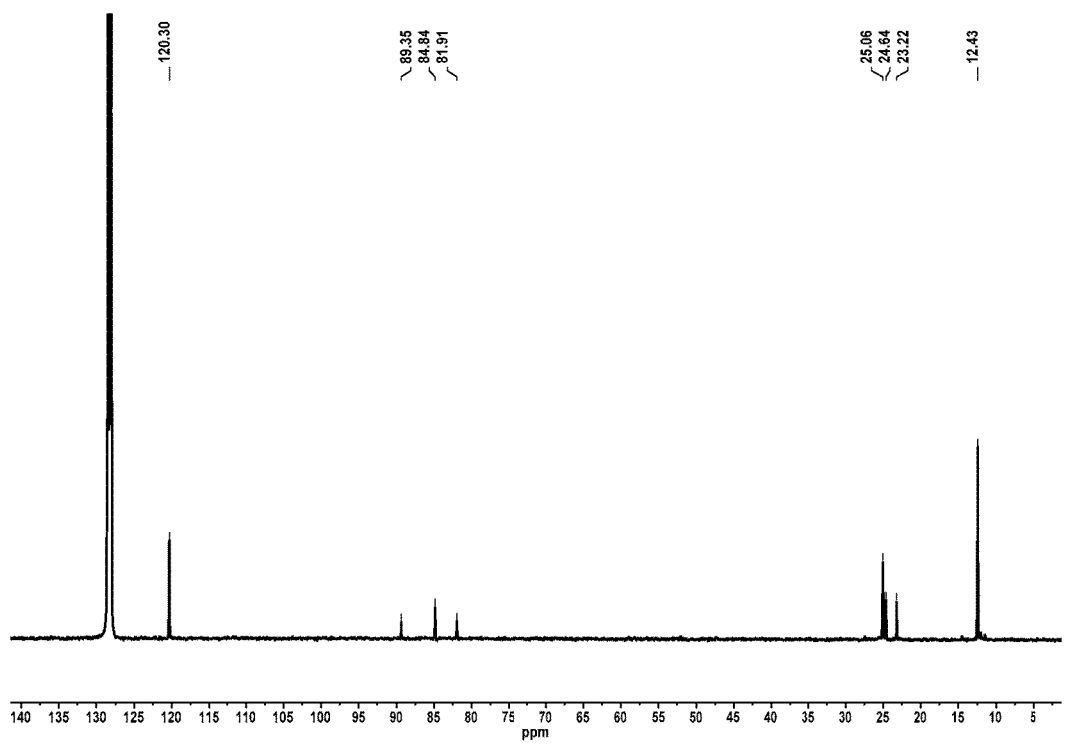

FIG. 33 is a $^{13}C$ NMR spectrum of 4 in $C_6D_6$.

Figure 34:
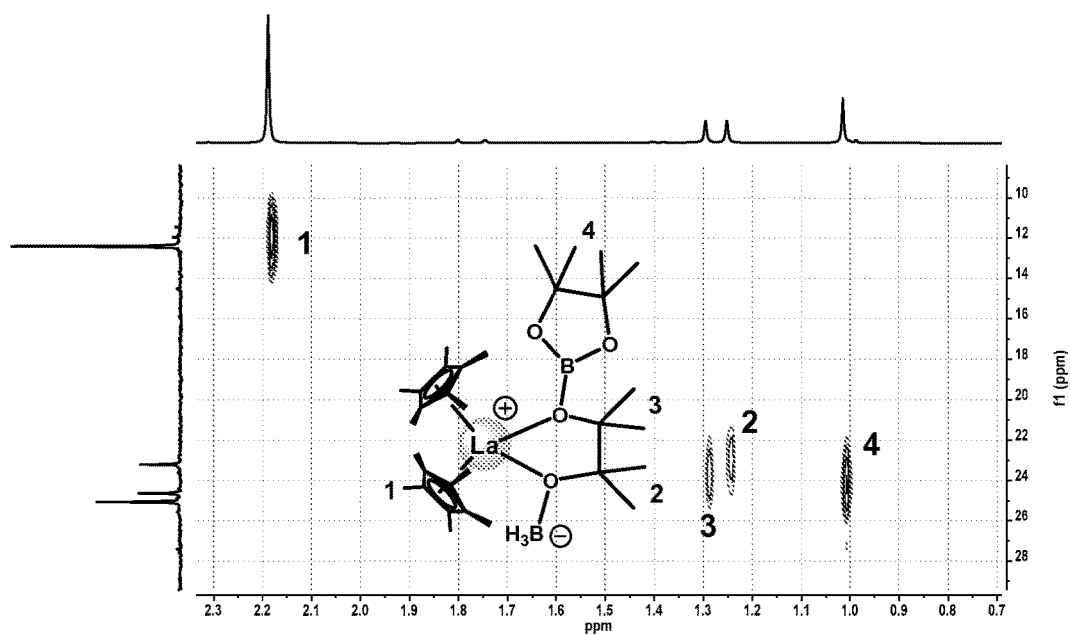

FIG. 34 is a $^1H$-$^{13}C$ HSQC NMR spectrum of 4 in $C_6D_6$.

Figure 35:
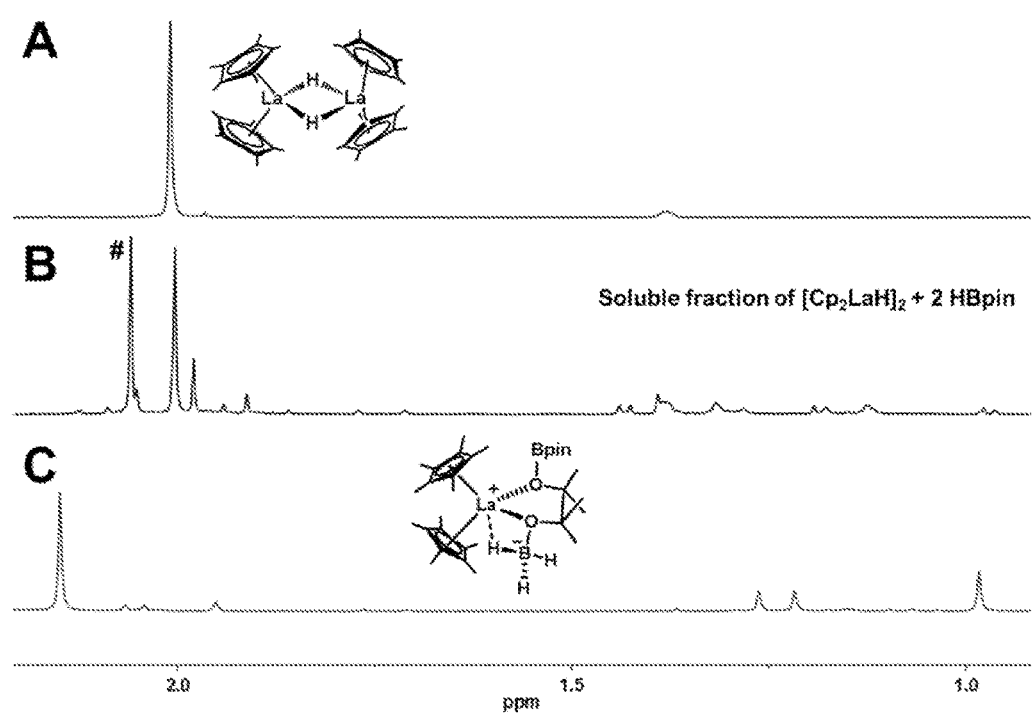

FIG. 35 is an expansion (2.20–0.90 ppm) of $^1H$ NMR stack spectra plot of a) $[Cp*_2LaH]_2$; b) soluble fraction of $[Cp*_2LaH]_2$+2HBpin; and c) insoluble fraction of $[Cp*_2LaH]_2$+2HBpin in $C_6D_{12}$, wherein #=unknown compound.

Figure 36:
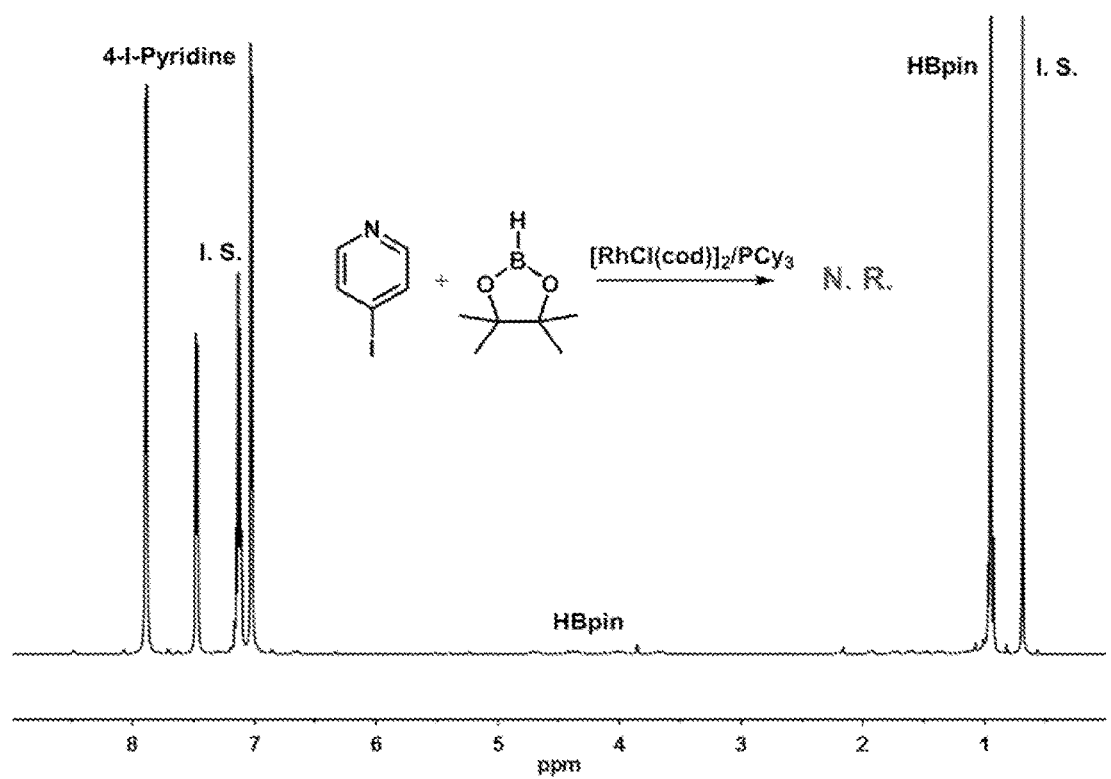

FIG. 36 is a $^1H$ NMR spectrum of the attempted reaction between 4-I-pyridine and HBpin using $[RhCl(cod)]_2/PCy_3$ catalytic system in $C_6D_6$ after 24 hours at 50° C.

Figure 37:
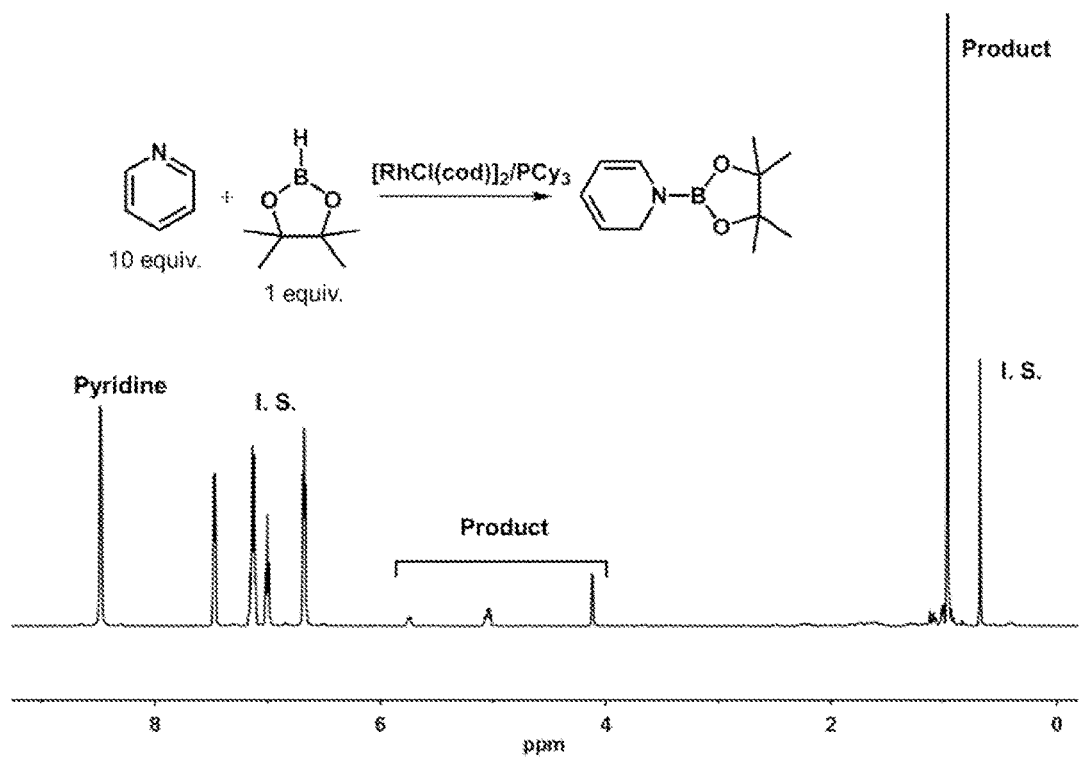

FIG. 37 is a $^1H$ NMR spectrum of reaction between 10 equivalents of pyridine and 1 equivalent of HBpin using $[RhCl(cod)]_2/PCy_3$ catalytic system in $C_6D_6$ after 16 hours at 50° C.

Figure 38:
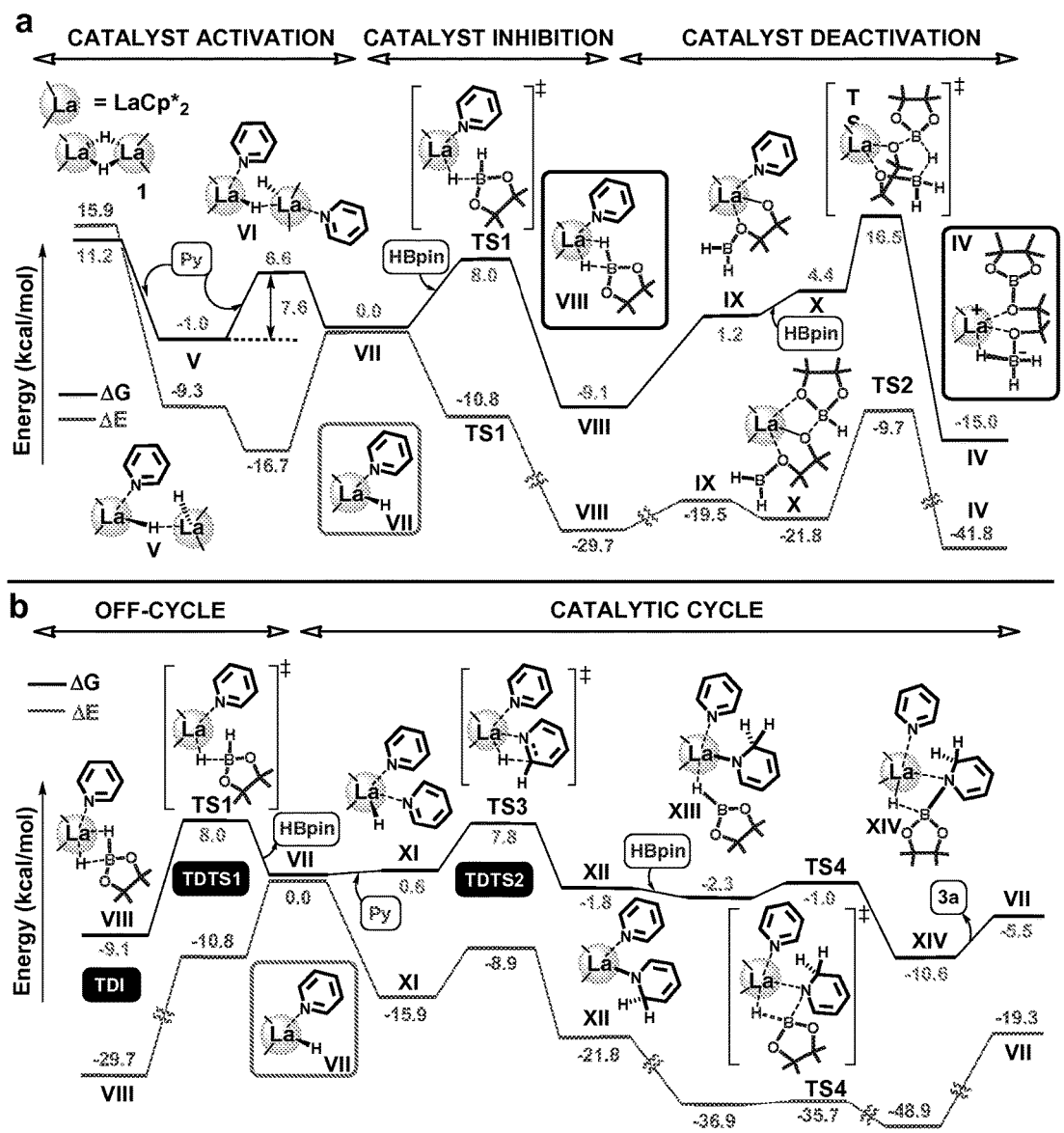

FIG. 38 is a) an energetic profile for transformations of the precatalyst 1 in the presence of pyridine and HBpin reactants: active catalyst generation, inhibition, and deactivation; b) an energetic profile of the catalytic cycle for the La-catalyzed pyridine dearomatization along with the off-cycle active catalyst inhibition process.

Figure 39O:
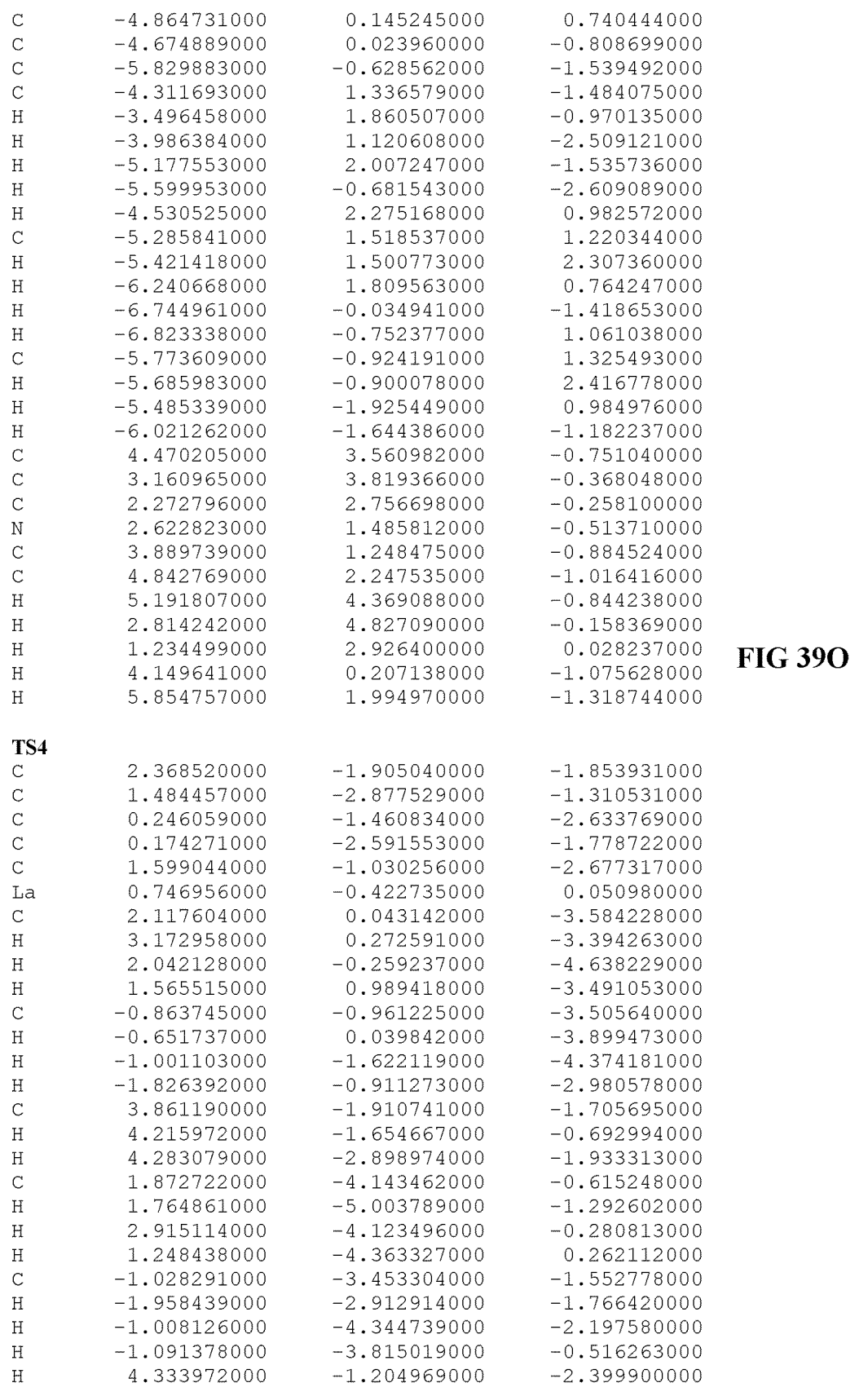

FIGS. 39A-U provides Cartesian Coordinates for all computed structures.

DETAILED DESCRIPTION OF CERTAIN EMBODIMENTS

The invention relates to a method for the organolanthanide-catalyzed 1,2-hydroboration of an azine ring with a main-group element hydride. In an embodiment, the main-group element hydride is pinacolborane (HBpin), the method comprising treating the azine with HBpin in the presence of an organolanthanide catalyst to afford a 1,2-dihydropyridines.

It is appreciated that main-group element hydrides other than or in combination with HBpin can be employed with the methods disclosed herein. By "main-group element hydride" is meant a compound of the formula $H-ER_n$, wherein H is hydrogen; E is a main-group element from Groups 1-2 and 13-18 (other than hydrogen), R is linear or together with E is cyclic, and consists of one or more groups selected from a group consisting of H, O, NH (or N substituted with a group other than H), C substituted with two or three H or at each instance independently with another group, wherein n=1-4, and wherein the one or more independent groups depends on the value of n and/or whether R is linear or cyclic. Preferred main-group elements are selected from a group consisting of B, Si, Sn and Ge. As discussed above, the main-group element hydride is preferably pinacolborane. By "pinacolborane" or "(HBpin)" is meant 4,4,5,5-tetramethyl-1,3,2-dioxaborolane. The formula of HBpin is depicted below.

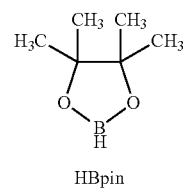

HBpin

The organolanthanide catalyst has a formula of $(L)_xLn-H$, wherein L is an ancillary ligand, such as, for example, Cp, Cp*, CGC, Cp", and the like; Ln is a lanthanide element, and preferably selected from a group consisting of Sc, Y, La, Sm, Nd, Yb and Lu; X is an integer, and preferably 1 or 2; and H is hydrogen.

The following abbreviations/structures can be used interchangeably herein:

CGC-$Me_2SiCp"NCMe_3$.
Me-Methyl.
Cp"-

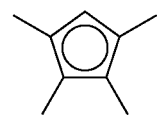

($C_5Me_4$).
Cp*-

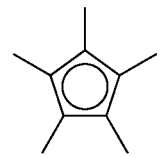

($C_5Me_5$).

By "azine ring" as provided herein is meant a cyclic organic compound having a ring including one or more nitrogen atoms. Preferably, the cyclic organic compound is six-membered or and contains one or more nitrogen atoms in the ring, such as, for example, pyridine; or the cyclic organic compound is a fused six-membered ring system of two or more rings and contains one or more nitrogen atoms in the ring, such as, for example, quinoline. The azine ring can be unsubstituted or substituted with one or more substituents.

In an embodiment, optimization of reaction parameters, including catalyst concentration, substrate ratio, and reaction temperature, reveal that clean 1,2-regiospecific pyridine hydroboration as well as overall optimal catalytic performance [turnover frequency (TOF), turnover number (TON), and conversion] is achieved, preferably with equimolar quantities of HBpin and pyridine and less than equimolar quantities of catalyst, for example, 1% catalyst 1 at 35° C. in cyclohexane (Table 1, entry 3). Similar reaction efficiency is achieved when the solvent comprises (or consists essentially of) benzene (entry 4). It is noted that excess pyridine is unnecessary to reach high conversions, and no regioisomeric N-boryl-1,4-dihydropyridine is detected during the reaction course, even at 100° C. for 48 hours (Arrowsmith, M. et al., *Organometallics* 30, 5556-5559 (2011); Oshima, K. et al., *J. Am. Chem. Soc.* 134, 3699-3702 (2012); and Gountchev, T. I. et al., *Organometallics* 18, 2896-2905 (1999), all of which are incorporated herein by reference).

TABLE 1

La-catalyzed 1,2-hydroboration of pyridine with pinacolborane (HBpin).[a]

| Entry | Temperature (° C.) | Yield (%)[b] | Time (h) | TOF (h$^{-1}$)[c] |
|---|---|---|---|---|
| 1[d] | 25 | 0 | 48 | — |
| 2 | 25 | 90 | 70 | 6.6 ± 0.1 |
| 3 | 35 | 87 | 11 | 17.0 ± 0.6 |
| 4[e] | 35 | 77 | 7.5 | 16.5 ± 1.6 |
| 5 | 45 | 72 | 5 | 46.9 ± 1.2 |
| 6 | 55 | 68 | 2.5 | 99.4 ± 2.5 |

[a]Reaction conditions: pyridine (0.25 mmol), HBpin (0.25 mmol), [Cp*$_2$LaH]$_2$ (2.5 × 10$^{-3}$ mmol), Ph$_3$SiMe (5.43 × 10$^{-2}$ mmol) in 1.25 mL of C$_6$D$_{12}$. Each entry performed in triplicate.
[b]By $^1$H NMR analysis with Ph$_3$SiMe as internal standard.
[c]Turnover frequency, TOF = [product] [catalyst]$^{-1}$ h$^{-1}$
[d]No La catalyst.
[e]C$_6$D$_6$ as the solvent.

The hydroboration scope is explored with a series of substituted pyridines and related six-membered heterocycles using equimolar HBpin and 1% catalyst 1 at 35° C. (Table 2). It is found that a wide range of azines possessing both strongly electron-donating and -withdrawing groups undergo a highly efficient 1,2-regiospecific hydroboration to afford the corresponding dearomatized products in moderate-to-excellent yields and with moderate-to-high turnover frequencies (TOFs). Both electronic and steric factors are found to exercise significant influence on the hydroboration rates. That steric encumbrance plays a significant role is evidenced by the lack of 1,2-hydroboration activity for 2-substituted pyridines (vide infra) and is consistent with trends for other organolanthanide/actinide- and group-4-catalyzed hydroelementation processes (Reznichenko, A. L. et al., *Top. Organomet. Chem.* 43, 51-114 (2013), incorporated herein by reference).

A variety of functional groups such as CF$_3$, OMe, (2S)-1-methyl-2-pyrrolidinyl (nicotine), 1-piperidinyl, phenyl, vinyl, SnMe$_3$, and Bpin groups, as well as halogens (F, Cl, Br, and I) are all compatible with this organolanthanide-catalyzed process (Table 2), thus offering the possibility of further selective functionalization of the dearomatized products. Halogenated dihydropyridines, especially iodo- and bromo-substituted molecules, are challenging syntheses using the existing precious metal-catalyzed methodologies due to competing C-halogen bond oxidative addition to Rh(I) (see Oshima et al.). Furthermore, the reported Mg(II)-catalyzed dearomatization is incompatible with coordinating substituents (e.g., Me$_2$N, OMe) (see Arrowsmith et al.). In contrast, these functionalities are completely tolerated under the present catalytic conditions. The hydroboration of 4-substituted pyridines proceeds smoothly to furnish the corresponding dearomatized products in high yields. Reactions with pyridines having electron-withdrawing groups at C4 position exhibit increased initial rates (CF$_3$>I>H) and require shorter reaction times to reach completion (<1 h), whereas the presence of electron-donating groups leads to falling TOFs in the order: Ph>OMe>Me>NR$_2$ (Table 2). In addition, catalytic hydroboration of various meta-functionalized pyridines affords N-boryl-3-substituted-1,2-dihydropyridines with good-to-excellent regioselectivities, with the H atom delivered preferentially to the more hindered C2 position. Also, hydroboration of benzofused azines, including quinoline and isoquinoline, proceeds rapidly (<1 h) to afford the corresponding 1,2-dearomatized derivatives in good yields. Finally, the reaction of pyrazine with 1.0 equivalent of HBpin results in selective formation of a N,N'-diboryl-1,2,3,4-tetrahydropyrazine along with 0.5 equivalent of unreacted pyrazine, with no mono-hydroboration product observed. When two equivalents of HBpin are used, the reaction proceeds at the same initial rate (TOF) to produce the doubly hydroborated product in 92% yield (Oshima, K. et al. II, *Chem. Commun.* 48, 8571-8573 (2012), incorporated herein by reference). Furthermore, the La-catalyzed dearomatization is successfully scaled up without significant loss in efficiency as indicated in entry 3 of Table 2 (compound 3c), wherein the 1,2-dearomatized product is isolated by simple filtration in 87% yield.

TABLE 2

Substrate scope for the La-catalyzed 1,2-hydroboration of the indicated azines.[a]

21 examples
no excess reagents
low catalyst loadings; abundant metal
regiospecific 1,2-addition
good functional group tolerance 3b 251.5 ± 1.7
[96%; 0.4 h]

TABLE 2-continued

Substrate scope for the La-catalyzed 1,2-hydroboration of the indicated azines.[a]

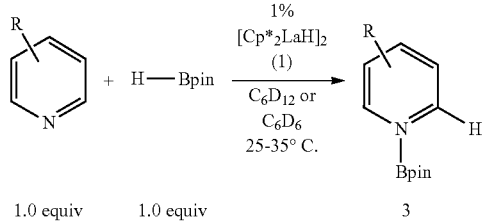

21 examples
no excess reagents
low catalyst loadings; abundant metal
regiospecific 1,2-addition
good functional group tolerance

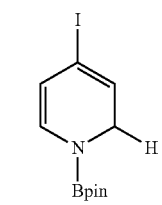 3c 180.1 ± 2.1
[95%; 0.7 h]
2.5 mmol
87%; 0.72 g

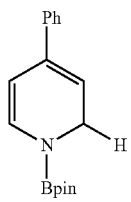 3d 28.8 ± 0.4
[99%; 3.0 h]

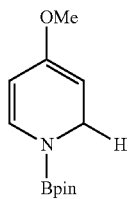 3e 25.2 ± 2.2
[97%; 7.5 h]

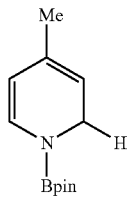 3f 16.8 ± 2.1
[96%; 4.0 h]

TABLE 2-continued

Substrate scope for the La-catalyzed 1,2-hydroboration of the indicated azines.[a]

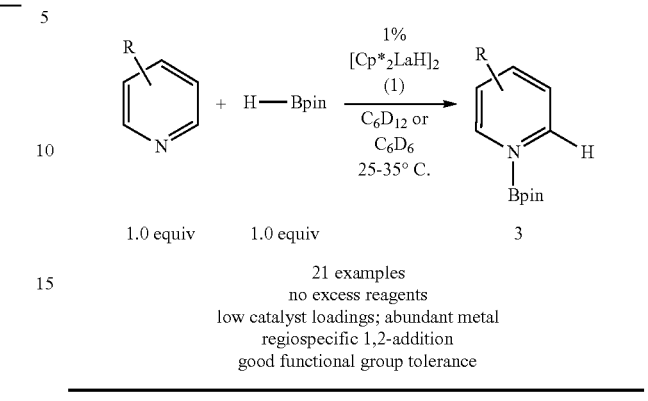

21 examples
no excess reagents
low catalyst loadings; abundant metal
regiospecific 1,2-addition
good functional group tolerance

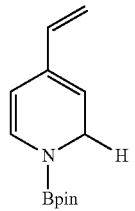 3g 70.5 ± 7.3
[55%; 2.0 h][b]

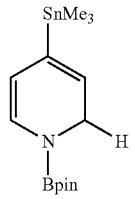 3h 59.9 ± 0.3
[97%; 2.0 h][c]

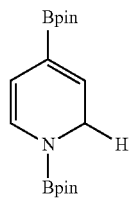 3i 12.0 ± 0.4
[67%; 18.5 h][c]

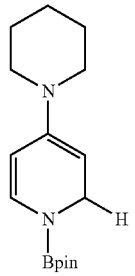 3j 14.2 ± 0.7
[66%; 20.0 h]

TABLE 2-continued

Substrate scope for the La-catalyzed 1,2-hydroboration of the indicated azines.[a]

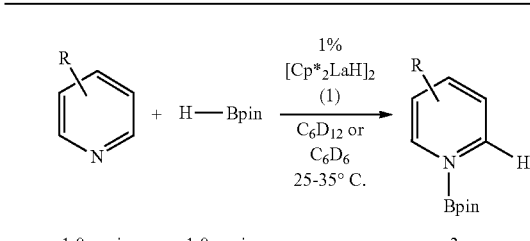

1.0 equiv   1.0 equiv                3

21 examples
no excess reagents
low catalyst loadings; abundant metal
regiospecific 1,2-addition
good functional group tolerance

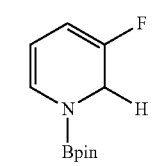

51.7 ± 0.6
[51%; 6.0 h]
{95:5}

3k

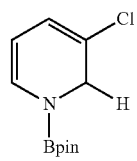

135.6 ± 0.1
[99%; 0.8 h]
{83:17}

3l

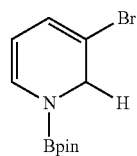

106.6 ± 3.4
[96%; 0.5 h]
{82:18}

3m

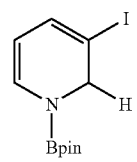

252.6 ± 11.9
[86%; 0.5 h]
{79:21}

3n

TABLE 2-continued

Substrate scope for the La-catalyzed 1,2-hydroboration of the indicated azines.[a]

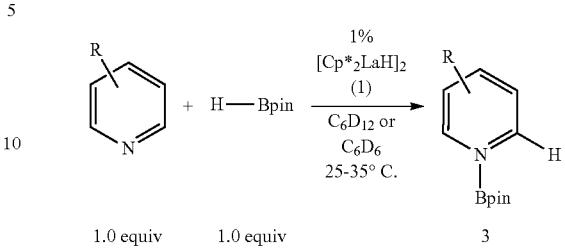

1.0 equiv   1.0 equiv                3

21 examples
no excess reagents
low catalyst loadings; abundant metal
regiospecific 1,2-addition
good functional group tolerance

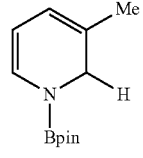

75.6 ± 3.0
[80%; 1.0 h]
{96:4}

3o

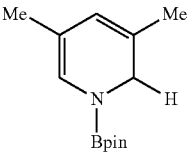

40.7 ± 5.0
[97%; 3.3 h]

3p

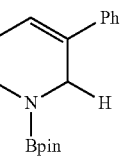

201.6 ± 5.2
[97%; 0.4 h]
{90:10}

3q

24.2 ± 2.5
[80%; 21.0 h]
{100:0}

3r

TABLE 2-continued

Substrate scope for the La-catalyzed 1,2-hydroboration of the indicated azines.[a]

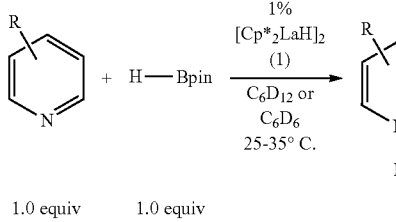

1.0 equiv    1.0 equiv    3

21 examples
no excess reagents
low catalyst loadings; abundant metal
regiospecific 1,2-addition
good functional group tolerance

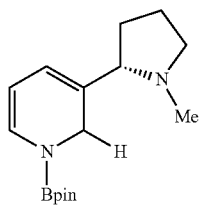

91.1 ± 6.4
[98%; 1.0 h]
{93:7}

3s

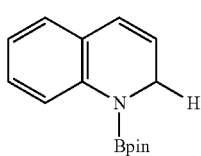

166.1 ± 0.8
[65%; 0.4 h]

3t

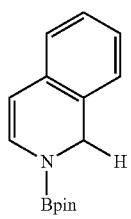

447 ± 20
[84%; 0.2 h][d]

3u

TABLE 2-continued

Substrate scope for the La-catalyzed 1,2-hydroboration of the indicated azines.[a]

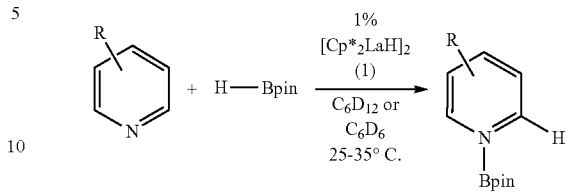

1.0 equiv    1.0 equiv    3

21 examples
no excess reagents
low catalyst loadings; abundant metal
regiospecific 1,2-addition
good functional group tolerance

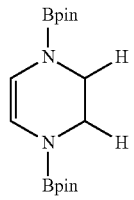

82.6 ± 4.2
[92%; 15.0 h][e]

3v

[a]Reaction conditions: azine (0.25 mmol), HBpin (0.25 mmol), [Cp*$_2$LaH]$_2$ (1 mol %, 2.5 × 10$^{-3}$ mmol), Ph$_3$SiMe (Inter. Std.; 5.43 × 10$^{-2}$ mmol) in 1.25 mL of C$_6$D$_{12}$ at 35° C. Each entry performed in triplicate. Turnover frequencies (TOF (h$^{-1}$) = [product] [catalyst]$^{-1}$ h$^{-1}$) by $^1$H NMR analysis with Ph$_3$SiMe internal standard. Quantities in brackets are NMR yields and corresponding reaction times. Isomer ratios in brackets refer to ratios of regioisomeric 3- and 5-substituted-1,2-dihydropyridines.
[b]Reaction monitored by 1H NMR and halted immediately after all HBpin consumed to minimize 3 g polymerization.
[c]Performed in C$_6$D$_6$.
[d]Performed at 25° C.
[e]With 2.0 equiv. HBpin (0.5 mmol).

Figure 1:
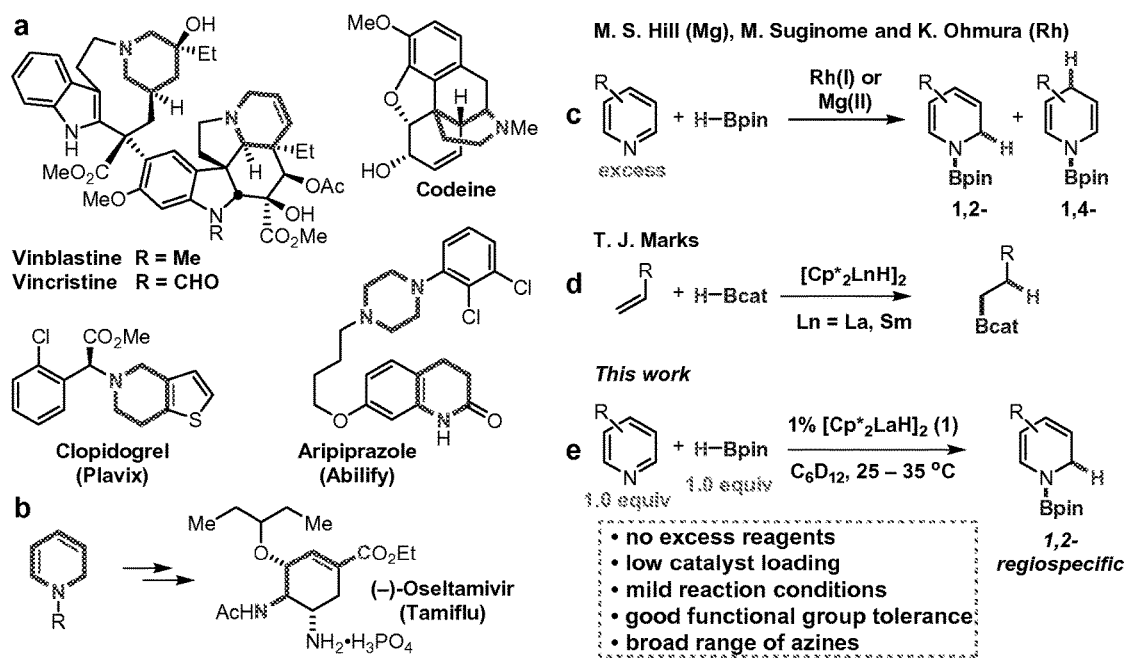
FIG. 1 depicts the importance of saturated six-membered nitrogenous heterocycles and recent progress toward their synthesis; in particular a) selected examples of natural products and drugs containing dearomatized pyridines and azines; b) synthetic utility of 1,2-dihydropyridines; c) recent advances in metal-catalyzed dearomatization of pyridines with pinacolborane; d) example of organolanthanide-catalyzed alkene hydroboration; and e) scheme of the organolanthanide-catalyzed azine 1,2-dearomatization of the present invention.
Figure 2:
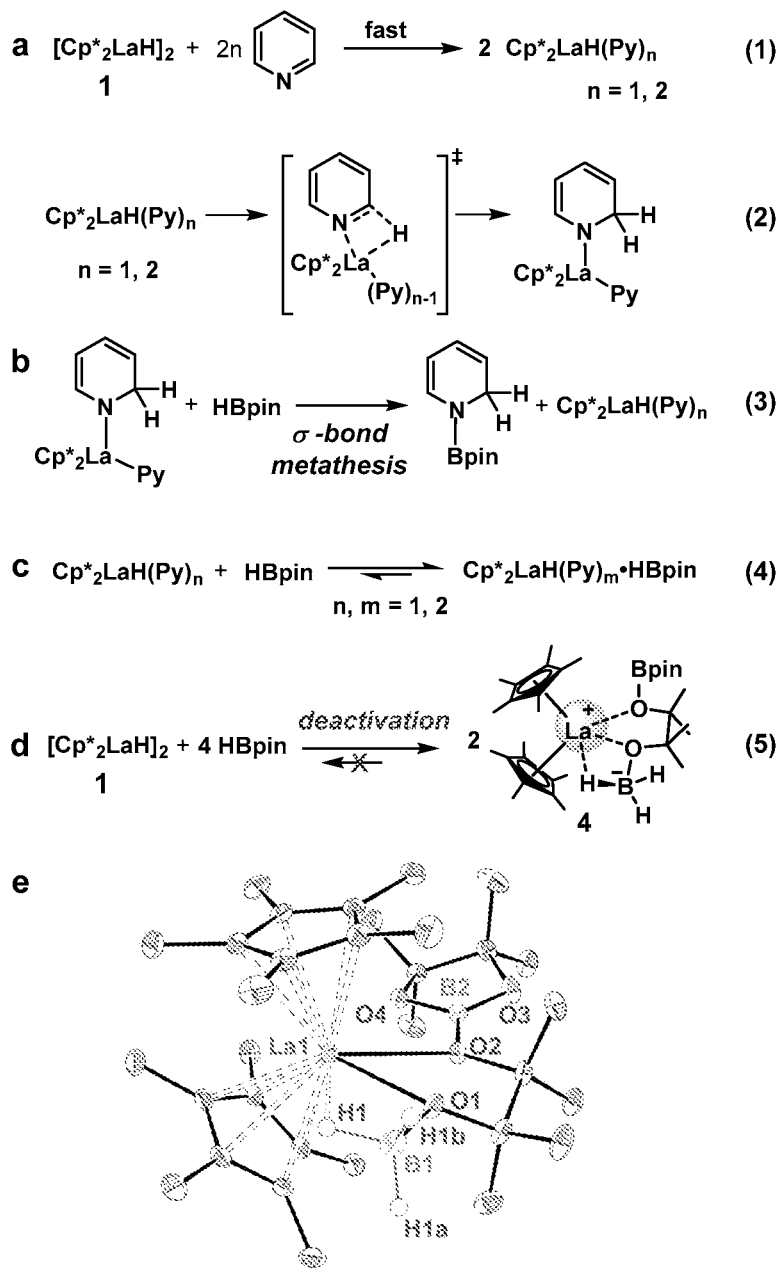
FIG. 2 is a plausible elementary reaction sequence for catalytic pyridine dearomatization; in particular a) bridge-cleaving reaction of 1 with pyridine to yield hydrido pyridine complexes which subsequently undergo intramolecular C=N insertion (equations 1 and 2); b) La—N/H—B σ-bond metathesis to release the dearomatized product and regenerate the hydrido pyridine complex; c) possible competitive inhibition by HBpin; d) reaction of 1 and HBpin to yield zwitterionic deactivation product 4; and e) ORTEP plot of the molecular structure of zwitterion 4.

A qualitative discussion of the experimental observables and the constraints placed on the various mechanistic scenarios is also provided herein, as well as a quantitative DFT (Discrete Fourier Transform)/Energetic Span analysis. In agreement with related literature (Ringelberg, S. N., *Bond activation and catalysis with organolanthanides*. Ch. 5 (Dissertation, University Library Groningen, Groningen, 2001, incorporated herein by reference), treating a pale yellow solution of 1 with excess pyridine under catalytically relevant conditions effects a rapid color change to orange and affords a Cp*$_2$La(NC$_5$H$_6$)(Py) complex in which one pyridine is dearomatized via La—H 1,2-addition across the pyridine C=N unit as identified by in situ $^1$H NMR spectroscopy (FIG. 2a, S21-32; eqs. 1 and 2) (in FIG. 2, thermal ellipsoids are drawn at the 50% probability level, and H atoms are omitted for clarity, except for the BH$_3$ group). Subsequent addition of 1.0 equivalent HBpin yields the dearomatized B—N product (equation 3). Mechanistically, these observations suggest rapid, stepwise cleavage of the dimeric La—H precatalyst 1 under catalytic reaction conditions to generate mono- and bis-pyridine adducts which then undergo intramolecular C=N insertion to create the bound, dearomatized ligand. Subsequent La—N/H—B σ-bond metathesis, driven by strong B—N bond formation (see computational study below) then affords the desired product and regenerates the active catalyst (equation 3). The stoichiometric addition of HBpin to 1 results in rapid formation in near-quantitative yields of the unusual and catalytically inert, colorless zwitterionic product 4, which is characterized by standard analytical techniques and x-ray diffraction (FIG. 2e, eq. 5). This reactivity mode of dialkoxyboranes with organo-f-element complexes has not been documented previously (Männig, D. et al., *J. Organomet. Chem.* 275, 169-171 (1984), incorporated herein by reference).

Detailed $^1$H NMR spectroscopic kinetic studies at 35° C. indicate that the rate law is first-order in La concentration, first-order in pyridine concentration below ~0.2 M, approaching zero-order at higher pyridine concentrations, and approximately inverse first-order in HBpin (equation 6). These results suggest that "resting state" of $$\frac{d[P]}{dt} = k_{obs} \frac{[La]^1 [\text{pyridine}]^x}{[HBpin]^1}; \text{ where } x = 0 - 1 \quad (6)$$

the catalyst may be a mononuclear Cp*$_2$LaH(py)$_n$-related species, with turnover-limiting intramolecular C=N insertion, implied by zero-order pyridine kinetics at high [pyridine] (Harrison, K. N. et al., *J. Am. Chem. Soc.* 114, 9220-9221 (1992); Fu, P.-F. et al., *J. Am. Chem. Soc.* 117, 7157-7168 (1995); and Obora, Y. et al., *J. Am. Chem. Soc.* 119, 3745-3755 (1997), all incorporated herein by reference). The inverse order in [HBpin] implies kinetic inhibition competing with the turnover-limiting step (e.g., equation 4), while the irreversible formation of complex 4 represents a deactivation pathway (equation 5) (Sevov, C. S. et al., *J. Am. Chem. Soc.* 134, 11960-11963 (2012) and Muhoro, C. N. et al., *J. Am. Chem. Soc.* 121, 5033-5046 (1999), both incorporated herein by reference). In addition, the $^1$H NMR spectroscopy provides no evidence for pyridine-HBpin reactivity/complexation. Kinetic measurements as a function of temperature (Table 1, entries 2-6) and standard Eyring and Arrhenius kinetic analyses provide the activation parameters, $\Delta H^{\neq}$=15.7(0.5) kcal/mol, $\Delta S^{\neq}$=-27.2 (0.3) cal/mol, and $E_a$=16.3(0.4) kcal/mol, suggesting an organized transition state (large negative $\Delta S^{\neq}$) characteristic of many d$^0$,f$^n$-centered hydroelementations (Hong, S. et al., Acc. Chem. Res. 37, 673-686 (2004) and Amin, S. B. et al., *Angew. Chem. Int. Ed.* 47, 2006-2025 (2008), both incorporated herein by reference).

Evaluation of several theoretical approaches identified the M06 DFT functional at 6-31G** level of theory as the best-performing DFT method for the present study. To validate the DFT-predicted mechanisms and guide computational efforts, the Energetic Span model recently developed by Kozuch, Shaik, and Martin is employed (with the aid of AUTOF program) (Kozuch, S., *WIREs Comput. Mol. Sci.* 2, 795-815 (2012) and Kozuch, S. et al., Acc. Chem. Res. 44, 101-110 (2011), both incorporated herein by reference). Here the experimental rate constant expressed as turnover frequency (TOF) is related to the calculated energy profile by the equations 7 and 8, where $\delta E$ is the energetic span $$TOF = \frac{k_B T}{h} e^{-\delta E/RT} \Pi \frac{[\text{Reactants}]}{[\text{Products}]} \bigg|_{\text{from TDI to TDTS}} \quad (7)$$

$$\delta E = \begin{cases} G_{TDTS} - G_{TDI} & \text{if } TDTS \text{ appears after } TDI \ (a) \\ G_{TDTS} - G_{TDI} + \Delta G_r & \text{if } TDTS \text{ appears before } TDI \ (b) \end{cases} \quad (8)$$

representing the Gibbs free energy difference between the TOF-determining transition state (TDTS) and TOF-determining intermediate (TDI), if TDTS appears after TDI in the reaction profile (equation 8a). When TDTS is followed by TDI, the reaction energy ($\Delta G_r$) is added to this difference (equation 8b). The assignments of a transition state as the TDTS and an intermediate as the TDI are made in a way that yields the highest energetic span $\delta E$ values possible for a given reaction profile. Among multiple possible reaction mechanisms, the fastest and thus the most feasible reaction pathway has the smallest energetic span $\delta E$ value. Once the TDI and TDTS are defined, equation 7 can be used to evaluate TOF along with the influence of reactant/product concentrations on the overall reaction rate. The concentration dependence is zero-order for all reactants or products entering or exiting catalytic cycle outside the turnover frequency-determining TDI-TDTS region. Therefore, comparison of predicted TOFs and concentration effects between individual DFT scenarios and against the experimental data provides a straightforward tool for validating the feasibility of a DFT-predicted reaction mechanism.

Figure 3:
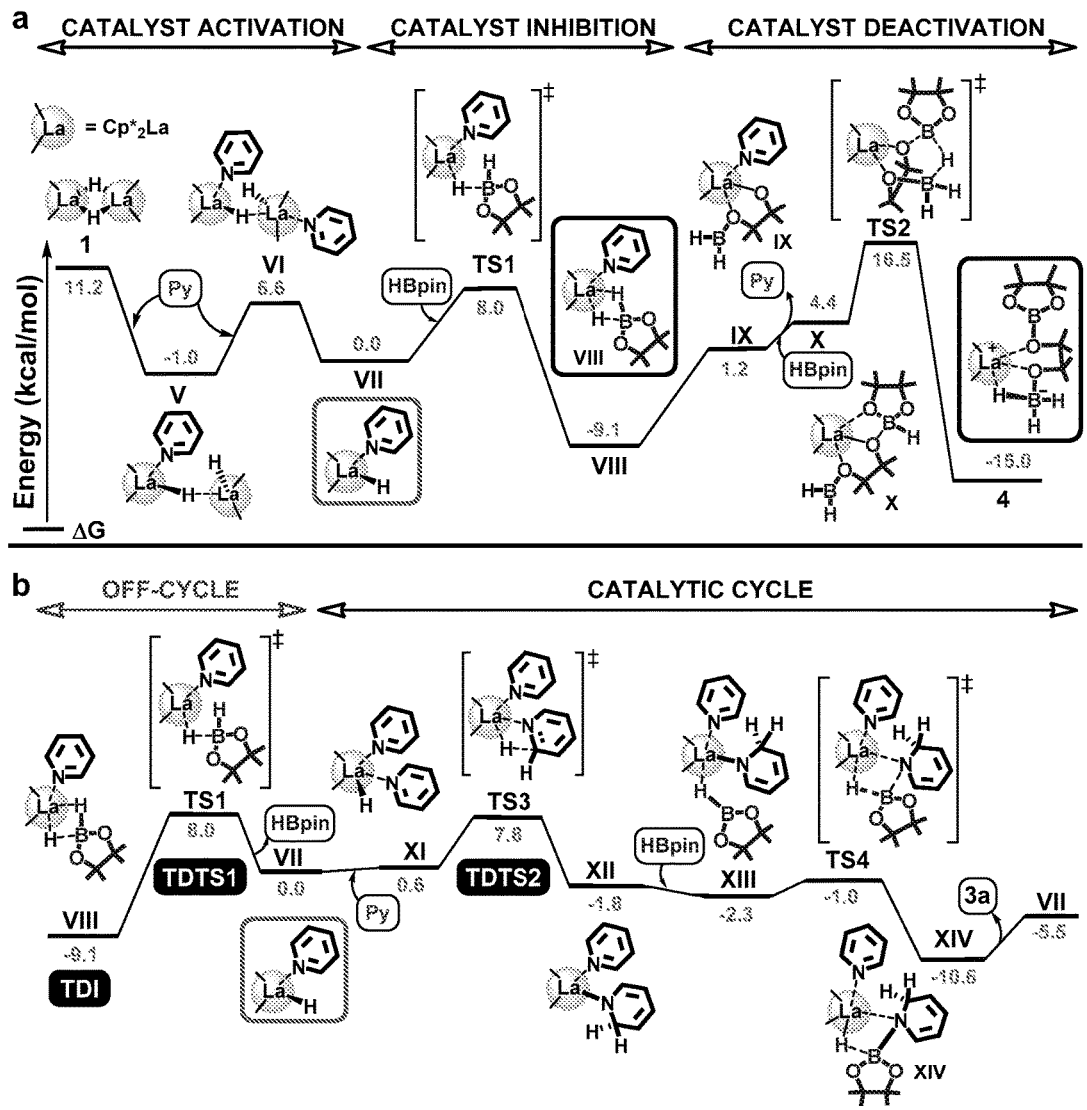
FIG. 3 depicts DFT-derived energetics of the catalytic pyridine dearomatization reaction coordinate; in particular a) energetic profile for transformations of precatalyst 1 in the presence of pyridine and HBpin: active catalyst generation, inhibition, and deactivation; b) energetic profile of the catalytic cycle for the $Cp_2^*La$-catalyzed pyridine dearomatization along with the off-cycle active catalyst inhibition process.

The active catalyst (see equations 1 and 2 above) and its competitive inhibition with HBpin (equation 4) is identified by combining the [Cp*$_2$LaH]$_2$ precatalyst 1 with multiple pyridine and/or HBpin molecules. It is found that complex 1 undergoes facile activation$^i$ to yield binuclear complexes V and VI via the pathway depicted in FIG. 3a (Wobser, S. D. et al., *Organometallics* 32, 1317-1327 (2013), incorporated herein by reference). In FIG. 3, all energies are Gibbs free energies in kcal/mol. The barrier-less first pyridine addition is particularly favored in saturating the Cp*$_2$La coordination sphere, while the second pyridine coordination is less stabilizing since the bridging hydride in V already saturates the other Cp*$_2$La-center. Finally, the energy required for adduct VI dissociation to produce monomeric VII is balanced by the entropic gain of the dissociation process. The overall 7.6 kcal/mol energetic barrier for the 1→VII process is in accord with the rapid activation observed experimentally. Next, the feasibility of a VII-HBpin interaction as in equation 5 is investigated. DFT exploration of several possibilities indicates a favorable interaction with $\Delta G$=-9.1 kcal/mol to form bidentate adduct VIII (TS1: 8.0 kcal/mol activation barrier). Intrigued by the formation of complex 4 (FIG. 2e, equation 5), possible B—O bond activation by adduct VIII is examined. Initial rearrangement yields pinacolate IX while addition of a second HBpin affords very stable, experimentally observed zwitterion 4 ($\Delta G$=-15.0 kcal/mol versus VII) via kinetically accessible TS2 (25.6 kcal/mol barrier). Zwitterion 4 formation observed in the stoichiometric experiment of FIG. 2e presumably occurs via a similar pathway wherein the pyridine role is played by the second HBpin molecule. It is seen as proposed that Cp*$_2$LaH(Py) is the active catalyst for the 1,2-hydroboration reaction and is in equilibrium with inhibition product VIII (equation 4), while zwitterion 4 is the final catalyst deactivation product (equation 5). Therefore, the sequence 1→VII →VIII→>4 corresponds to the catalyst activation, inhibition, and deactivation processes of the dearomatization cycle (FIG. 3a).

The mechanism of the pyridine dearomatization is probed by DFT and Energetic Span techniques. Scenarios considering only Cp*$_2$LaH(Py)$_n$ complexes with n=1 results in energetic profiles with relatively large energetic spans ($\delta E$>25 kcal/mol), implying very slow processes. In contrast, coordination of a second pyridine to the Cp*$_2$La center in VII to yield XI is found to be isoergonic and barrier-less, arguing for rapid equilibration between these two structures (FIG. 3b). Furthermore, the calculations indicate that it is the n=2 species XI that is the immediate precursor to the 1,2-dearomatization product in a low-energy span with one pyridine remaining coordinated to Cp*$_2$La through the entire catalytic cycle (FIG. 3b). As proposed above, starting from XI, the pyridine dearomatization occurs via intramolecular hydride transfer (1,2-addition/C=N insertion) to produce a stabilized Cp*$_2$La-1,2-dihydropyridine intermediate XII ($\Delta G$=−2.4 kcal/mol). This dearomatization step proceeds via four-center transition state TS3 in a concerted process (7.8 kcal/mol barrier) (Perrin, L. et al., Inorg Chem, 53, 6261-6373 (2014)). The relatively high TS3 energy is in accord with the experimental sluggishness of equation 2 (vide supra). Subsequent re-coordination of HBpin to XII yields isoenergetic intermediate XIII in which the HBpin B—H coordinates to the Cp*$_2$La-center. Next, XIII undergoes rapid, concerted La—N . . . H—B σ-bond metathesis to form stable product complex XIV ($\Delta G$=−8.3 kcal/mol) via four-centered transition state TS4 (1.3 kcal/mol barrier) as above (equation 3). Finally, dissociation of XIV requires $\Delta G$=5.1 kcal/mol to release product 3a and regenerate the active catalyst VII. It is noted that coordination of the second, "bystander" pyridine significantly lowers the barriers (by >8 kcal/mol) for both the 1,2-addition/C=N insertion and the σ-bond metathesis steps versus analogous processes involving only single-pyridine catalysts (n=1).

In parallel with the productive catalytic cycle (FIG. 3b, right), the off-cycle pathway (FIG. 3b, left) involves the aforementioned HBpin coordination to the active catalyst VII (8.0 kcal/mol free energy barrier) to generate a stable complex VIII ($\Delta G$=−9.1 kcal/mol). The barrier for this step at TS1 is comparable to that for the 1,2-addition/C=N insertion via TS3. Applying the Energetic Span model to the extended catalytic cycle outlined in FIG. 3b identifies complex VIII as the TDI and two energetically similar transition states TS1 and TS3 as the TDTSs (i.e., TDTS1 and TDTS2, respectively). Thus, the Energy Span δE evaluated from the profile in FIG. 3b is ~17.0 kcal/mol, and states TDI, TDTS1, and TDTS2 control the overall reaction kinetics via eqs. 7 and 8. Further examination shows that only HBpin exits the catalytic cycle between the TDI and TDTS1, while a pyridine molecule enters the catalytic cycle between TDI and TDTS2. In this way, the pyridine:HBpin concentration ratio dictates the TOF control exerted by TDTS1 (TS1) and TDTS2 (TS3). Specifically, at high pyridine concentrations the reaction rate is determined by TDTS1, with no pyridine entering the cycle in the TOF-determining TDI-TDTS1 zone, and thus the kinetic rate law becomes zero-order in pyridine (see equation 7). In contrast, both TDTS1 (TS1) and TDTS2 (TS3) influence the TOF at lower pyridine concentrations. The fraction of TOF control that is due to TDTS2 increases commensurate with the fall in pyridine concentration. Therefore, the rate law is expected to be first-order in pyridine concentration at low pyridine concentrations, zero-order at higher pyridine concentrations, and inverse first-order in HBpin concentration according to the equation 7, since HBpin is released in the TOF-determining zone. It is noted that these results are in excellent agreement with experiment and fully support the DFT-predicted mechanism. In addition, bond enthalpy estimations ($\Delta H_r$) for the dearomatization reaction predict net exothermicity of ~18 kcal/mol, which correlates well with the DFT computed $\Delta H_r^{DFT}$=17 kcal/mol. From FIG. 3, it is also evident that the overall reaction is driven by the energy released during the σ-bond metathesis step and strong B—N bond formation (XIII→XIV, $\Delta G$=−8.3 kcal/mol). Finally, extended Energetic Span calculations of nonstandard Gibbs energies($G^\circ$) for the reaction profile in FIG. 3 using the AUTOF program identify reversible and irreversible reaction steps. Specifically, intermediates having virtually identical nonstandard Gibbs energies exist in quasi-equilibrium. Thus, inhibition product VIII, active catalyst VII, and bis-pyridine complex XI are in equilibrium, and the same applies to the pairs of intermediates XII ↔ XIII and XIV ↔ VII. However, the pyridine dearomatization (XI→XII, $\Delta G^\circ$=−8.61 kcal/mol) and the σ-bond metathesis (XIII→XIV, $\Delta G^\circ$=−1.42 kcal/mol) steps are irreversible. In summary, the experimental and DFT mechanistic data are in good agreement and implicate active catalyst generation and 1,2 La—H bond addition to the pyridine C=N unsaturation as turnover-limiting (McSkimming, A. et al., Chem. Soc. Rev. 42, 5439-5488 (2013); Diaconescu, P. L., Acc. Chem. Res. 43, 1352-1363 (2010), both incorporated herein by reference).

Figure 4:
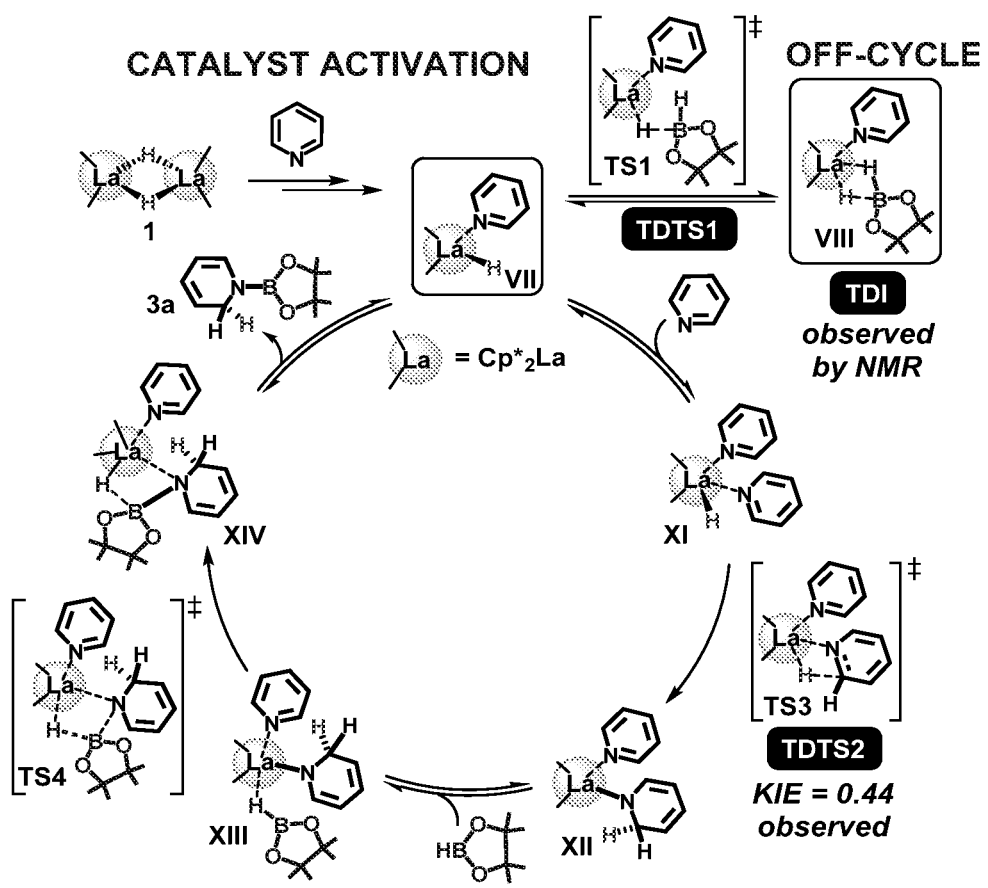
FIG. 4 is a mechanistic summary of catalytic pyridine dearomatization according to the invention.

Kinetic isotope effect (ME) measurements are performed to further probe the above mechanistic proposal. Comparison of the hydroboration reaction rates for pyridine versus pyridine-d$_5$ in the pseudo-first-order regime yield an inverse secondary KIE $k_H/k_D$=0.44±0.04, in accord with TOF-limiting 1,2-addition to the C=N functionality (e.g., TDTS2) rather than C—H scission. TDI structure VIII is one of the most energetically stable intermediates on the energetic profile, and hypothetically, could selectively be generated when no excesses of both pyridine and HBpin are present. In addition, evaluation of the catalytic species concentrations with the Extended Energetic Span model suggests that VIII represents ≥95% of all La species involved in the reaction. To test this hypothesis, studies of stoichiometric reactions between La-catalyst 1 and 1.0:1.0 pyridine: HBpin mixtures by in situ $^1$H NMR spectroscopy reveal disappearance of the La—H and B—H signals, displacement of the pyridine and Cp* signals, and emergence of a new multiplet corresponding to a La(μ-H)$_2$B functionality, consistent with structure VIII. Under these stoichiometric reaction conditions at 10° C., complex VIII undergoes decomposition release of the 1,2-dihydropyridine product. Furthermore, $^1$H NMR monitoring of the catalytic dearomatization reaction confirms the presence of complex VIII, validating its catalytic relevance. However, attempts to detect complex VIII after sequential additions to La-complex 1 of pyridine and then HBpin or vice versa indicate that the amounts are below the detection limits, further supporting the fidelity of this model. A summary of the proposed reaction mechanism including key findings from the Energetic Span model study is outlined in FIG. 4. Referring to FIG. 4, precatalyst activation, productive catalytic cycle, and off-cycle processes with the most relevant intermediates are depicted. The Energetic Span model affords mechanistic details, explains the observed rate law and reactivity trends, and guides experiments to locate the catalyst "resting state" and turnover-limiting transition states. In addition, the proposed mechanistic scenario is very different from the oxidative addition/reductive elimination sequence postulated for Rh-catalyzed processes. These differences stem from the appreciable lanthanide electrophilicity, non-dissociable supporting ligation, large ionic radii, resistance to two-electron reductive elimination, and very high kinetic lability (Jantunen, K. C. et al., J. Am. Chem. Soc. 128, 6322-6323 (2006); Edelmann, F T., Coord. Chem. Rev. 261, 73-155 (2014); and Minasian, S. G. et al., Chem. Eur. J. 17, 12234-12245 (2011), all of which are incorporated herein by reference).

Figure 5:
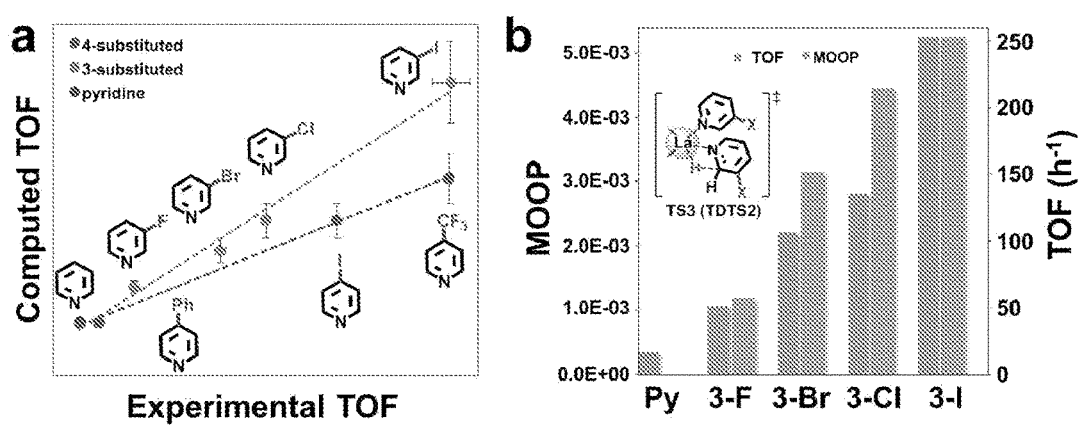
FIG. 5 shows DFT computed versus experimental organolanthanide-catalyzed turnover frequencies for functionalized pyridines; in particular a) trends as a function of pyridine substituents; b) correlation between experimental TOFs and positive Mulliken Orbital Overlap Population (MOOP) contributions due to halogen-$CH_2$ bonding interactions in the turnover—and regioselectivity—determining TS3 structures for a series of 3-halogen-substituted pyridines.

The present 3-functionalized pyridine 1,2-hydroboration (Table 2, entries 3k-o, 3q-s) of the invention is regioselective and intriguingly affords dearomatized products in which hydride is preferably delivered to the most hindered position. Similar regioselectivity was observed previously with Rh catalysts, however no explanation is provided. Hence, reactivities of several 3- and 4-substituted pyridines are investigated, as well as the unusual reactivity preference of the former by DFT/Energetic Span methodology. For the 4-substituted pyridines, calculations included iodo-, phenyl-, and trifluoromethyl-substituted pyridines, while entire halogen series (F, Cl, Br, I) is examined for 3-substituted substrates. Computed TOFs are obtained from equation 7 but neglecting the concentrations term and using the energetic span δE values from DFT. To simplify the DFT calculations, only TDI and TDTS2 energies (e.g., substituted analogs of TS3 and complex VIII; FIG. 3) are computed, with all other intermediates and transition states omitted. Even with such pragmatic approximations, linear correlations between experimental and computed TOF values are found for the 3- and 4-substituted pyridine series (FIG. 5a). Differences in slope between 3- and 4-substituted series are provisionally attributed to two distinct substituent effects. For the 4-substituted pyridines, the TOF trends track the substituent electron-withdrawing ability (Ph<I<CF$_3$). For the 3-functionalized substrates, inductive effects alone do not explain the experimental trends. Thus, a Mulliken Orbital Overlap Population (MOOP) analysis of the frontier orbitals (i.e., HOMO) of the TDTS2 structures is carried out to probe possible bonding (e.g., positive MOOP contribution), anti-bonding (negative), and nonbonding (zero) interactions (Glassey, W. V. et al., *J. Chem. Phys.* 113, 1698-1704 (2000), incorporated herein by reference). A through-bond interaction between the halogen and vicinal CH$_2$ group is evident for all TS3 (TDTS2) structures that lead to the 3-halo-1,2-dihydropyridine products (FIG. 5b). Furthermore, this interaction falls in the order I>Br>Cl>F, exactly reproducing the experimental TOF trend. Note however that a nonbonding interaction (zero MOOP value) is also located for the TS3 structures leading to the 5-halo-1,2-dihydropyridine regioisomers. That such products are not observed likely reflects the appreciable halogen-emerging CH$_2$ distances. Thus, these observations argue that halogen-CH$_2$ bonding interactions in the turnover- and regioselectivity-determining transition states (TS3, TDTS2) strongly influence the regioselectivity of 3-substituted pyridine dearomatization.

EXAMPLES OF THE INVENTION

Materials and Methods. Due to the air and moisture sensitivity of organolanthanide complex 1, all manipulations of air-sensitive materials are carried out with rigorous exclusion of O$_2$ and moisture in flame- or oven-dried Schlenk-type glassware on either a dual-manifold Schlenk line, interfaced to a high-vacuum manifold (10$^{-6}$ Torr), or in a N$_2$-filled MBraun glovebox with a high-capacity recirculator (<1 ppm O$_2$). Argon (Airgas) is purified by passage through a MnO column to remove O$_2$ and a column of Davison 4A molecular sieves to remove water immediately before use. Cyclohexane-d$_{12}$ (Cambridge Isotope Laboratories, 99+ atom % D) for NMR reactions and kinetic measurements is stored over Na/K alloy in vacuo and vacuum transferred before use. Pyridines are purchased from Sigma-Aldrich, TCI America, or Acros Organics, distilled from CaH$_2$, and stored under inert atmosphere in a glovebox. Liquid substrates and substrate solutions are degassed by freeze-pump-thaw methods. Solid substrates are purified by sublimation under high vacuum and are stored in a glovebox. Pinacolborane (HBpin) is purchased from TCI America, distilled and stored at −35° C. in a glovebox. The triphenylmethylsilane internal integration standard for kinetic NMR studies is purchased from Strem, sublimed under high-vacuum, and stored in the glove box. The precatalyst [Cp*$_2$LaH]$_2$ (1) is prepared as reported in the literature (Jeske, G. et al., *J. Am. Chem. Soc.* 107, 8091-8103 (1985), incorporated herein by reference). The following compounds are previously reported: 1-(4,4,5,5-tetramethyl-1,3,2-dioxaborolan-2-yl)-1,2-dihydropyridine (3a) (see Arrowsmith et al.), 1-(4,4,5,5-tetramethyl-1,3,2-dioxaborolan-2-yl)-4-(trifluoromethyl)-1,2-dihydropyridine (3b) (see Oshima et al.), 1-(4,4,5,5-tetramethyl-1,3,2-dioxaborolan-2-yl)-4-phenyl-1,2-dihydropyridine (3d) (see Arrowsmith et al.), 1-(4,4,5,5-tetramethyl-1,3,2-dioxaborolan-2-yl)-4-methyl-1,2-dihydropyridine (3f) (see Arrowsmith et al.), 1-(4,4,5,5-tetramethyl-1,3,2-dioxaborolan-2-yl)-3-fluoro-1,2-dihydropyridine (3k) (see Oshima et al.), 1-(4,4,5,5-tetramethyl-1,3,2-dioxaborolan-2-yl)-3-methyl-1,2-dihydropyridine (3o) (see Arrowsmith et al.), 1-(4,4,5,5-tetramethyl-1,3,2-dioxaborolan-2-yl)-3-methoxy-1,2-dihydropyridine (3r) (see Oshima et al.), 1-(4,4,5,5-tetramethyl-1,3,2-dioxaborolan-2-yl)-1,2-dihydroquinoline (3t) (see Arrowsmith et al.), 1-(4,4,5,5-tetramethyl-1,3,2-dioxaborolan-2-yl)-1,2-dihydroisoquinoline (3u) (see Arrowsmith et al.), 1,4-Bis(4,4,5,5-tetramethyl-1,3,2-dioxaborolan-2-yl)-1,2,3,4-tetrahydropyrazine (3v) (see Oshima II).

Physical and Analytical Measurements. NMR spectra are recorded on Agilent HCN600 (DDR2, FT, 500 MHz, $^1$H; 125 MHz, $^{13}$C), Agilent F500 (DDR2, FT, 500 MHz, $^1$H; 125 MHz, $^{13}$C; 160 MHz, $^{11}$B, 376 MHz, $^{19}$F), Varian UNITYInova-500 (FT, 500 MHz, $^1$H; 125 MHz, $^{13}$C), Agilent Au400 (DDR2, FT, 400 MHz, $^1$H; 100 MHz, $^{13}$C; 128 MHz, $^{11}$B), or Bruker Avance III 500 (direct cryoprobe, 500 MHz, $^1$H; 125, $^{13}$C) instruments. Chemical shifts for $^1$H and $^{13}$C spectra are referenced using internal solvent resonances and are reported relative to tetramethylsilane (TMS). BF$_3$·OEt$_2$ is used as an external reference for $^{11}$B NMR spectra. NMR experiments on air-sensitive samples are conducted in Teflon-valve-sealed sample tubes (J. Young). High-resolution mass spectra (HRMS) are acquired on an Agilent 6210 LC-TOF (ESI, APCI, APPI) mass spectrometer with acetonitrile as the solvent in the positive ion mode.

Procedure for Typical NMR-Scale Catalytic Reactions. In a glove box, 100 µL of a solution of the catalyst 1 (C$_6$D$_{12}$, 0.025 M, 2.5 µmol) and 150 µL of C$_6$D$_{12}$ are added to a J. Young NMR tube. Triphenylmethylsilane (15.0 mg, 54 µmol) is weighed out in a 4 mL vial that is then closed with a cap equipped with s septum. Next, 500 µL of a solution of pyridine (C$_6$D$_{12}$, 0.5 M, 250 µmol) and 500 µL of a solution of HBpin (C$_6$D$_{12}$, 0.5 M, 250 µmol) are added to the vial, thoroughly mixed, and subsequently transferred to the J. Young NMR tube. The tube is sealed immediately, quickly removed from the glove box, and placed into a dry ice/acetone bath, where it is maintained at −78° C. until just before the NMR experiment. At this point, it is thawed, shaken, and immediately placed in the pre-heated and temperature-calibrated by an ethylene glycol standard (±0.3° C.) probe of the NMR spectrometer. Single pulse $^1$H NMR spectra are taken at regular intervals. Substrate and/or product concentrations are determined relative to the intensity of the internal standard resonance plotted versus time.

Kinetic Analysis. Kinetic analysis of the NMR-scale reactions described above is carried out by collecting multiple (>30) data points early in the reaction before the substrate concentrations are appreciably depleted (Ansyln, E. V. et al., *Modern Physical Organic Chemistry*. (University Science, 2006); Espenson, J. H., *Chemical Kinetics and Reaction Mechanisms*. 2nd edn, (McGraw-Hill, Inc, 2002);

and Pilling, M. J. & Seakins, P. W. *Reaction Kinetics.* (Oxford University Press, 1995), all of which are incorporated herein by reference). Under these conditions, the reaction is approximated as pseudo-zero-order with respect to the substrate concentrations. A long pulse delay is used during data acquisition to avoid saturation. The kinetic data are usually obtained from intensity changes in the dearomatized 1,2-dihydropyridine-α-H integral or the substrate pyridine-α-H resonance integral over 3 or more half-lives. The product concentration is measured from the area of the dearomatized 1,2-dihydropyridine-α-H peak, $A_s$, standardized to $A_1$, the methyl peak area of the $Ph_3SiMe$ internal standard. Data are fit by least-squares analysis ($R^2$>0.98) according to equation 9, where t is time and [product] is the concentration of product at time t. The turnover frequency (TOF, $h^{-1}$) is calculated from the least-squares determined slope (m) according to equation 10 where [catalyst]$_0$ is the initial concentration of the catalyst 1. A 0.025 M stock solution of 1 is prepared in the glove box by dissolving 0.205 g (0.25 mmol) of 1 in 10 mL of $C_6D_{12}$. The mixture is stirred until 1 is completely dissolved. The solution is stored in a sealed storage tube at 0° C. prior to use).

$$[\text{product}] = mt \tag{9}$$

$$TOF(h^{-1}) = \frac{60 \text{ min}}{h} \times \frac{m}{[\text{catalyst}]_0} \tag{10}$$

Figure 6:
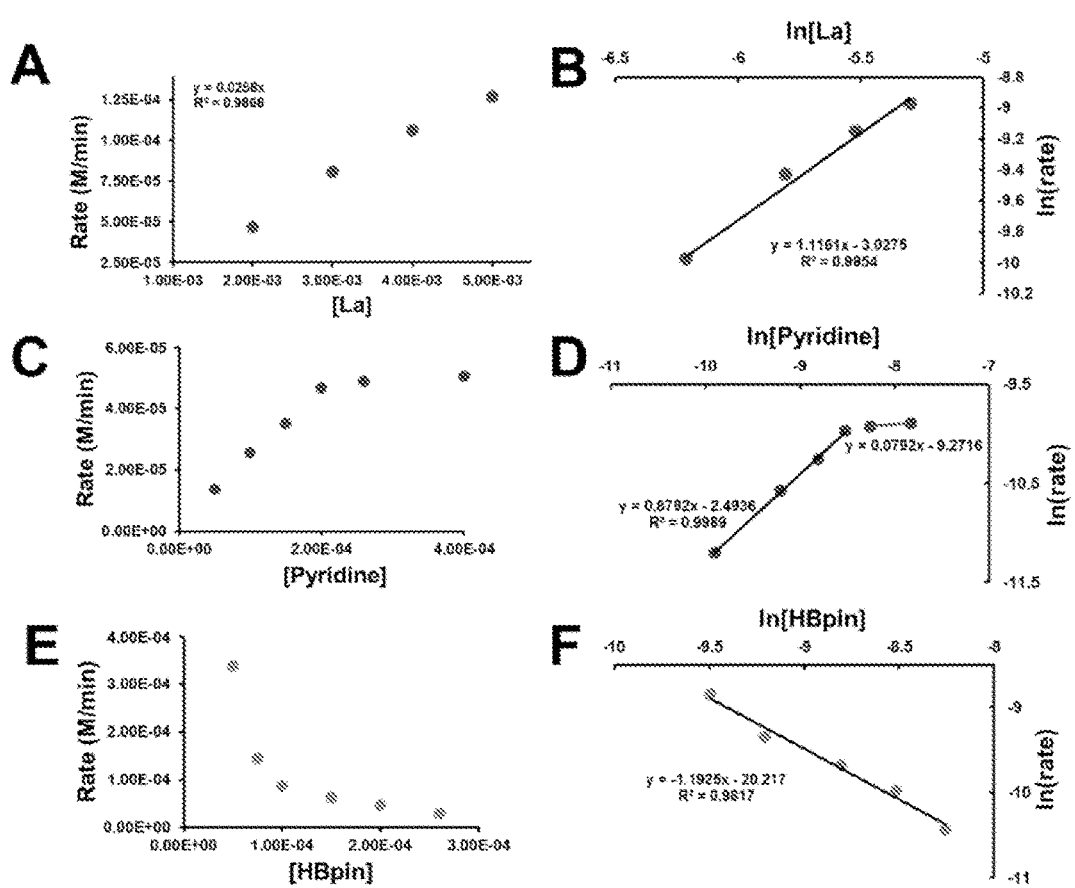
FIG. 6 a) is a plot of $[catalyst]_0$ vs. reaction rate (M/min); b) van't Hoff plot for reaction rate law order in $[catalyst]_0$; c) plot of [pyridine] vs. rate (M/min); d) van't Hoff plot for reaction rate law order in [pyridine]; e) Plot of [HBpin] vs. rate(M/min); f) van't Hoff plot for reaction rate law order in [HBpin].

Referring to FIG. 6, FIG. 6a is a plot of [catalyst]$_0$ vs. reaction rate (M/min). FIG. 6b is a van't Hoff plot for reaction rate law order in [catalyst]$_0$. FIG. 6c is a plot of [pyridine] vs. rate (M/min) FIG. 6d is a van't Hoff plot for reaction rate law order in [pyridine]. FIG. 6e is a plot of [HBpin] vs. rate(M/min) FIG. 6f is a van't Hoff plot for reaction rate law order in [HBpin]. 25% [HBpin] point is excluded from the van't Hoff plot due to the very fast reaction (27% conversion after ~3 min).

Figure 7:
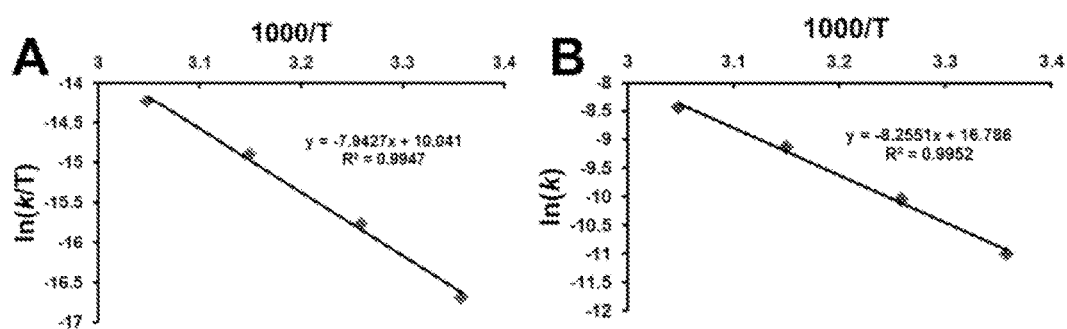
FIG. 7 a) is an Erying plot (equation 11) and b) is an Arrhenius plot (equation 12) with the line as the least-squares fit to the data points.
Figure 8:
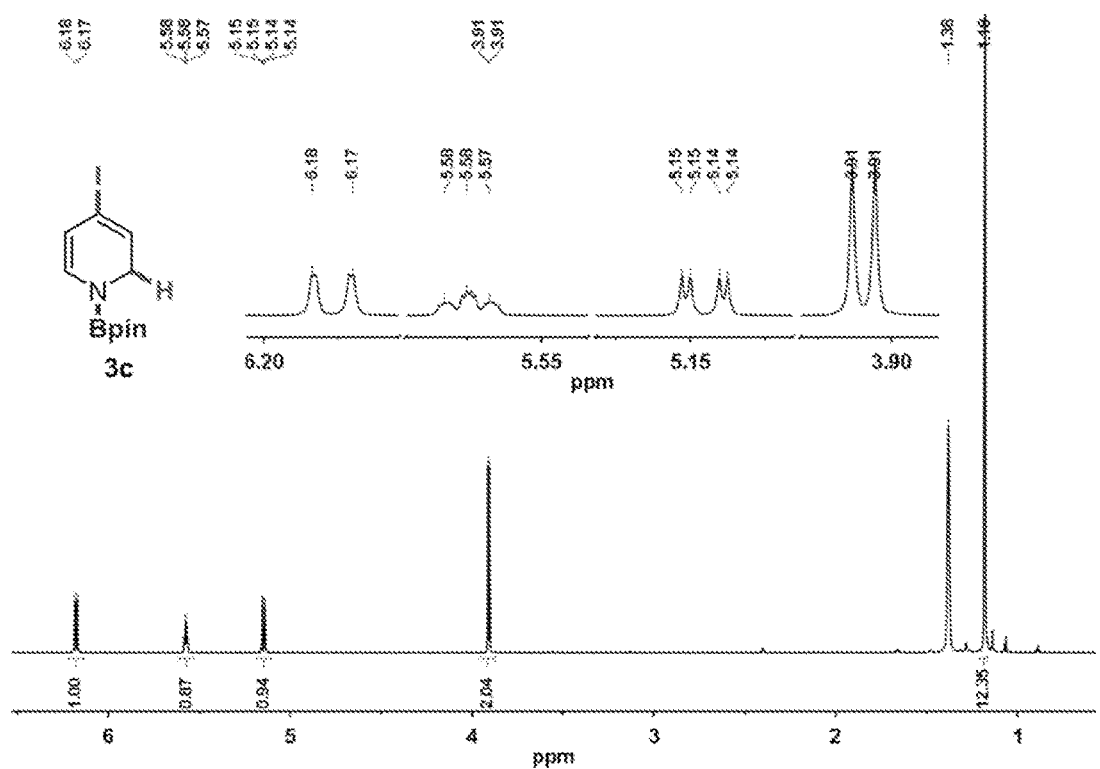
FIG. 8 is a $^1H$ NMR spectrum of 3c in $C_6D_{12}$.

Activation Parameters. Eyring and Arrhenius plots for the reaction between pyridine and HBpin are plotted according to equation 11 and 12 respectively, where k is calculated by the least-square slope (m) according to equation 9. An Erying plot (equation 11) and an Arrhenius plot (equation 12) is provided in FIGS. 7a and 7b, respectively.

$$\ln\left(\frac{k}{T}\right) = -\frac{\Delta H^*}{RT}\left[\frac{\Delta I^*}{R} - \ln\left(\frac{h}{k_b}\right)\right] \tag{11}$$

$$\ln(k) = -\frac{E_a}{RT} + \ln A \tag{12}$$

glove box, and stirred at 35° C. for 2 hours in an oil bath. Then, the volatiles are removed in vacuo and the solid redissolved in pentane (15 mL). The solution is then cannula filtered into a pre-weighed Schlenk flask and evaporated, yielding 0.72 g (87% yield) of 1-(4,4,5,5-tetramethyl-1,3,2-dioxaborolan-2-yl)-1,2-dihydropyridine (3c) that is pure by $^1$H NMR (see FIG. 8).

Spectroscopic Characterization of 1,2-Dihydropyridines.

1-(4,4,5,5-tetramethyl-1,3,2-dioxaborolan-2-yl)-1,2-dihydropyridine (3a): $^1$H NMR (500 MHz, $C_6D_6$): δ=6.72 (d, J=7.4 Hz, 1H), 5.79 (m, 1H), 5.10 (m, 1H), 4.17 (d, J=4.1 Hz, 2H), 1.01 (s, 12H) ppm.

1-(4,4,5,5-tetramethyl-1,3,2-dioxaborolan-2-yl)-4-(trifluoromethyl)-1,2-dihydropyridine 3b): $^1$H NMR (500 MHz, $C_6D_{12}$): δ=6.45 (d, J=7.5 Hz, 1H), 5.53 (s, 1H), 5.04 (d, J=7.5 Hz, 1H), 4.04 (s, 2H), 1.19 (s, 12H) ppm.

1-(4,4,5,5-tetramethyl-1,3,2-dioxaborolan-2-yl)-4-phenyl-1,2-dihydropyridine (3d): $^1$H NMR (500 MHz, $C_6D_{12}$): δ=7.34-7.03 (m, 5H), 6.50 (d, J=7.3 Hz, 1H), 5.32 (m, 2H), 4.09 (s, 2H), 1.18 (s, 12H) ppm.

1-(4,4,5,5-tetramethyl-1,3,2-dioxaborolan-2-yl)-4-methyl-1,2-dihydropyridine (3f): $^1$H NMR (500 MHz, $C_6D_{12}$): δ=6.29 (d, J=7.4 Hz, 1H), 4.83 (s, 1H), 4.78 (d, J=7.4 Hz, 1H), 3.89 (s, 2H), 1.59 (s, 3H) 1.18 (s, 12H) ppm.

1-(4,4,5,5-tetramethyl-1,3,2-dioxaborolan-2-yl)-3-fluoro-1,2-dihydropyridine (3k): $^1$H NMR (500 MHz, $C_6D_{12}$): δ=6.07 (d, J=7.2 Hz, 1H), 5.23 (dd, J=11.4 Hz, J=6.2 Hz, 1H), 4.69 (d, J=5.9 Hz, 1H), 4.10 (s, 2H), 1.19 (s, 12H).

1-(4,4,5,5-tetramethyl-1,3,2-dioxaborolan-2-yl)-3-methyl-1,2-dihydropyridine (3o): $^1$H NMR (500 MHz, $C_6D_{12}$): δ=6.17 (d, J=7.4 Hz, 1H), 5.43 (s, 1H), 4.80 (t, J=6.5 Hz, 1H), 3.89 (s, 2H), 1.58 (s, 3H), 1.19 (s, 12H).

1-(4,4,5,5-tetramethyl-1,3,2-dioxaborolan-2-yl)-3,5-methyl-1,2-dihydropyridine (3p): $^1$H NMR (500 MHz, $C_6D_{12}$): δ=6.97 (s, 1H), 5.35 (s, 1H), 3.79 (s, 2H), 1.60 (s, 3H), 1.58 (s, 3H), 1.17 (s, 12H) ppm.

1-(4,4,5,5-tetramethyl-1,3,2-dioxaborolan-2-yl)-3-methoxy-1,2-dihydropyridine (3r): $^1$H NMR (500 MHz, $C_6D_{12}$): δ=6.02 (d, J=7.2 Hz, 1H), 4.85 (t, J=6.7 Hz, 1H), 4.74 (d, J=6.1 Hz, 1H), 3.91 (s, 1H), 3.73 (s, 2H), 3.46 (s, 3H), 1.18 (s, 12H) ppm.

(4,4,5,5-tetramethyl-1,3,2-dioxaborolan-2-yl)-1,2-dihydroquinoline (3t): $^1$H NMR (500 MHz, $C_6D_{12}$): δ=6.92-6.70 (m, 4H), 6.25 (d, J=9.5 Hz, 1H), 5.68 (m, 1H), 4.01 (s, 2H), 1.17 (s, 12H) ppm.

(4,4,5,5-tetramethyl-1,3,2-dioxaborolan-2-yl)-1,2-dihydroisoquinoline (3u): $^1$H NMR (500 MHz, $C_6D_{12}$): δ=6.97-6.76 (m, 4H), 6.49 (s, 1H), 5.50 (s, 1H), 4.35 (s, 2H), 1.18 (s, 12H) ppm.

1,4-Bis(4,4,5,5-tetramethyl-1,3,2-dioxaborolan-2-yl)-1,2,3,4-tetrahydropyrazine (3v): $^1$H NMR (500 MHz, $C_6D_{12}$): δ=5.59 (s, 2H), 3.24 (s, 4H), 1.15 (s, 24H) ppm.

Figure 9:
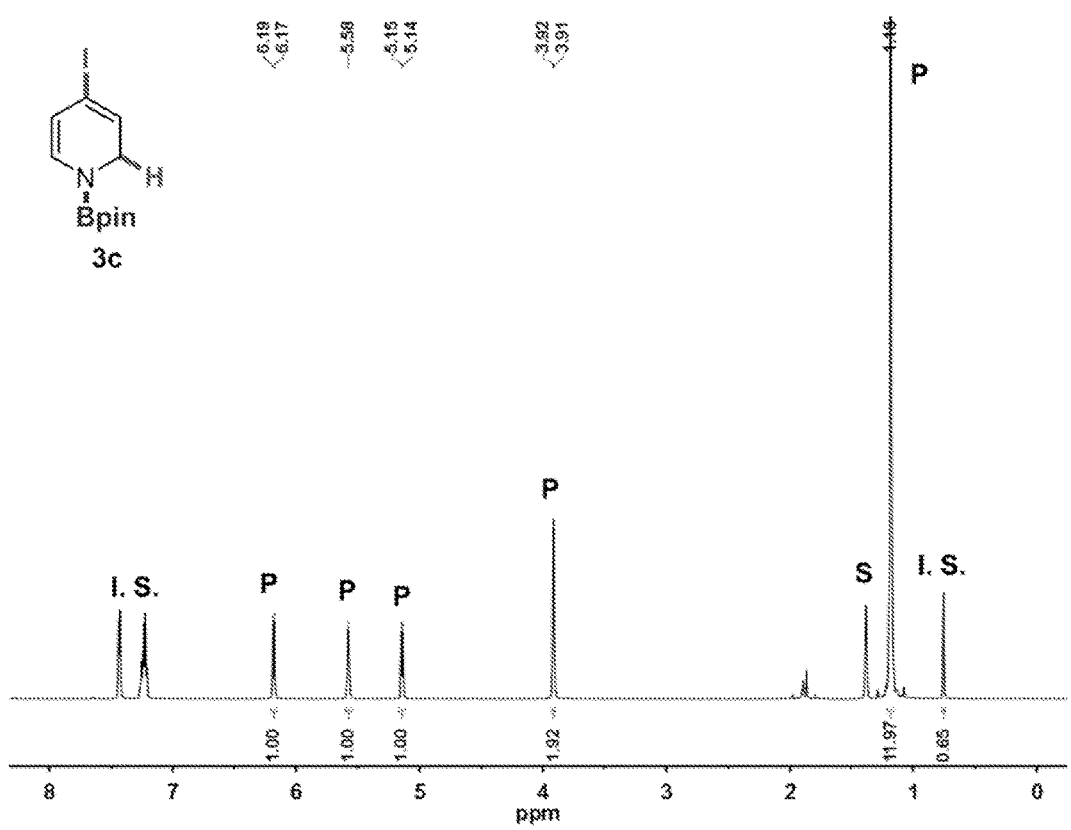
FIG. 9 is a $^1H$ NMR spectrum of 3c in $C_6D_{12}$, wherein P=product; I. S.=internal standard; and S=solvent.

1-(4,4,5,5-tetramethyl-1,3,2-dioxaborolan-2-yl)-4-iodo-1,2-dihydropyridine (3c). 1H NMR (600 MHz, $C_6D_{12}$): δ=6.18 (d, J=7.5 Hz, 1H), 5.57 (s, 1H), 5.15 (d, J=7.5 Hz, 1H), 3.92 (d, J=4.5 Hz, 2H), 1.18 (s, 12H) ppm. $^{13}$C NMR (125 MHz, $C_6D_{12}$): δ=134.1, 122.1, 111.7, 88.9, 83.7, 45.5, 25.0 ppm. $^{11}$B NMR (128 MHz, $C_6D_{12}$): δ=23.2 ppm. HRMS (LC-TOF, positive mode, $CH_2Cl_2/CH_3CN$): m/z calcd for $C_{11}H_{17}BINO_2$: 333.04. found: 334.134 (M-H$^+$) (FIG. 9).

Figure 10:
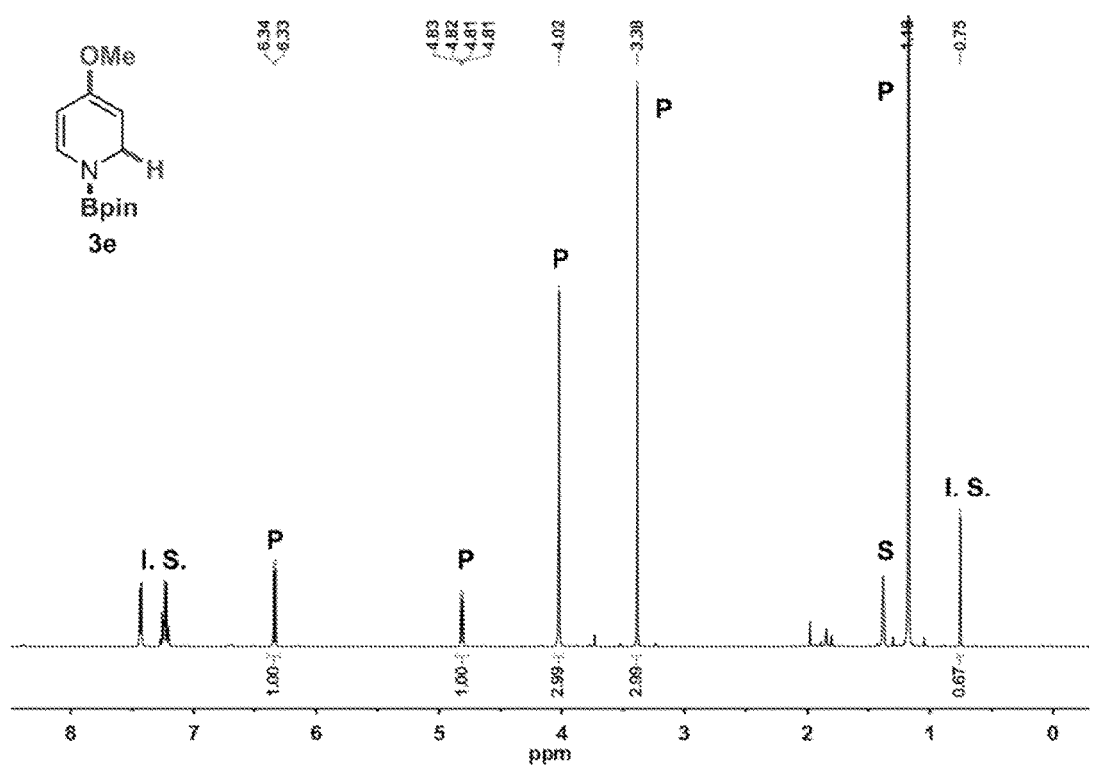
FIG. 10 is a $^1H$ NMR spectrum of 3e in $C_6D_{12}$, wherein P=product; I. S.=internal standard; and S=solvent.

1-(4,4,5,5-tetramethyl-1,3,2-dioxaborolan-2-yl)-4-methoxy-1,2-dihydropyridine (3e). $^1$H NMR (500 MHz, $C_6D_{12}$): δ=6.3 (d, J=7.75 Hz, 1H), 4.81 (dd, $J^1$=7.75 Hz, $J^2$=1.95 Hz, 1H), 4.02 (s, 3H), 3.38 (s, 3H), 1.18 (s, 12H) ppm. $^{13}$C NMR (125 MHz, $C_6D_{12}$): δ=134.7, 109.7, 102.2, 83.3, 82.2, 53.7, 42.8, 25.0 ppm. $^{11}$B NMR (128 MHz, $C_6D_{12}$): δ=23.6 ppm. HRMS (LC-TOF, positive mode, $CH_2Cl_2/CH_3CN$): m/z calcd for $C_{12}H_{20}BNO_3$: 237.11. found: 238.149 (M-H') (FIG. 10).

Figure 11:
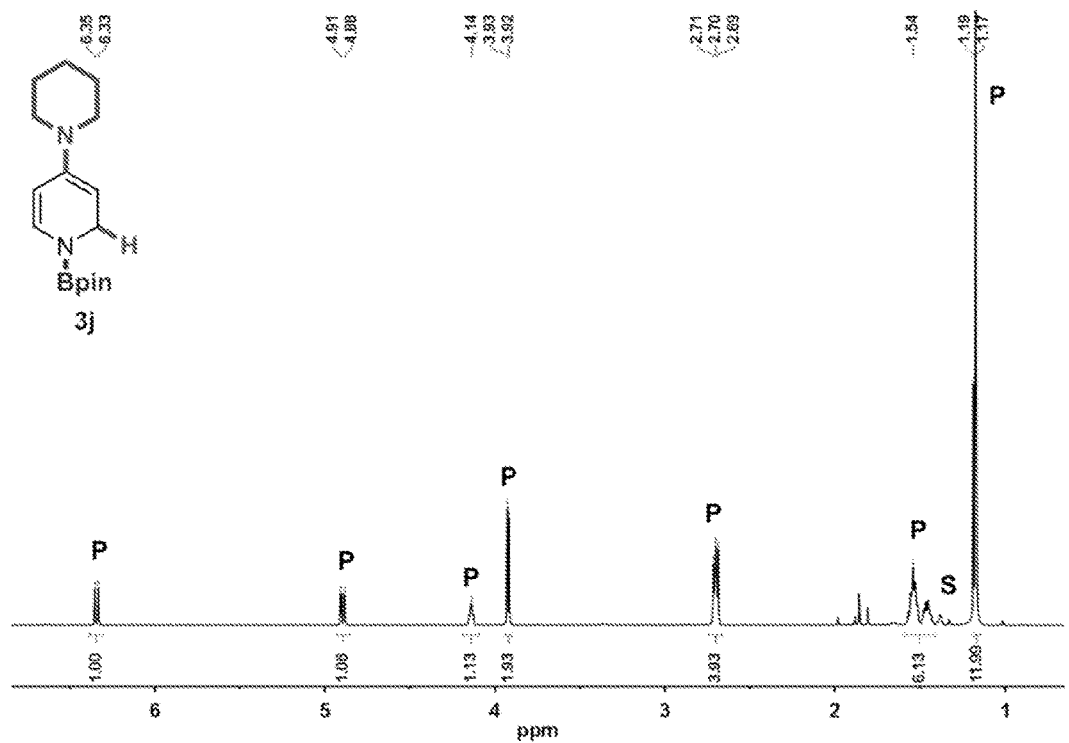
FIG. 11 is a $^1H$ NMR spectrum of 3j in $C_6D_{12}$, wherein P=product; and S=solvent.

1-(4,4,5,5-tetramethyl-1,3,2-dioxaborolan-2-yl)-4-piperidino-1,2-dihydropyridine (3j). $^1$H NMR (500 MHz, $C_6D_6$): δ=6.34 (d, J=7.8 Hz, 1H), 4.89 (dd, $^1$J=7.8 Hz, $^2$J=2.25 Hz, 1H), 4.14 (q, 1H), 3.93 (d, $^1$J=4.2 Hz, 2H), 2.70 (m, 4H), 1.54 (m, 4H), 1.68 (s, 2H), 1.17 (s, 12H) ppm. $^{13}$C NMR (125 MHz, $C_6D_6$): δ=145.6, 132.7, 102.2, 89.2, 82.1, 49.7, 42.1, 26.5, 24.6, 24.1 ppm. $^{11}$B NMR (128 MHz, $C_6D_6$): δ=23.5 ppm. HRMS (LC-TOF, positive mode, $CH_2Cl_2/CH_3CN$): m/z calcd for $C_{16}H_{27}BN_2O_2$ 290.22. found: 291.223 (M-H') (FIG. 11).

Figure 12:
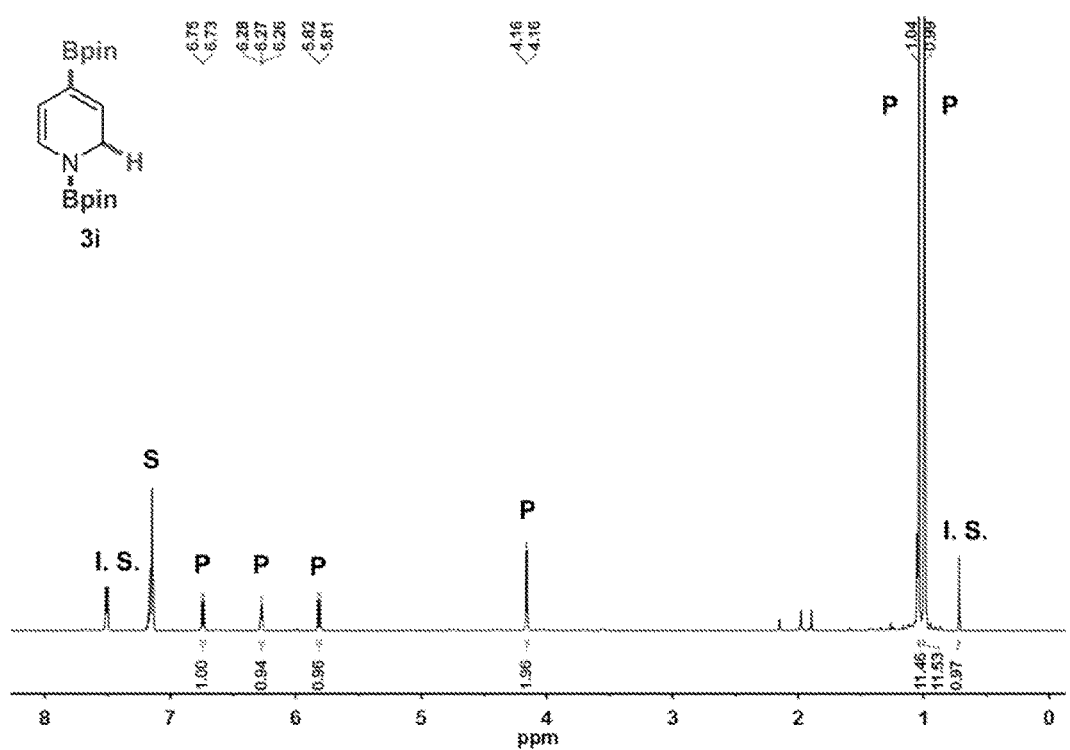
FIG. 12 is a $^1H$ NMR spectrum of 3i in $C_6D_{12}$, wherein P=product; I. S.=internal standard; and S=solvent.

1-(4,4,5,5-tetramethyl-1,3,2-dioxaborolan-2-yl)-4-(4,4,5,5-tetramethyl-1,3,2-dioxaborolan-2-yl)-1,2-dihydropyridine (3i). $^1$H NMR (500 MHz, C$_6$D$_6$): δ=6.74 (d, J=7.3 Hz, 1H), 6.31 (t, J=4.4 Hz, 1H), 5.81 (d, J=7.3 Hz, 1H), 4.16 (d, J=4.4 Hz, 2H), 1.04 (s, 12H), 0.99 (d, 12H) ppm. $^{13}$C NMR (125 MHz, C$_6$D$_6$): δ=131.1, 128.8, 128.0, 106.1, 82.9, 82.7, 42.6, 24.5, 24.3 ppm. $^{11}$B NMR (128 MHz, C$_6$D$_6$): δ=28.4, 23.6 ppm. HRMS (LC-TOF, positive mode, CH$_2$Cl$_2$/CH$_3$CN): m/z calcd for C$_{17}$H$_{29}$B$_2$NO$_4$ 333.23. found: 334.221 (M-H$^+$) (FIG. 12).

Figure 13:
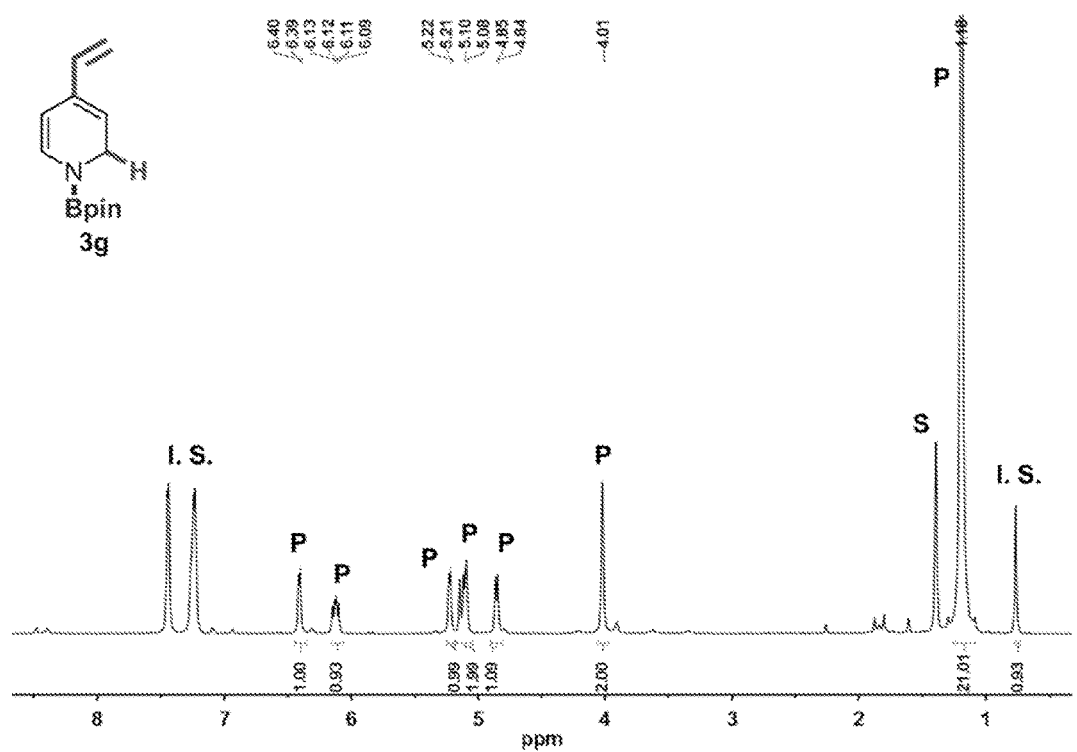
FIG. 13 is a $^1H$ NMR spectrum of 3g in $C_6D_{12}$, wherein P=product; I. S.=internal standard; and S=solvent.

1-(4,4,5,5-tetramethyl-1,3,2-dioxaborolan-2-yl)-4-vinyl-1,2-dihydropyridine (3g). $^1$H NMR (500 MHz, C$_6$D$_{12}$): δ=. 6.39 (d, J=7.0 Hz, 1H), 6.11 (dd, J=9.2 Hz, J=4.9 Hz, 1H), 5.22 (d, J=7.0 Hz, 1H), 5.1 (m, 2H), 4.85 (d, J=9.2 Hz, 1H), 4.01 (s, 2H), 1.18 (s, 12H) ppm. $^{13}$C NMR (125 MHz, C$_6$D$_{12}$): δ=150.9, 136.0, 120.7, 117.4, 111.0, 100.2, 83.1, 43.1, 25.3 ppm. $^{11}$B NMR (128 MHz, C$_6$D$_{12}$): δ=28.2 ppm. HRMS (LC-TOF, positive mode, CH$_2$Cl$_2$/CH$_3$CN): m/z calcd for C$_{13}$H$_{20}$BNO$_2$ 233.16. found: 234.144 (M-H$^+$) (FIG. 13).

Figure 14:
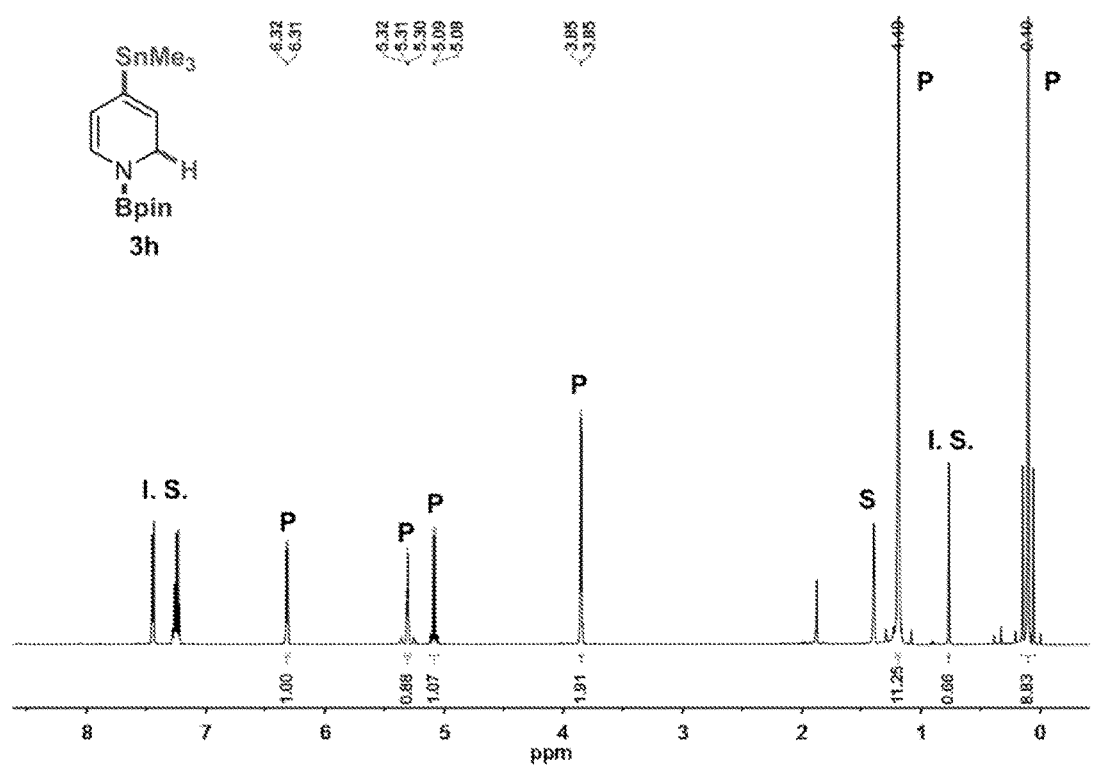
FIG. 14 is a $^1H$ NMR spectrum of 3h in $C_6D_{12}$, wherein P=product; I. S.=internal standard; and S=solvent.

1-(4,4,5,5-tetramethyl-1,3,2-dioxaborolan-2-yl)-4-trimethylstannyl-1,2-dihydropyridine (3h). $^1$H NMR (500 MHz, C$_6$D$_{12}$): δ=6.31 (d, J=7.1 Hz, 1H), 5.29 (t, J=4.2 Hz, 1H), 5.09 (d, J=7.1 Hz, 1H), 3.85 (d, J=4.2 Hz, 2H), 1.19 (s, 12H), 0.10 (s, 9H) ppm. $^{13}$C NMR (125 MHz, C$_6$D$_{12}$): δ=148.6, 130.4, 122.2, 108.0, 82.2, 42.0, 24.1, −11.2 ppm. $^{11}$B NMR (128 MHz, C$_6$D$_{12}$): δ=34.1 ppm. $^{119}$Sn NMR (128 MHz, C$_6$D$_{12}$): δ=−32.4 ppm. HRMS (LC-TOF, positive mode, CH$_2$Cl$_2$/CH$_3$CN): m/z calcd for C$_{14}$H$_{26}$BNO$_2$Sn, 371.11. found: 372.100 (M-H$^+$) (FIG. 14).

Figure 15:
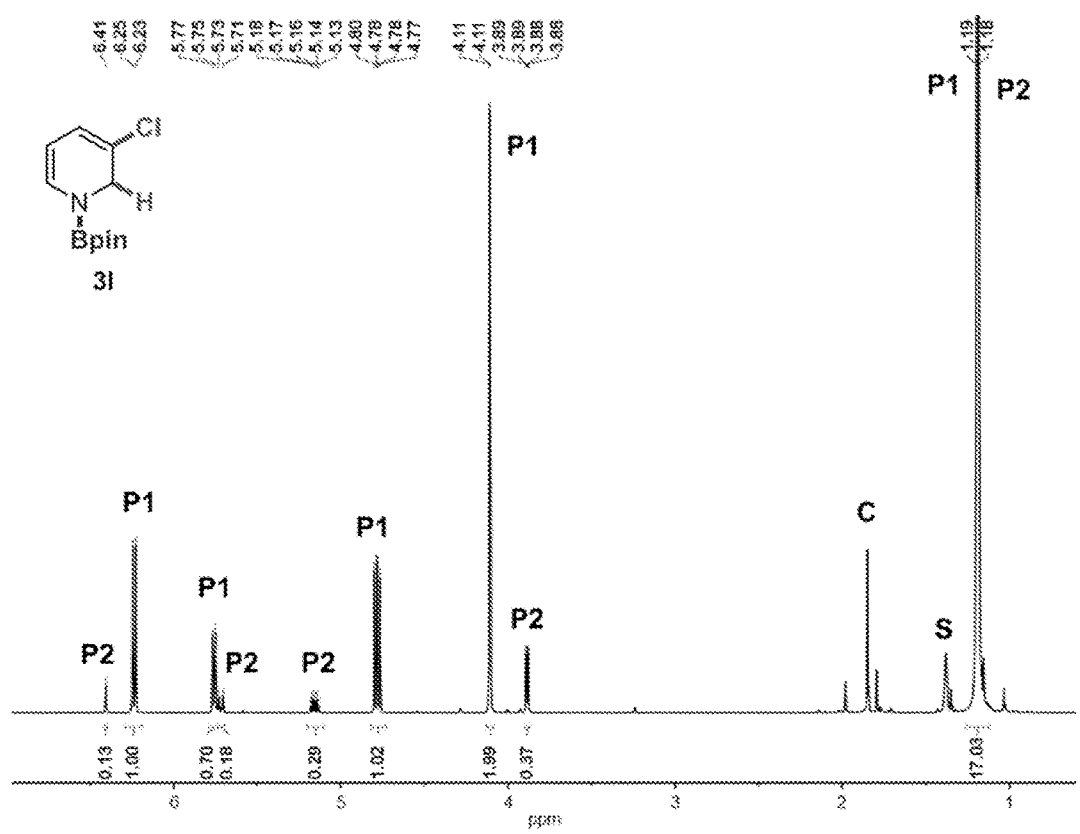
FIG. 15 is a $^1H$ NMR spectrum of 3l in $C_6D_{12}$, wherein P1=3-chloro-1,2-dihydropyridine; P2=5-chloro-1,2-dihydropyridine; C=catalyst; and S=solvent.

1-(4,4,5,5-tetramethyl-1,3,2-dioxaborolan-2-yl)-3-chloro-1,2-dihydropyridine and 1-(4,4,5,5-tetramethyl-1,3,2-dioxaborolan-2-yl)-5-chloro-1,2-dihydropyridine (3l). 3-chloro-1,2-dihydropyridine: $^1$H NMR (500 MHz, C$_6$D$_{12}$): δ=6.24 (d, J=7.3 Hz, 1H), 5.76 (m, 1H), 4.78 (dd, J=7.3 Hz, J=6.1 Hz 1H), 4.11 (d, J=1.4 Hz, 2H), 1.19 (s, 12H) ppm. 5-chloro-1,2-dihydropyridine: $^1$H NMR (500 MHz, C$_6$D$_{12}$): δ=6.41 (s, 1H), 5.72 (m, 1H), 5.15 (m, 1H), 3.88 (dd, J=4.3 Hz, J=1.7 Hz 2H), 1.18 (s, 12H) ppm. $^{13}$C NMR (125 MHz, C$_6$D$_{12}$): δ=150.5, 148.7, 131.2, 130.6, 121.8, 120.7, 116.6, 101.9, 84.3, 84.2, 49.4, 42.7, 25.6, 25.5 ppm. $^{11}$B NMR (128 MHz, C$_6$D$_{12}$): δ=23.7 ppm. HRMS (LC-TOF, positive mode, CH$_2$Cl$_2$/CH$_3$CN): m/z calcd for C$_{11}$H$_{17}$BClNO$_2$ 241.52. found: 242.099 (M-H$^+$) (FIG. 15).

Figure 16:
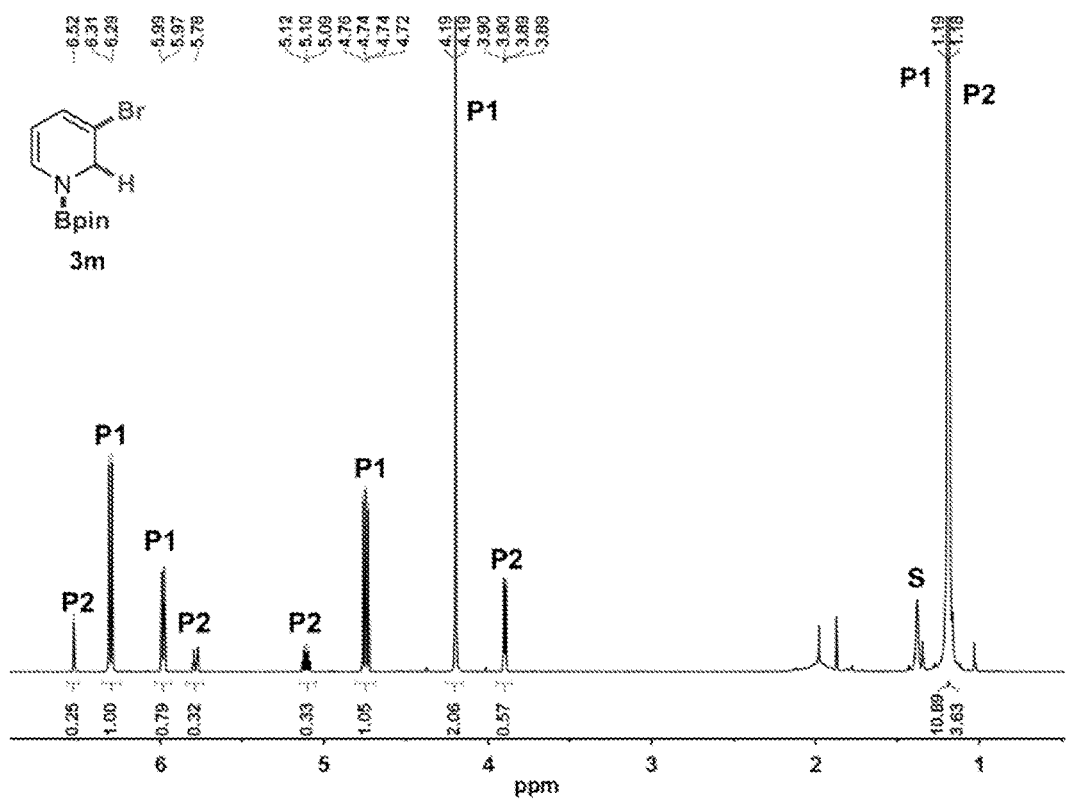
FIG. 16 is a $^1H$ NMR spectrum of 3m in $C_6D_{12}$, wherein P1=3-bromo-1,2-dihydropyridine; P2=5-bromo-1,2-dihydropyridine; and S=solvent.

1-(4,4,5,5-tetramethyl-1,3,2-dioxaborolan-2-yl)-3-bromo-1,2-dihydropyridine and 1-(4,4,5,5-tetramethyl-1,3,2-dioxaborolan-2-yl)-5-bromo-1,2-dihydropyridine (3m). 3-bromo-1,2-dihydropyridine: $^1$H NMR (500 MHz, C$_6$D$_6$): δ=6.30 (d, J=7.26 Hz, 1H), 5.98 (m, 1H), 4.74 (dd, J=7.26 Hz, J=1.4 Hz, 1H), 4.20 (d, J=1.4 Hz, 2H), 1.19 (s, 12H) ppm. $^{13}$C NMR (125 MHz, C$_6$D$_6$): δ=132.6, 124.2, 114.9, 103.8, 83.1, 42.5, 24.7. 5-bromo-1,2-dihydropyridine: $^1$H NMR (500 MHz, C$_6$D$_6$): δ=6.52 (s, 1H), 5.78 (m, 1H), 5.11 (m, 1H), 3.90 (m, 2H), 1.18 (s, 12H). $^{13}$C NMR (125 MHz, C$_6$D$_6$): δ=132.7, 131.2, 128.8, 125.4, 116.0, 102.0, 97.3, 83.7, 50.5, 41.8, 25.0 ppm. $^{11}$B NMR (128 MHz, C$_6$D$_6$): δ=23.6 ppm. HRMS (LC-TOF, positive mode, CH$_2$Cl$_2$/CH$_3$CN): m/z calcd for C$_{11}$H$_{17}$BBrNO$_2$ 285.05. found: 286.11 (M-H$^+$) (FIG. 16).

Figure 17:
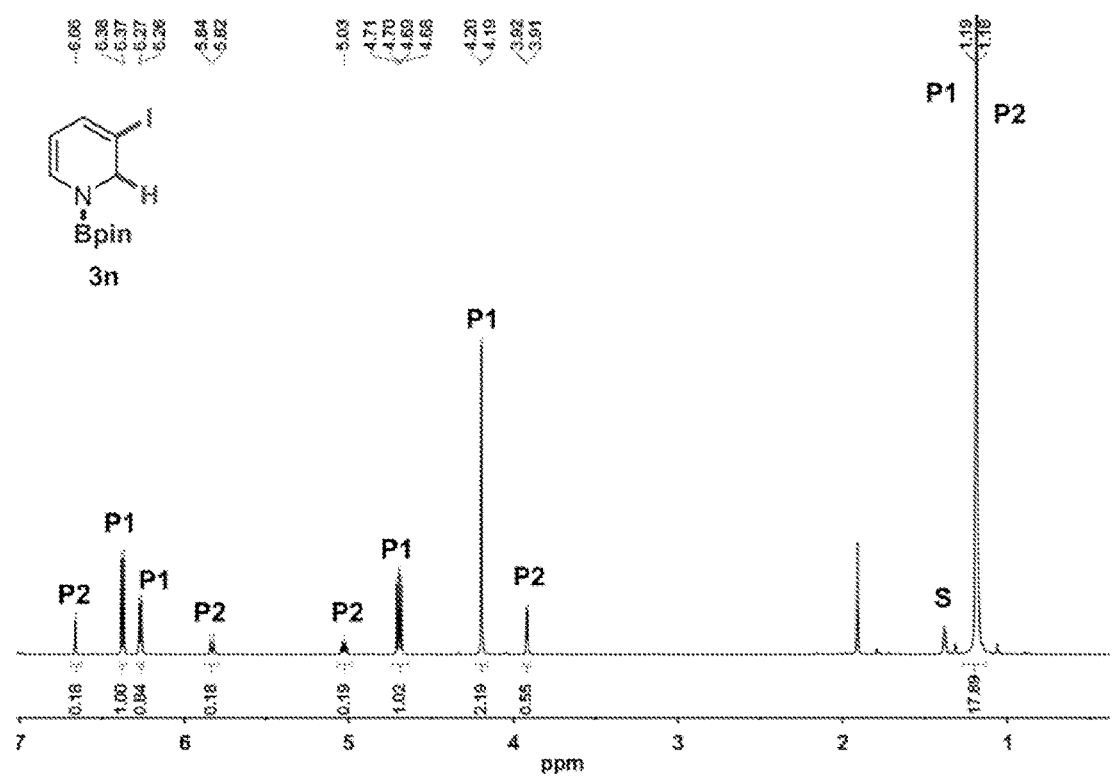
FIG. 17 is a $^1H$ NMR spectrum of 3n in $C_6D_{12}$, wherein P1=3-iodo-1,2-dihydropyridine; P2=5-iodo-1,2-dihydropyridine; and S=solvent.

1-(4,4,5,5-tetramethyl-1,3,2-dioxaborolan-2-yl)-3-iodo-1,2-dihydropyridine and 1-(4,4,5,5-tetramethyl-1,3,2-dioxaborolan-2-yl)-5-iodo-1,2-dihydropyridine (3n). 3-iodo-1,2-dihydropyridine: $^1$H NMR (500 MHz, C$_6$D$_{12}$): δ=6.38 (d, J=5.9 Hz, 1H), 6.27 (d, J=7.2 Hz 1H), 4.70 (dd, J=7.2 Hz, J=5.9 Hz 1H), 4.20 (d, J=1.4 Hz, 2H), 1.19 (s, 12H) ppm. $^{13}$C NMR (125 MHz, C$_6$D$_{12}$): δ=133.0, 131.1, 102.5, 82.8, 78.7, 52.8, 24.1 ppm. 5-iodo-1,2-dihydropyridine: $^1$H NMR (500 MHz, C$_6$D$_{12}$): δ=6.66 (s, 1H), 5.84 (m, 1H), 5.03 (m, 1H), 3.92 (dd, J=4.3 Hz, J=1.7 Hz, 2H), 1.18 (s, 12H) ppm. $^{13}$C NMR (125 MHz, C$_6$D$_{12}$): δ=137.5, 131.0, 115.3, 78.7, 62.7, 40.4, 24.0 ppm. $^{11}$B NMR (128 MHz, C$_6$D$_{12}$): δ=23.5 ppm. HRMS (LC-TOF, positive mode, CH$_2$Cl$_2$/CH$_3$CN): m/z calcd for C$_{11}$H$_{17}$BINO$_2$ 333.04. found: 334.0321 (M-H$^+$) (FIG. 17).

Figure 18:
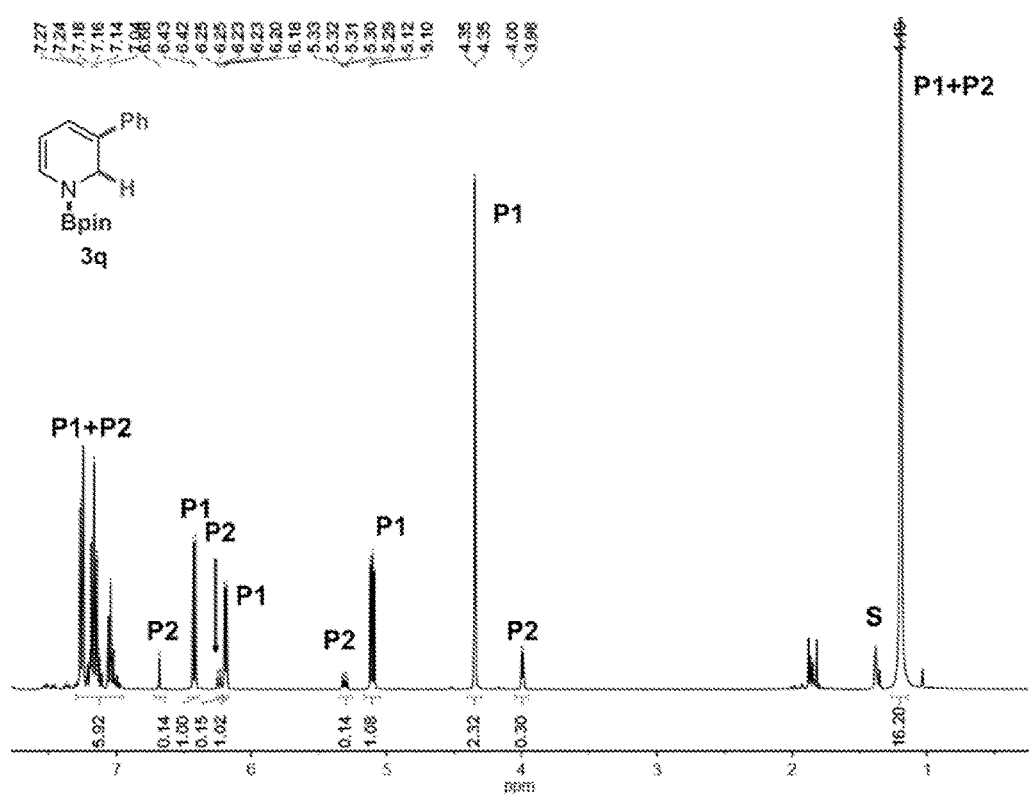
FIG. 18 is a $^1H$ NMR spectrum of 3q in $C_6D_{12}$, wherein P1=3-phenyl-1,2-dihydropyridine; P2=5-phenyl-1,2-dihydropyridine; S=solvent.

1-(4,4,5,5-tetramethyl-1,3,2-dioxaborolan-2-yl)-3-phenyl-1,2-dihydropyridine and 1-(4,4,5,5-tetramethyl-1,3,2-dioxaborolan-2-yl)-5-phenyl-1,2-dihydropyridine (3q). 3-phenyl-1,2-dihydropyridine: $^1$H NMR (500 MHz, C$_6$D$_{12}$): δ=7.27-7.02 (m, 5H), (m, 5H), 6.43 (d, J=7.2 Hz, 1H), 6.19 (d, J=6.4 Hz, 1H), 5.10 (t, J=7.2 Hz, 1H), 4.35 (d, J=1.1 Hz, 2H), 1.19 (s, 12H) ppm. 5-phenyl-1,2-dihydropyridine: $^1$H NMR (500 MHz, C$_6$D$_{12}$): δ=7.27-7.02 (m, 5H), 6.68 (s, 1H), 6.24 (m, 1H), 5.31 (m, 1H), 3.99 (m, 2H), 1.19 (s, 12H) ppm. $^{13}$C NMR (125 MHz, C$_6$D$_{12}$): δ=140.5, 132.9, 129.3, 127.3, 125.5, 125.4, 125.3, 121.0, 116.3, 104.6, 84.0, 45.4, 25.7 ppm. $^{11}$B NMR (128 MHz, C$_6$D$_{12}$): δ=23.8 ppm. HRMS (LC-TOF, positive mode, CH$_2$Cl$_2$/CH$_3$CN): m/z calcd for C$_{17}$H$_{22}$BNO$_2$ 283.17. found: 284.166 (M-H$^+$) (FIG. 18).

Figure 19:
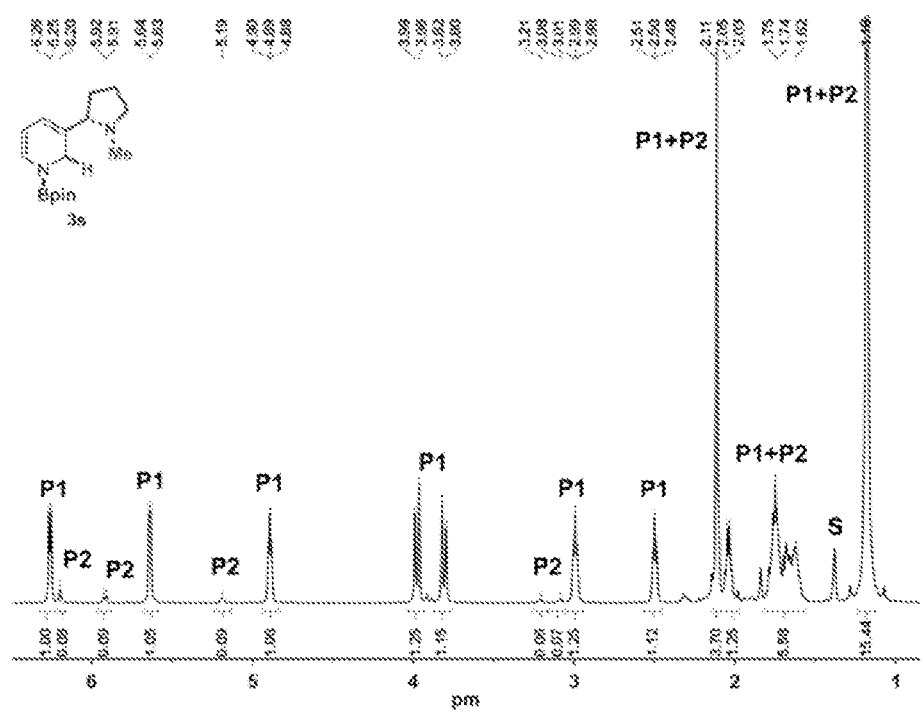
FIG. 19 is a $^1H$ NMR spectrum of 3s in $C_6D_{12}$, wherein P1=3-[(2S)-1-methyl-2-pyrrolidinyl-1,2-dihydropyridine; P2=5-[(2S)-1-methyl-2-pyrrolidinyl-1,2-dihydropyridine; S=solvent.

1-(4,4,5,5-tetramethyl-1,3,2-dioxaborolan-2-yl)-3-[(2S)-1-methyl-2-pyrrolidinyl-1,2-dihydropyridine and 1-(4,4,5,5-tetramethyl-1,3,2-dioxaborolan-2-yl)-5-[(2S)-1-methyl-2-pyrrolidinyl-1,2-dihydropyridine (3s). 3-[(2S)-1-methyl-2-pyrrolidinyl-1,2-dihydropyridine: $^1$H NMR (500 MHz, C$_6$D$_6$): δ=6.26 (d, J=7.1 Hz, 1H), 5.64 (d, J=4.5 Hz, 1H), 4.89 (t, J=5.2 Hz, 1H), 3.98 (d, J=15.0 Hz, 1H), 3.81 (d, J=15.0 Hz, 1H), 2.99 (t, J=6.35 Hz, 1H), 2.50 (t, J=6.35 Hz, 1H), 2.11 (s, 3H), 2.03 (m, 1H), 1.72 (m, 4H), 1.18 (s, 12H) ppm. 5-[(2S)-1-methyl-2-pyrrolidinyl-1,2-dihydropyridine: $^1$H NMR (500 MHz, C$_6$D$_6$): δ=6.20 (s, 1H), 5.92 (d, J=9.6 Hz, 1H), 5.19 (m, 1H), 3.21 (m, 1H), 3.08 (m, 1H), remaining protons overlap with the major product. $^{13}$C NMR (125 MHz, C$_6$D$_6$): δ=131.8, 128.3, 121.0, 103.2, 83.0, 72.4, 57.3, 42.1, 40.4, 30.8, 25.1, 23.4. $^{13}$C NMR (125 MHz, C$_6$D$_6$): δ=129.7, 124.4, 116.5, 115.8, 82.9, 69.7, 57.2, 43.4, 40.2, 32.3, 25.0, 23.0. $^{11}$B NMR (128 MHz, C$_6$D$_6$): δ=23.6 ppm. HRMS (LC-TOF, positive mode, CH$_2$Cl$_2$/CH$_3$CN): m/z calcd for C$_{16}$H$_{27}$BN$_2$O$_2$ 290.21. found: 291.210 (M-H$^+$) (FIG. 19).

Figure 20:
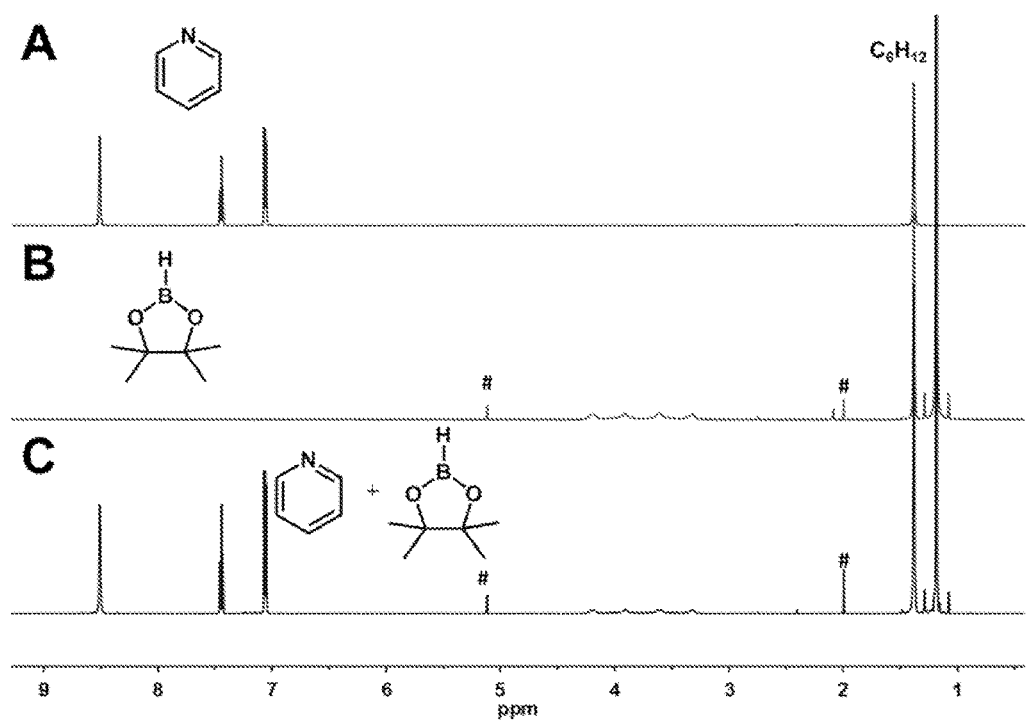
FIG. 20 is a $^1H$ NMR stack spectra plot of a) pyridine, b) HBpin, and c) pyridine+HBpin in $C_6D_{12}$, wherein #=unknown impurity in commercial HBpin.
Figure 21:
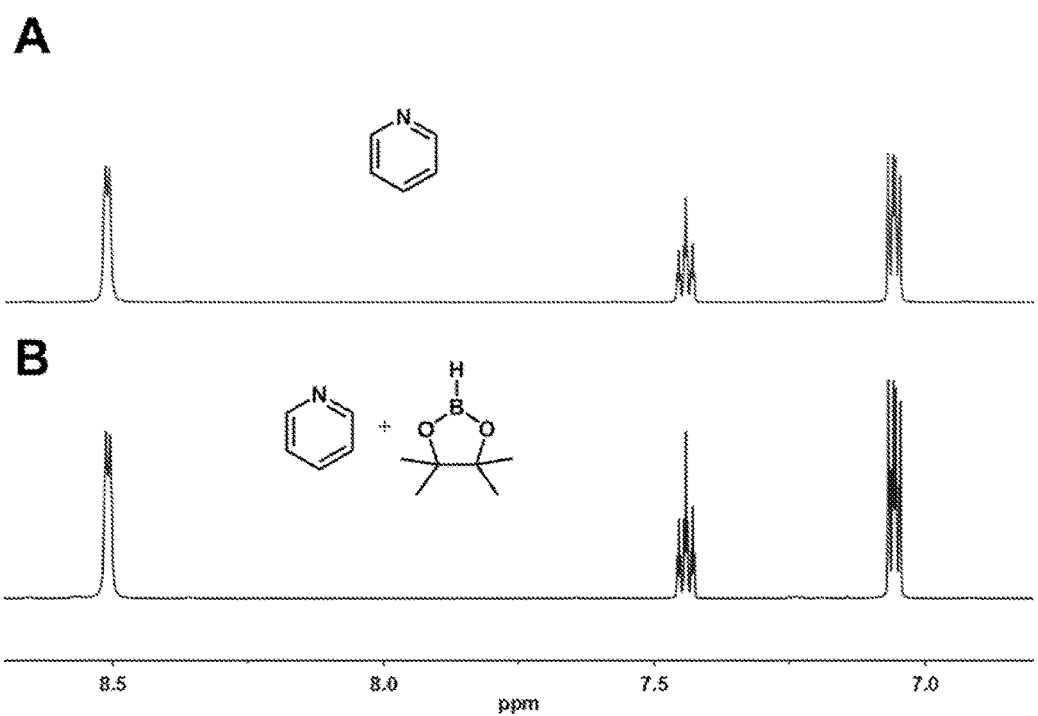
FIG. 21 is an expansion (δ 8.70–6.80 ppm) of the $^1H$ NMR stack spectra plot of a) pyridine and b) pyridine+HBpin in $C_6D_{12}$.
Figure 22:
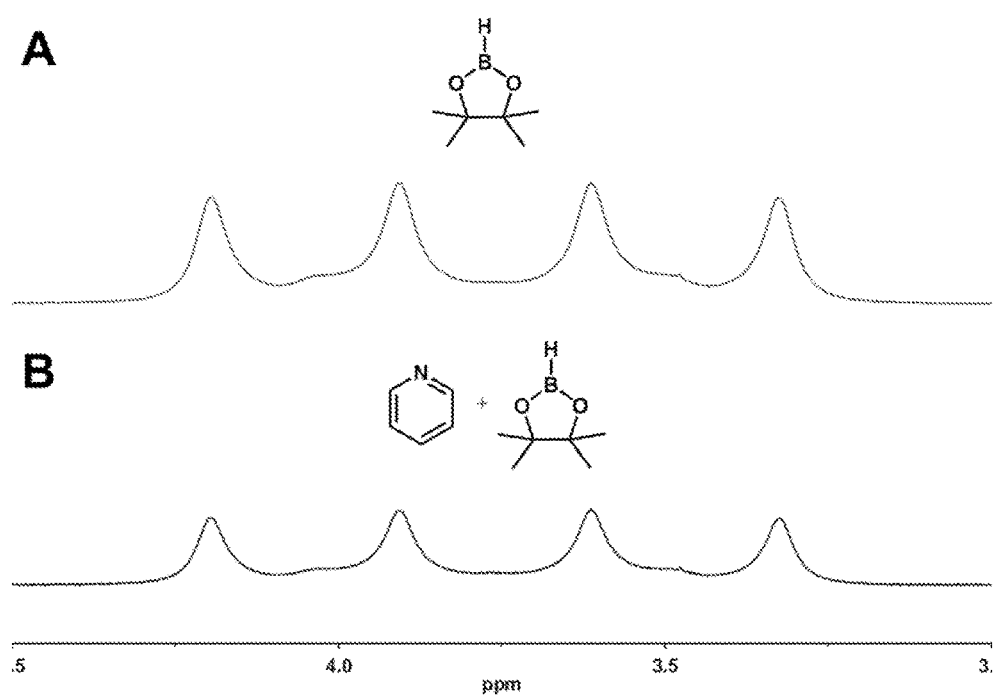
FIG. 22 is an expansion (δ 4.50-3.00 ppm) of the $^1H$ NMR stack spectra plot of a) HBpin and b) pyridine+HBpin in $C_6D_{12}$.

$^1$H NMR Spectra of Pyridine and HBpin. FIG. 20 shows the $^1$H NMR spectra of pyridine, HBpin, and their equimolar mixture in cyclohexane-d$_{12}$. It can be seen that no new resonances are formed or shifted at 35° C. in cyclohexane-d$_{12}$, indicating that there is no complex formation between pyridine and HBpin, as well as that the dearomatization reaction does not occur in the absence of the catalyst. FIG. 21 shows the expansion (δ 8.70-6.80 ppm) of the $^1$H NMR stack spectra plot of pyridine a), and pyridine+HBpin b) in C$_6$D$_{12}$. FIG. 22 shows the expansion (δ 4.50-3.00 ppm) of the $^1$H NMR stack spectra plot of HBpin a) and pyridine+HBpin b) in C$_6$D$_{12}$.

NMR Monitored Stoichiometric Reaction of [Cp*$_2$LaH]$_2$ with Pyridine and HBpin. [Cp*$_2$LaH]$_2$ (1) (3.08 mg, 3.75×10$^{-3}$ mmol) is weighed into J. Young NMR tube, dissolved in 500 µL C$_6$D$_{12}$ and frozen at −30° C. Stock solutions of pyridine (98 µL, 6.76×10$^{-3}$ mmol) and HBpin (98 µL, 6.76×10$^{-3}$ mmol) are mixed together in a small septum-capped vial and then quickly transferred to the frozen solution of 1. The tube is capped immediately and frozen at −78° C. Then, it is slowly warmed in a 10° C. ice bath, quickly mixed, and frozen at −78° C. immediately after mixing. The tube is then warmed to 10° C. in a temperature regulated VT NMR machine and the ensuing reaction monitored by $^1$H NMR.

Figure 23:
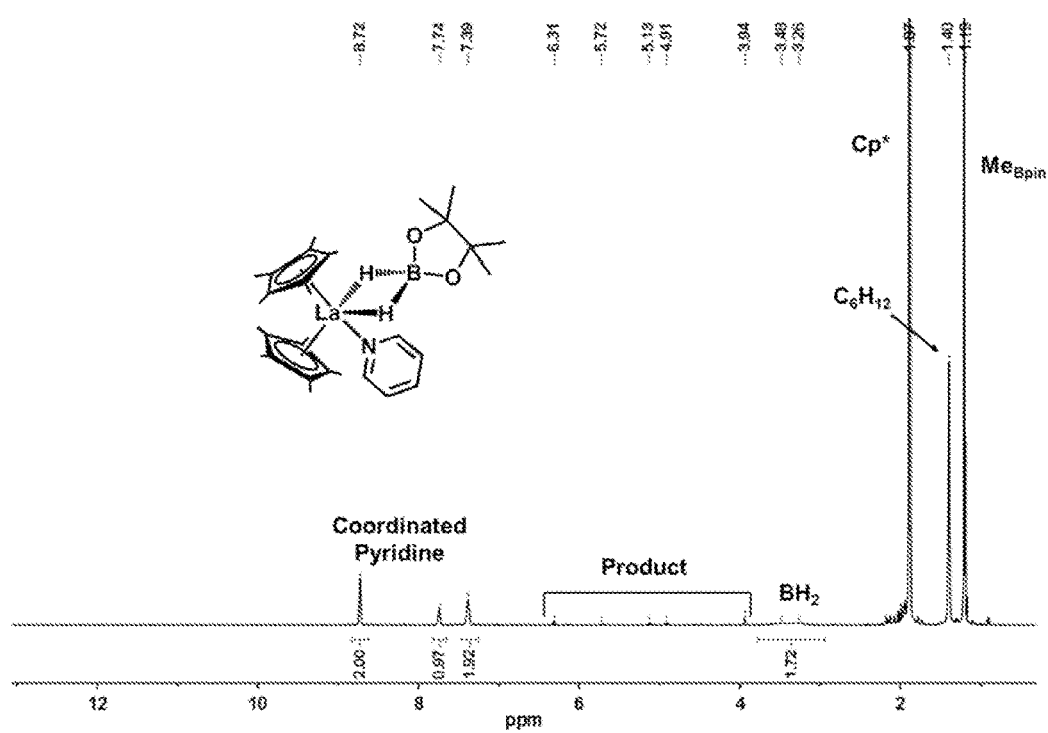
FIG. 23 is a $^1H$ NMR spectrum of the stoichiometric reaction between $[Cp^*_2LaH]_2$, pyridine and HBpin in $C_6D_{12}$, wherein Product=1-(4,4,5,5-tetramethyl-1,3,2-dioxaborolan-2-yl)-1,2-dihydropyridine (3a).
Figure 24:
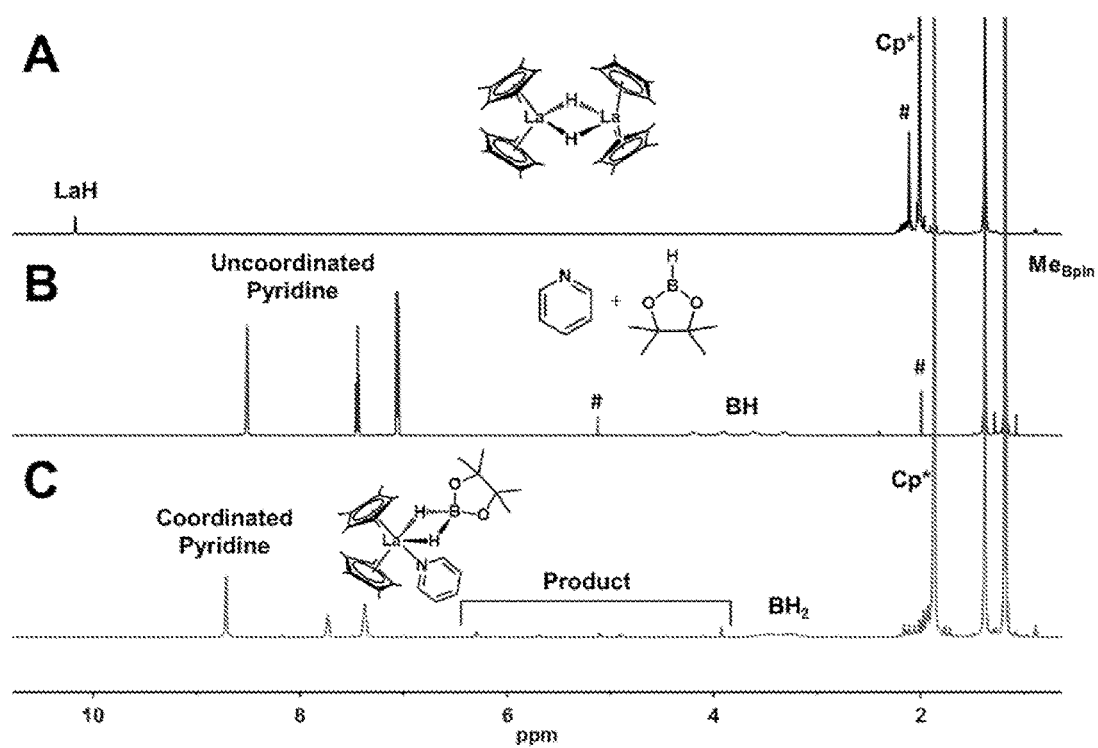
FIG. 24 is a $^1H$ NMR stack spectra plot of a) $[Cp^*_2LaH]_2$, b) pyridine+HBpin, and c) $[Cp^*_2LaH]_2$+pyridine+HBpin in $C_6D_{12}$, wherein Product=1-(4,4,5,5-tetramethyl-1,3,2-dioxaborolan-2-yl)-1,2-dihydropyridine (3a) and #=unidentified impurity.
Figure 25:
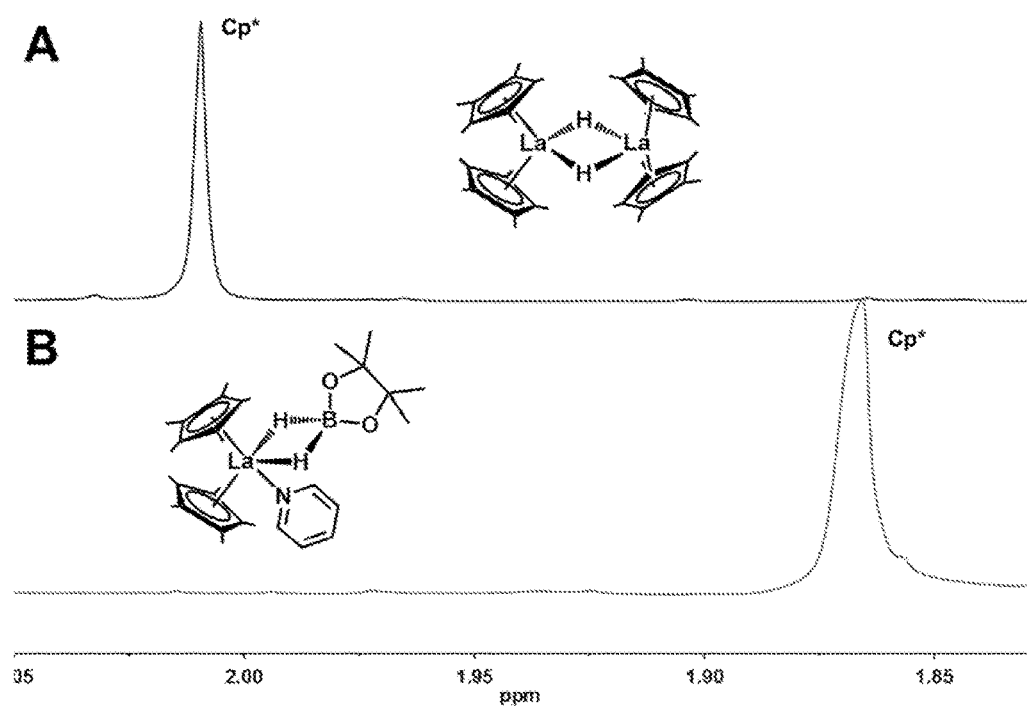
FIG. 25 is an expansion (δ 2.05-1.83 ppm) of $^1H$ NMR stack spectra plot of a) the Cp* region of $[Cp^*_2LaH]_2$, and b) $[Cp^*_2LaH]_2$+pyridine+HBpin in $C_6D_{12}$.
Figure 26:
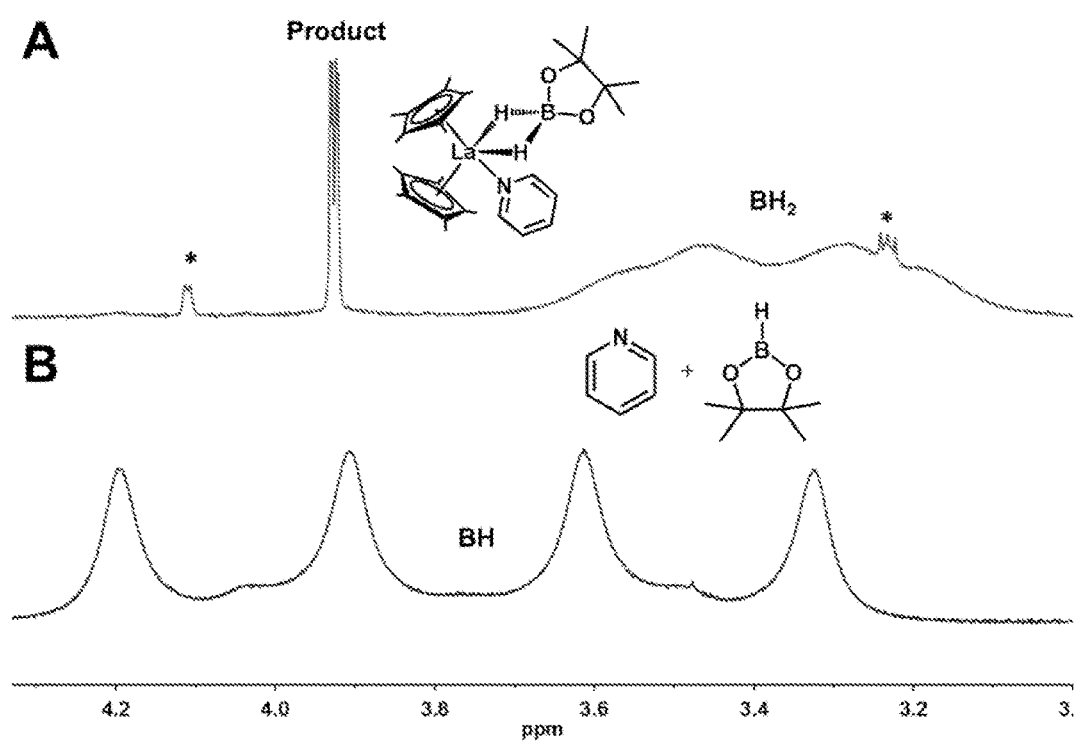
FIG. 26 is an expansion (δ 4.33-3.00 ppm) of $^1H$ NMR stack spectra plot of a) HBpin and b) $[Cp^*_2LaH]_2$+pyridine+

The signals in the $^1$H NMR spectra of the La-complex 1/pyridine/HBpin mixture are noticeably shifted from those of the starting materials (FIGS. 23 and 24). The pyridine peaks are shifted downfield (FIG. 25), indicating a decrease in the overall electron density on pyridine associated with coordination to the lanthanum center. The H—B quartet peak of HBpin is broadened and shifted upfield (FIG. 26), along with the concomitant disappearance of the La—H signal of 1 (FIG. 27). In addition, the integral of new "B—H" peak at –3.4 ppm corresponds to two magnetically equivalent H atoms, suggesting that the hydrides of the former La-complex 1 and HBpin become bridging between B- and La-centers in VIII. The Cp* peaks of the lanthanum catalyst also shift upfield, suggesting an increase in electron density on lanthanum center (FIG. 28). Therefore, the observed $^1$H NMR shifts support formation of the intermediate VIII. However, this complex is quite labile and undergoes decomposition within 30 minutes at 10° C. releasing the 1,2-hydroboration product 3a.

NMR Observation of Intermediate VIII Under Catalytic Reaction Conditions. At an early stage of the catalytic reaction, it is possible to observe the formation of compound VIII in the $^1$H NMR spectrum at 1.86 ppm (FIG. 29c). This signal decreases gradually in intensity and a new peak at 1.98 ppm emerges as the reaction progresses (FIG. 29c versus 29d). Considering a parallel increase in concentration of the final product 3a, this latter signal can be assigned to the complex XIV, in which the generated product weakly coordinates to the lanthanum metal center of the active catalyst. Therefore, both VIII and XIV can be considered as the catalyst "resting" state intermediates at a later stage of the reaction. Expectedly, with further accumulation of the product 3a closer to the end of the reaction, complex 14 becomes the dominant turnover-determining intermediate and the peak at 1.86 ppm (complex VIII) almost completely disappears (FIG. 29e).

NMR Monitored Reaction of [Cp*$_2$LaH]$_2$ with Pyridine. [Cp*$_2$LaH]$_2$ (1) (3.08 mg, 3.75×10$^{-3}$ mmol) is weighed into J. Young NMR tube, dissolved in 500 μL C$_6$D$_{12}$ and frozen at –30° C. Stock solution of pyridine (98 μL, 6.76×10$^{-3}$ mmol) is quickly transferred to the frozen solution of 1. The tube is capped immediately and frozen at –78° C. Then, it is slowly warmed in a 10° C. ice bath, quickly mixed, and frozen at –78° C. immediately after mixing. The tube is then warmed to 25° C. in a temperature regulated VT NMR spectrometer and monitored by $^1$H NMR.

The signals in the $^1$H NMR spectra of the La-complex 1/pyridine mixture are noticeably shifted from those of the starting material. The pyridine peaks are shifted downfield (FIG. 31), indicating a decrease in the overall electron density on pyridine associated with coordination to the lanthanum center. However, after addition of an equimolar HBpin stock solution (98 μL, 6.76×10$^{-3}$ mmol) no appreciable formation of 1,2-hydroboration product 3a is observed.

Reaction of [Cp*$_2$LaH]$_2$ with HBpin. Excess Reaction: HBpin (0.352 mL, 2.43·10Y$^3$ mol) is added to a solution of [Cp*$_2$LaH]$_2$ (0.2 g, 2.43·10$^4$ mol) in dry C$_6$H$_{12}$ (20 mL). The resulting colorless solution is stirred for 3 hours at room temperature. The volatiles are next removed in vacuo and the residue is recrystallized from pentane to give bis-pentamethyl-cyclopentadiene-2-boratetrihydrobutoxy-2,3-dimethyl-3-[(4,4,5,5-tetramethyl-1,3,2-dioxaborolan-2-yl)oxy]lanthanum (4) as a white powder (0.155 g, Yield 96%). Colorless crystals of 4 suitable for X-ray studies are obtained from pentane solution at –40° C. Anal. Calcd for C$_{32}$H$_{57}$B$_2$LaO$_4$ (M=666.30): C, 57.63; H, 8.62. Found: C, 57.61; H, 8.60. $^1$H NMR (500 MHz, C$_6$D$_6$): δ=2.77-2.38 (br m, BH$_3$, 3H), 2.18 (s, Cp*, 30H), 1.30 (s, 2Me, 6H), 1.25 (s, 2Me, 6H), 1.02 (s, Bpin, 12H) ppm. $^{13}$C NMR (126 MHz, C$_6$D$_6$): δ=120.30, 89.35, 84.84, 81.91, 25.06, 24.64, 23.22, 12.43 ppm. $^{11}$B NMR (128 MHz, C$_6$D$_{12}$): δ=22.3 (O—Bpin), –14.4 (O—BH$_3^-$) ppm.

Stoichiometric Reaction: HBpin (0.070 mL, 4.86·10$^{-4}$ mol) is added to a solution of [Cp*$_2$LaH]$_2$ (0.2 g, 2.43·10$^4$ mol) in dry C$_6$H$_{12}$ (20 mL). The resulting colorless solution is stirred for 3 hours at room temperature. The solid, corresponding to complex 4, is collected by filtration, washed with cyclohexane, and dried under vacuum. The volatiles are next removed in vacuo and the residue is analyzed by $^1$H NMR, which confirm the presence of unreacted starting material [Cp*$_2$LaH]$_2$ and unknown compound (FIG. 35).

Attempted catalytic hydroboration of 4-iodopyridine using [RhCl(cod)]$_2$/PCy$_3$. In the glovebox, [RhCl(cod)]$_2$ (1.0 mg, 2 μmol), PCy$_3$ ligand (1.12 mg, 4 μmol), and triphenylmethylsilane (54.9 mg, 0.2 mmol) are weighed into a screw-capped vial. Then, 1.5 mL of C$_6$D$_6$, 4-iodopyridine (410.0 mg, 2 mmol), and HBpin (26.0 mg, 0.2 mmol) are added to the vial. The resulting mixture is sealed, removed from the glove box, and stirred at 50° C. After about 1 hour, the colorless solution turned green and a black precipitate formed. After 24 hours, the mixture is analyzed by $^1$H NMR and no conversion is detected (FIG. 36).

In contrast, when pyridine is used under the same reaction conditions ([RhCl(cod)]$_2$ (1.0 mg, 2 μmol), PCy$_3$ ligand (1.12 mg, 4 μmol), triphenylmethylsilane (54.9 mg, 0.2 mmol), pyridine (158.0 mg, 2 mmol), HBpin (26.0 mg, 0.2 mmol), in 0.2 mL of C$_6$D$_6$), complete conversion is observed after 16 hours at 50° C. (FIG. 37).

X-ray Data Collection, Structure Solution, and Refinement.

Single crystals of C$_{32}$H$_{57}$B$_2$LaO$_4$ (4) are recrystallized from pentane, mounted in inert oil, and transferred to the cold gas stream of a Bruker Kappa APEX CCD area detector equipped with a MoKa sealed tube with graphite. Crystallographic and experimental details of the structure are determined. The crystal is maintained at 100.01 K during data collection. An empirical correction for absorption is made (Sheldrick, G. M. SADABS; Bruker Analytical X-ray Systems, Madison, Wis., 2008). wR2(int) is 0.0656 before and 0.0543 after correction. The ratio of minimum to maximum transmission is 0.8993. The λ/2 correction factor is 0.0015. Using Olex2 (Dolomanov, O. V. et al., *J. Appl. Crystallogr.* 42, 339-341 (2009), incorporated herein by reference), the structure is solved with the XS (Sheldrick, G. M., *Acta Crystallogr.* A 64, 112-122 (2008), incorporated by reference) structure solution program using Patterson Method and refined with the ShelXL refinement package (SHELXTL PC: An Integrated System for Solving, Refining, and Displaying Crystal Structures from Diffraction Data v. Version 6.014 (Bruker AXS, Madison, Wis., 2000) using full-matrix least-squares procedures (based on F$_o^2$) first with isotropic thermal parameters and then with anisotropic thermal parameters in the last cycles of refinement for all non-hydrogen atoms. All hydrogen atoms are located from the residual electron density and freely refined. CCDC 996116 contains the supplementary crystallographic data. These data is obtained free of charge from the Cambridge Crystallographic Data Centre via www.ccdc.cam.ac.uk/data request/cif.

Computational Details. Geometry optimizations of all reactants, products, intermediates and transition states are carried out along the entire catalytic cycle. Calculations are performed adopting the M06 hybrid meta-GGA functional. The effective core potential of Hay and Wadt (LANL2DZ) and the relative basis set were used for the lanthanum and iodine atoms (Yang, S. H. et al., *Organometallics* 25, 1144-1150 (2006); Yang, S. H. et al., *Macromolecules* 37, 5741-5751 (2004), both incorporated herein by reference). The standard all-electron 6-31G** basis is used for all remaining atoms (Rassolov, V. A. et al., *J. Chem. Phys.* 109, 1223-1229 (1998), incorporated herein by reference). Molecular geometry optimization of stationary points is carried out without symmetry constraints and used analytical gradient techniques. The transition states are searched with the "distinguished reaction coordinate procedure" along the emerging bonds. In particular, the hydride transfer step during the insertion of pyridine into the La—H bond is monitored along the emerging C—H bond, the subsequent σ-bond metathesis step induced by the incoming HBpin molecule is monitored along the emerging N—B bond, and the formation of structure VIII is monitored along the emerging B—H bond. Frequency analysis is performed to obtain thermochemical information about the reaction pathways at 298 K using the harmonic approximation. All calculations are performed using the G09 code (Gaussian 09, Revision D.01, Frisch, M. J. et al. Gaussian, Inc., Wallingford Conn., 2009) on Linux cluster systems.

The energetic span model is an effective mathematical framework that allows a straightforward interpretation and global kinetic evaluation of computationally predicted catalytic reaction mechanisms (Kozuch, S. et al., *Acc. Chem. Res.* 44, 101-110 (2010)). According to this model, the experimental rate constant presented as turnover frequency (TOF) is related to the calculated energy profile by the equations 7 and 8 as depicted above, where δE is the energetic span that represents the Gibbs free energy difference between the turnover frequency-determining transition state (TDTS) and turnover frequency-determining intermediate (TDI), if the TDTS appears after the TDI in a reaction profile (equation 14a). When TDTS is followed by TDI, the reaction energy ($\Delta G_r$) is added to this difference (equation 14b). The assignments of a transition state as the TDTS and an intermediate as the TDI are made in a way that these transition state(s) and intermediate(s) yield the highest energetic span δE values possible for a given reaction profile (see Kozuch). Following the strategy outlined above, all of the DFT-computed mechanisms for the present transformations are evaluated using the energetic span methodology with regard to TOFs and reactant concentration effects.

ΔE and ΔG Profiles and ΔE, ΔH, ΔG of the Processes in FIG. 3. Referring to FIG. 38, a) is an energetic profile for transformations of the precatalyst 1 in the presence of pyridine and HBpin reactants: active catalyst generation, inhibition, and deactivation, while b) is an energetic profile of the catalytic cycle for the La-catalyzed pyridine dearomatization along with the off-cycle active catalyst inhibition process. In FIG. 38, all energies are in kcal/mol.

For the conversion of active catalyst VII into dipyridine adduct XI, coordination of the second pyridine is highly stabilizing in terms of potential energy (ΔE=−15.9 kcal/mol), however entropic factors related to the bimolecular association increase the Gibbs free energy. The stabilizing interaction between XII and HBpin to give XIII is confirmed by the elongation of the B—H bond compared to the free HBpin (Δ=0.013 Å). The entropic factors again neutralize the coordination energy gain (ΔE=−15.1 kcal/mol).

TABLE 5

Potential energy (ΔE), enthalpy (ΔH) and Gibbs free energy (ΔG) values (kcal/mol) for the pyridine dearomatization catalytic cycle in FIGS. 3 and 41.

| Species | ΔE, kcal/mol | ΔH, kcal/mol | ΔG, kcal/mol |
| --- | --- | --- | --- |
| VIII | −29.7 | −25.7 | −9.1 |
| TS1 | −10.8 | −9.0 | 8.0 |
| VII | 0.0 | 0.0 | 0.0 |
| XI | −15.9 | −13.7 | 0.6 |
| TS3 | −9.8 | −8.4 | 7.8 |
| XII | −21.8 | −17.1 | −1.8 |
| XIII | −36.9 | −30.6 | −2.3 |
| TS4 | −35.7 | −30.1 | −1.0 |
| XIV | −48.9 | −42.1 | −10.6 |
| VII | −19.3 | −17.0 | −5.5 |

TDI/TDTS Energy Values for the Dearomatization of Substituted Pyridines

TABLE 6

Free energy values of the TDI and TDTS2 states for the dearomatization/hydroboration reaction of substituted pyridines.

| Substrate | ΔG VIII (TDI), kcal/mol | ΔG TS3 (TDTS2), kcal/mol | δE, kcal/mol |
| --- | --- | --- | --- |
| pyridine (2a) | −9.1 | 7.8 | 16.9 |
| 4-substituted | | | |
| 4-CF$_3$-pyridine (2b) | −10.1 | 4.4 | 14.5 |
| 4-Ph-pyridine (2d) | −11.7 | 5.2 | 16.9 |
| 4-I-pyridine (2c) | −9.0 | 5.7 | 14.7 |
| 3-substituted | | | |
| 3-F-pyridine (2k) | −7.8 | 7.5 | 15.3 |
| 3-Cl-pyridine (2l) | −12.1 | 2.6 | 14.7 |
| 3-Br-pyridine (2m) | −10.5 | 4.4 | 14.9 |
| 3-I-pyridine (2n) | −10.9 | 3.3 | 14.2 |

It is noted that the accurate calculation of absolute TOF values is difficult, since even a small inaccuracy in TDTS/TDI energies leads to an exponential error in TOF estimations. However, because of error compensation, relative TOF values for a series of analogous substrates can be quantitatively useful.

Cartesian Coordinates for all Computed Structures. Cartesian coordinates for all computed structures as provided herein is found in FIG. 39.

Thermochemistry Estimations of the La-Catalyzed Pyridine Hydroboration Reaction

TABLE 7

Thermochemistry analysis of the La-catalyzed pyridine 1,2-hydroboration reaction.*

| Bonds Breaking | | Bonds Forming | |
|---|---|---|---|
| | Step 1 | | |
| | H—La←Pyridine[b] | | 9.1 kcal/mol |
| | $\Delta H_{Coordination}$ = −9.1 kcal/mol | | |
| | Step 2 | | |
| La—H[a] | 54.2 kcal/mol | La—N(CH$_2$)—CH=CH—[a] | 45.0 kcal/mol |
| =C—HC=N—CH= (C sp$^2$) | 153.0 kcal/mol | =C—H$_2$C—N(La)—C= (C sp$^3$) | 68.0 kcal/mol |
| | | —C=C—N—C—H(H) | 80.0 kcal/mol |
| | $\Delta H_{Insertion}$ = (54.2 +153.0) − (45.0 + 68.0 + 80) ≈ + 14.2 kcal/mol | | |
| | Step 3 | | |
| La—N(CH$_2$)—CH=CH—[a] | 45.0 kcal/mol | La—H[a] | 54.2 kcal/mol |
| RO$_2$B—H | 78.9 kcal/mol | RO$_2$B—N—CH$_2$— | 92.7 kcal/mol |
| | $\Delta H_{Protonolysis}$ = (45.0 + 78.9) − (54.2 + 92.7) ≈ −23.9 kcal/mol | | |

[a]With Ln/An adjustments.
[b]Estimated from the sum of Ln-phenyl and Ln-thf coordination bond disruption enthalpies.
*H. Y. Afeefy, J. F. Liebman, and S. E. Stein, "Neutral Thermochemical Data" in NIST Chemistry WebBook, NIST Standard Reference Database Number 69, Eds. P. J. Linstrom and W. G. Mallard, National Institute of Standards and Technology, Gaithersburg MD, 20899, http://webbook.nist.gov, (retrieved Jun. 4, 2014); Wobser, S. D. et al., *Organometallics* 32, 1317-1327 (2013); Blanksby, S. J., *Acc. Chem Res* 36, 255-263 (2003); Marks, T. J. *Bonding Energetics in Organometallic Compounds.* Vol. 428 1-18 (ACS Symposium Series 1990); Nolan, S. P. et al., *J. Am. Chem. Soc.* 111, 7844-7853 (1989); Griller, D. et al., *Theochem.-J. Mol Struc.* 40, 125-131 (1988); Bruno, J. W. et al., *J. Am. Chem. Soc.* 108, 7275-7280 (1986); Bruno, J. W. et al., *J. Am. Chem. Soc.* 105, 6824-6832 (1983); and Mcmillen, D. F. & Golden, D. M. Hydrocarbon Bond-Dissociation Energies. *Annu. Rev. Phys. Chem.* 33, 493-352 (1982), all incorporated herein by reference.

CONCLUSIONS

N-boryl-1,2-dihydroazine products 3 are highly air- and moisture-sensitive and decompose rapidly when exposed to the conditions describe above. Hydroboration of pyridine with HBpin catalyzed by [RhCl(cod)]$_2$/phosphine ligand provides mixtures of 1,2- and 1,4-dihydropyridine, and the regioselectivity is ligand-dependent. The magnesium-catalyzed hydroboration generally proceeds with lower degrees of selectivity often favoring the formation of 1,4-isomeric products. Under the conditions in Table 2, the reaction is not compatible with substrates bearing acidic (i.e., CO$_2$H, OH) and highly electrophilic CHO groups, most likely due to catalyst decomposition. The dearomatization reactions of 3-bromopyridine (2m) at 10 or 60° C. do not exhibit appreciable differences in isomer ratios 3m:3m' relative to that performed at 35° C.

In conclusion, a highly efficient 1,2-regioselective dearomatization of a diverse set of azines with pinacolborane using an earth-abundant organolanthanide catalyst is provided. The process employs equimolar amounts of reagents, displays good functional group compatibility, and enables the regiospecific preparation of a wide range of 1,2-dihydropyridines. The dearomatized products are prominent motifs in many naturally occurring and pharmacologically active compounds and serve as useful intermediates in the synthesis of valuable nitrogen-containing molecules. Particularly noteworthy is the ability of the present catalytic system to address shortcomings of existing pyridine dearomatization methods, especially the reliance on precious transition metal catalysts. Mechanistic studies reveal an experimental rate law with a variable dependence on pyridine concentration and an unusual inverse first-order dependence on pinacolborane concentration. DFT calculations with an Energetic Span evaluation suggest a turnover-determining Cp*$_2$LaH(pyridine)(pinacolborane) "resting state" and identify two turnover-determining transition states—dissociation of pinacolborane from the Cp*$_2$LaH (pyridine) active catalyst and 1,2-addition of the La—H bond to the pyridine C=N unsaturation. These results are in excellent agreement with the experimental kinetics and reactivity trends, and are further supported by in situ stoichiometric spectroscopic experiments.

What is claimed is:

1. A method for dearomatizing an aromatic azine ring compound, said method comprising treating an azine ring compound comprising at least one nitrogen atom with at least one main-group element hydride in the presence of an organolathanide catalyst to afford a 1,2-dearomatized azine.

2. The method according to claim 1, wherein the 1,2-dearomatized azine is regioselective.

3. The method according to claim 2, wherein the regioselective 1,2-dearomatized azine is a regioselective 1,2-dihydropyridine.

4. A method according to claim 1, wherein the at least one main-group element hydride is pinacolborane.

5. A method according to claim 1, wherein the organolanthanide catalyst has a formula of (L)$_x$Ln-H, wherein L is an ancillary ligand selected from a group consisting of Cp, Cp* and CGC, Cp"; Ln is a lanthanide element; X is an integer selected from a group consisting of 1 and 2; and H is hydrogen.

6. A method according to claim 5, wherein the lanthanide element is selected from a group consisting of Sc, Y, La, Sm, Nd, Yb and Lu.

7. A method according to claim 1, wherein the azine is a substituted with one or more subsituents.

8. A method according to claim 7, wherein the one or more substituents are independently selected from a group consisting of halogen, CF$_3$, OMe, (2S)-1-methyl-2-pyrrolidinyl, 1-piperidinyl, phenyl, vinyl, SnMe$_3$, Bpin and fused ring systems and combinations thereof.

9. A method according to claim 1, wherein the azine is pyridine.

10. A method according to claim 1, wherein the azine and the at least one main-group element hydride are present in equimolar quantity.

11. A method according to claim 10, wherein the catalyst is present in less than equimolar quantity relative to the azine and the at least one main-group element hydride.

12. A method according to claim 11, wherein the catalyst is present in about 1% stoichiometric quantity relative to the azine and the at least one main-group element hydride.

13. A method according to claim 1, wherein the treating of the azine with at least one main-group element hydride in the presence of an organolathanide catalyst is performed in a solvent comprising benzene.

14. A method according to claim 3, wherein the regioselective 1,2-dihydropyridine is selected from a group consisting of:

1-(4,4,5,5-tetramethyl-1,3,2-dioxaborolan-2-yl)-1,2-dihydropyridine;

1-(4,4,5,5-tetramethyl-1,3,2-dioxaborolan-2-yl)-4-(trifluoromethyl)-1,2-dihydropyridine;

1-(4,4,5,5-tetramethyl-1,3,2-dioxaborolan-2-yl)-4-phenyl-1,2-dihydropyridine;

1-(4,4,5,5-tetramethyl-1,3,2-dioxaborolan-2-yl)-4-methyl-1,2-dihydropyridine;

1-(4,4,5,5-tetramethyl-1,3,2-dioxaborolan-2-yl)-3-fluoro-1,2-dihydropyridine;

1-(4,4,5,5-tetramethyl-1,3,2-dioxaborolan-2-yl)-3-methyl-1,2-dihydropyridine;

1-(4,4,5,5-tetramethyl-1,3,2-dioxaborolan-2-yl)-3,5-methyl-1,2-dihydropyridine;

1-(4,4,5,5-tetramethyl-1,3,2-dioxaborolan-2-yl)-3-methoxy-1,2-dihydropyridine;

1-(4,4,5,5-tetramethyl-1,3,2-dioxaborolan-2-yl)-1,2-dihydroquinoline;

1-(4,4,5,5-tetramethyl-1,3,2-dioxaborolan-2-yl)-1,2-dihydroisoquinoline;

1,4-Bis(4,4,5,5-tetramethyl-1,3,2-dioxaborolan-2-yl)-1,2,3,4-tetrahydropyrazine;

1-(4,4,5,5-tetramethyl-1,3,2-dioxaborolan-2-yl)-4-iodo-1,2-dihydropyridine;

1-(4,4,5,5-tetramethyl-1,3,2-dioxaborolan-2-yl)-4-methoxy-1,2-dihydropyridine;

1-(4,4,5,5-tetramethyl-1,3,2-dioxaborolan-2-yl)-4-piperidino-1,2-dihydropyridine;

1-(4,4,5,5-tetramethyl-1,3,2-dioxaborolan-2-yl)-4-(4,4,5,5-tetramethyl-1,3,2-dioxaborolan-2-yl)-1,2-dihydropyridine;

1-(4,4,5,5-tetramethyl-1,3,2-dioxaborolan-2-yl)-4-vinyl-1,2-dihydropyridine;

1-(4,4,5,5-tetramethyl-1,3,2-dioxaborolan-2-yl)-4-trimethylstannyl-1,2-dihydropyridine;

1-(4,4,5,5-tetramethyl-1,3,2-dioxaborolan-2-yl)-3-chloro-1,2-dihydropyridine;

1-(4,4,5,5-tetramethyl-1,3,2-dioxaborolan-2-yl)-5-chloro-1,2-dihydropyridine;

1-(4,4,5,5-tetramethyl-1,3,2-dioxaborolan-2-yl)-3-bromo-1,2-dihydropyridine;

1-(4,4,5,5-tetramethyl-1,3,2-dioxaborolan-2-yl)-5-bromo-1,2-dihydropyridine;

1-(4,4,5,5-tetramethyl-1,3,2-dioxaborolan-2-yl)-3-iodo-1,2-dihydropyridine;

1-(4,4,5,5-tetramethyl-1,3,2-dioxaborolan-2-yl)-5-iodo-1,2-dihydropyridine;

1-(4,4,5,5-tetramethyl-1,3,2-dioxaborolan-2-yl)-3-phenyl-1,2-dihydropyridine;

1-(4,4,5,5-tetramethyl-1,3,2-dioxaborolan-2-yl)-5-phenyl-1,2-dihydropylidine;

1-(4,4,5,5-tetramethyl-1,3,2-dioxaborolan-2-yl)-3-[(2S)-1-methyl-2-pyrrolidinyl-1,2-dihydropyridine; and 1-(4,4,5,5-tetramethyl-1,3,2-dioxaborolan-2-yl)-5-[(2S)-1-methyl-2-pyrrolidinyl-1,2-dihydropyridine (3s).

\* \* \* \* \*